United States Patent
Viscidi et al.

(10) Patent No.: US 9,580,474 B2
(45) Date of Patent: Feb. 28, 2017

(54) POLYIONIC PAPILLOMA VIRUS-LIKE PARTICLE (VLP) VACCINES

(75) Inventors: Raphael Paul Viscidi, Baltimore, MD (US); Ioannis Bossis, College Park, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 88 days.

(21) Appl. No.: 13/821,579

(22) PCT Filed: Sep. 8, 2011

(86) PCT No.: PCT/US2011/050820
§ 371 (c)(1),
(2), (4) Date: Sep. 21, 2013

(87) PCT Pub. No.: WO2012/033911
PCT Pub. Date: Mar. 15, 2012

(65) Prior Publication Data
US 2014/0050753 A1    Feb. 20, 2014

Related U.S. Application Data

(60) Provisional application No. 61/380,813, filed on Sep. 8, 2010.

(51) Int. Cl.
*A61K 39/12* (2006.01)
*C07K 14/025* (2006.01)
*C07K 14/005* (2006.01)
*A61K 39/00* (2006.01)
*A61K 47/48* (2006.01)

(52) U.S. Cl.
CPC ........ *C07K 14/005* (2013.01); *A61K 39/0011* (2013.01); *A61K 39/12* (2013.01); *A61K 47/48276* (2013.01); *A61K 47/48776* (2013.01); *A61K 2039/5258* (2013.01); *A61K 2039/6075* (2013.01); *C12N 2710/20022* (2013.01); *C12N 2710/20023* (2013.01); *C12N 2710/20043* (2013.01); *C12N 2770/24134* (2013.01)

(58) Field of Classification Search
None
See application file for complete search history.

(56) References Cited

U.S. PATENT DOCUMENTS

2010/0172936 A1    7/2010    Lowy et al.

OTHER PUBLICATIONS

Christensen et al. Hybrid Papillomavirus L1 Molecules Assemble into Virus-like Particles That Reconstitute Conformational Epitopes and Induce Neutralizing Antibodies to Distinct HPV Types. Virology 291, 324-334 (2001).*
GenBank: AAD33259.1. L1 [Human papillomavirus type 16]. http://www.ncbi.nlm.nih.gov/protein/AAD33259.1. Jun. 30, 2000.*
GenBank: AAA46935.1. major capsid protein [Human papillomavirus type 11]. Jun. 14, 1994. http://www.ncbi.nlm.nih.gov/protein/496201?report=genbank&log$=protalign&blast_rank=2&RID=3VEFCSM3014.*
Chen et al. Structure of Small Virus-like Particles Assembled from the L1 Protein of Human Papillomavirus 16. Molecular Cell, vol. 5, 557-567, Mar. 2000.*
Olcese et al. Characterization of HPV16 L1 loop domains in the formation of a type-specific, conformational epitope. BMC Microbiology 2004, 4:1-11.*
Laird et al. Infectivity and neutralization of simian immunodeficiency virus with FLAG epitope insertion in gp120 variable loops. J Virol. Oct. 2007;81(20):10838-48. Epub 2007 Aug. 8.*
Roden et al. Minor capsid protein of human genital papillomaviruses contains subdominant, cross-neutralizing epitopes. Virology. May 10, 2000;270(2):254-7.*
Hearn et al. Applications of novel affinity cassette methods: use of peptide fusion handles for the purification of recombinant proteins. J. Mol. Recognit. 2001; 14: 323-369.*
Schellenbacher et al. Chimeric L1-L2 virus-like particles as potential broad-spectrum human papillomavirus vaccines. J Virol. Oct. 2009;83(19):10085-95. Epub Jul. 29, 2009.*
GenBank: CAB46515.1. capsid protein L1 [Bovine papillomavirus type 1]. Oct. 23, 2008.*
Stubenrauch et al. Purification of a viral coat protein by an engineered polyionic sequence. J. Chromatogr. B. Biomed. Sci. Appl. 2000.737, 77-84.*
Stubenrauch et al. Conjugation of an antibody Fv fragment to a virus coat protein: cell-specific targeting of recombinant polyoma-virus-like particles. Biochem J. Jun. 15, 2001;356(Pt 3):867-73.*
Pejawar-Giddy, et al., Cancer Immunol. Immunother, (2010), vol. 59, No. 11, pp. 1685-1696.
Greenstone, et al., Proc. Natl. Acad. Sci. USA, (1998), vol. 95, No. 4, pp. 1800-1805.
Xu, et al., Arch. Virol., (2006), vol. 151, No. 11, pp. 2133-2148.
Acres, B., et al., "MUC1 as a target antigen for cancer immunotherapy" Expert Rev. Vaccines vol. 4, No. 4, pp. 193-502 (2005).
Aktas, E., et al., "Relationship between CD107a expression and cytotoxic activity" Cell. Immunol. vol. 254, pp. 149-154 (2009).
Alajez, N., et al., "Therapeutic potential of a tumor-specific, MHC-unrestricted T-cell receptor expressed on effector cells of the innate and the adaptive immune system through bone marrow transduction and immune reconstitution" Blood, vol. 105, No. 12, pp. 4583-4589 (2005).

(Continued)

*Primary Examiner* — Nick Zou
(74) *Attorney, Agent, or Firm* — Johns Hopkins Technology Transfer

(57) ABSTRACT

The present invention relates to the field of vaccines. In particular, the present invention provides compositions and methods relating to virus-like particle (VLP) vaccines. In one embodiment, a chimeric papillomavirus virus-like particle (VLP) comprises the L1 protein, wherein the HI loop of the L1 protein comprises negatively charged amino acids. In a more specific embodiment, a chimeric bovine papillomavirus VLP comprises the L1 protein, wherein the amino acid sequence EEEEEEEEC is inserted into the HI loop of the L1 protein.

21 Claims, 35 Drawing Sheets

(56) References Cited

OTHER PUBLICATIONS

Andreasson, K., et aL, "Murine pneumotropic virus chimeric Her2/neu virus-like particles as prophylactic and therapeutic vaccines against Her2/neu expressing tumors" Int. J. Cancer, vol. 124, pp. 150-156 (2009).

Boisgerault, F., et al., "Virus-like particles: a new family of delivery systems" Expert Rev. Vaccines, vol. 1, No. 1, pp. 101-109 (2002).

Bontkes, H., et al., "Plasmacytoid dendritic cells are present in cervical carcinoma and become activated by Human Papillomavirus type 16 virus-like particles" Gynecol. Oncol., vol. 96, pp. 897-901 (2005).

Brockhausen, I., et al., "Mechanisms underlying aberrant glycosylation of MUC1 mucin in breast cancer cells" Eur. J. Biochem., vol. 233, pp. 607-617 (1995).

Buck, C., et al., "Arrangement of L2 within the Papillomavirus Capsid" J. Virol., vol. 82, No. 11, pp. 5190-5197 (2008).

Byrd, J., et al., "Mucins and mucin binding proteins in colorectal cancer" Cancer Metastasis Rev., vol. 23, pp. 77-99 (2004).

Chackerian, B., et al., "Conjugation of a self-antigen to papillomavirus-like particles allows for efficient induction of protective autoantibodies" J. Clin. Invest., vol. 108, pp. 415-423 (2001).

Chen, X., et al., "Structure of Small Virus-like Particles Assembled from the L1 Protein of Human Papillomavirus 16" Mol. Cell., vol. 5, pp. 557-567 (2000).

Devevre, E., et al., "LiveCount Assay: Concomitant measurement of cytolytic activity and phenotypic characterisation of CD8+ T-cells by flow cytometry" J. Immunol. Methods, vol. 311, pp. 31-46 (2006).

Dickgreber, N., et al., "Targeting Antigen to MHC Class II Molecules Promotes Efficient Cross-Presentation and Enhances Immunotherapy" J. Immunol., vol. 182, pp. 1260-1269 (2009).

Dorn, D., et al., "Cellular and Humoral Immunogenicity of Hamster Polyomavirus-Derived Virus-Like Particles Harboring a Mucin 1 Cytotoxic T-Cell Epitope" Viral Immunol., vol. 21, No. 1, pp. 12-27 (2008).

Fifis, T., et al., "Size-Dependent Immunogenicity: Therapeutic and Protective Properties of Nano-Vaccines against Tumors" J. Immunol., vol. 173, No. 5, pp. 3148-3154 (2004).

Gedvilaite, A., et al., "Virus-like particles derived from major capsid protein VP1 of different polyomaviruses differ in their ability to induce maturation in human dendritic cells" Virology, vol. 354, pp. 252-260 (2006).

Goriely, S., et al., "Interleukin-12 family members and the balance between rejection and tolerance" Curr. Opin. Organ Tranplant., vol. 13, pp. 4-9 (2008).

Grgacic, E., et al., "Virus-like particles: Passport to immune recognition" Methods, vol. 40, pp. 60-65 (2006).

Karsten, U., et al., "What Makes MUC1 a Tumour Antigen?" Tumour Biol., vol. 26, pp. 217-220 (2005).

Kotera, Y., et al., "Humoral immunity against a tandem repeat epitope of human mucin MUC-1 in sera from breast, pancreatic, and colon cancer patients" Cancer Res., vol. 54, pp. 2856-2860 (1994).

Li, Y., et al., "MUC1 is a Promising Therapeutic Target for Prostate Cancer Therapy" Curr. Cancer Drug Targets, vol. 7, pp. 259-271 (2007).

McKolanis, J., et al., "Analysis of the Frequency of MHC-Unrestricted MUC1-Specific Cytotoxic T-Cells in Peripheral Blood by Limiting Dilution Assay" Methods Mol. Biol., vol. 125, pp. 463-470 (2000).

Miyamura, K., et al., "Parvovirus particles as platforms for protein presentation" Proc. Natl. Acad. Sci. USA, vol. 91, pp. 8507-8511 (1994).

Muller, M., et al., "Chimeric Papillomavirus-like Particles" Virology, vol. 234, pp. 93-111 (1997).

North, S., et al., "Vaccination with BLP25 liposome vaccine to treat non-small cell lung and prostate cancers" Expert Rev. Vaccines, vol. 4, No. 3, pp. 249-257 (2005).

Peacey, M., et al., "Versatile RHDV Virus-Like Particles: Incorporation of Antigens by Genetic Modification and chemical Conjugation" Biotechnol. Bioeng., vol. 98, No. 5, pp. 968-977 (2007).

Roy, P., et al., "Virus-like particles as a vaccine delivery system" Hum. Vaccin., vol. 4, No. 1, pp. 5-12 (2008).

Rudolf, M., et al., "Human Dendritic Cells Are Activated by Chimeric Human Papillomavirus Type-16 Virus-Like Particles and Induce Epitope-Specific Human T Cell Responses In Vitro" J. Immunol., vol. 166, pp. 5917-5924 (2001).

Schiller, J., et al., "An Update of Prophylactic Human Papillomavirus L1 Virus-Like Particle Vaccine Clinical Trial Results" Vaccine, vol. 26 (Suppl 10) K53-K61 (2008).

Soares, M., et al., "Three Different Vaccines Based on the 140-Amino Acid MUC1 Peptide with Seven Tandemly Repeated Tumor-Specific Epitopes Elicit Distinct Immune Effector Mechanisms in Wild-Type Versus MUC1-Transgenic Mice with Different Potential for Tumor Rejection" J. Immunol., vol. 166, pp. 6555-6563 (2001).

Stubenrauch, K., et al., "Conjugation of an antibody Fv fragment to a virus coat protein: cell-specific targeting of recombinant polyomavirus-like particles" Biochem. J., vol. 356, pp. 867-873 (2001).

Tegerstedt, K., et al., "Dendritic cells loaded with polyomavirus VP1/VP2Her2 virus-like particles eYciently prevent outgrowth of a Her2/neu expressing tumor" Cancer Immunol. Immunother., vol. 56, pp. 1335-1344 (2007).

Tindle, R., et al., "Chimeric hepatitis B core antigen particles containing B- and Th-epitopes of human papillomavirus type 15 E7 protein induce specific antibody and t-helper responses in immunised mice" Virology, vol. 200, pp. 547-557 (1994).

Trus, B., et al., "Novel structural features of bovine papillomavirus capsid revealed by a three-dimensional reconstruction to 9A resolution" Nat. Struct. Biol., vol. 4, No. 5, pp. 413-420 (1997).

Turner, M., et al., "Lack of Effective MUC1 Tumor Antigen-Specific Immunity in MUC1-Transgenic Mice Results from a Th/T Regulatory Cell Imbalance That Can Be Corrected by Adoptive Transfer of Wild-Type Th Cells" J. Immunol., vol. 178, pp. 2787-2793 (2007).

Vlad, A., et al., "Complex Carbohydrates Are Not Removed During Processing of Glycoproteins by Dendritic Cells" J. Exp. Med., vol. 196, No. 11, pp. 1435-1446 (2002).

Vlad, A., et al., "MUC1 Immunobiology: From Discovery to Clinical Applications" Adv. Immunol., vol. 82, pp. 249-293 (2004).

Wagner, R., et al., "Construction, Expression, and Immunogenicity of Chimeric HIV-1 Virus-like Particles" Virology, vol. 220, pp. 128-140 (1996).

Yan, M., et al., "Despite differences between dendritic cells and Langerhans cells in the mechanism of papillomavirus-like particle antigen uptake, both cells cross-prime T cells" Virology, vol. 324, pp. 297-310 (2004).

Yang, R., et al., "Papillomavirus-Like Particles Stimulate Murine Bone Marrow-Derived Dendritic Cells to Produce Alpha Interferon and Th1 Immune Responses via MyD88" J. Virol., vol. 78, No. 20, pp. 11152-11160 (2004).

\* cited by examiner

General features of conjugation site

```
Chimeric VLP:   X-Cys-Glu-Glu-Glu-Glu-Glu-Glu-Glu-Glu-Y    SEQ ID NO:29
                :  |   |   |   |   |   |   |   |   :
NH2-tagged Ag:  Cys-Arg-Arg-Arg-Arg-Arg-Arg-Arg-Arg-Cys-Y  SEQ ID NO:13
```

Negatively charged glutamic acids
interact with positively charged arginines
and cysteines form covalent bond

Specific Antigens of Interest

MUC1-20mer-CTL epitopes
Cell surface epithelial mucin: novel glycoform is a tumor antigen
RRRRRRRRCGSG-GVTSAPDTRPAPGSTAPPAH          SEQ ID NO:6

Human papillomvirus (HPV) 16 E7 CTL epitope aa49-57
well characterized model CTL epitope
CRRRRRRRRCAAY-RAHYNIVTF    SEQ ID NO:8

P. falciparum circumsporozoite protein B cell epitope
CRRRRRRRRCG-NANPNVDPNANPNVDPNANPNVDPNANP   SEQ ID NO:15

P. yoelii circumsporozoite protein CD8 T cell epitope
CRRRRRRRRCAAY-SYVPSAEQI    SEQ ID NO:18

FIG. 12

HI loop constructs

- Deletion
  - ASD$_{346}$CEEEEEEES$_{356}$KF    SEQ ID NO:35
- Insertion
  - ASDGT$_{348}$GSSGCEEEEE EECGSSGL$_{350}$TEYDSSKF    SEQ ID NO:36
- Partial Deletion
  - ASDGT$_{348}$CEEEEEEED$_{354}$SSKF    SEQ ID NO:37

VLP formation and protein expression

| Construct | Capsid Yield | Capsomere Yield | L1 protein expression |
|---|---|---|---|
| Deletion | ++ | - | + |
| Insertion | + | ++++ | +++++ |
| Partial deletion | ++++ | ++ | +++++ |

FIG. 14

Malaria Vaccines

Malaria kills approximately 900,000 people a year worldwide and sickens tens of millions more, most of them children living in Sub-Saharan Africa

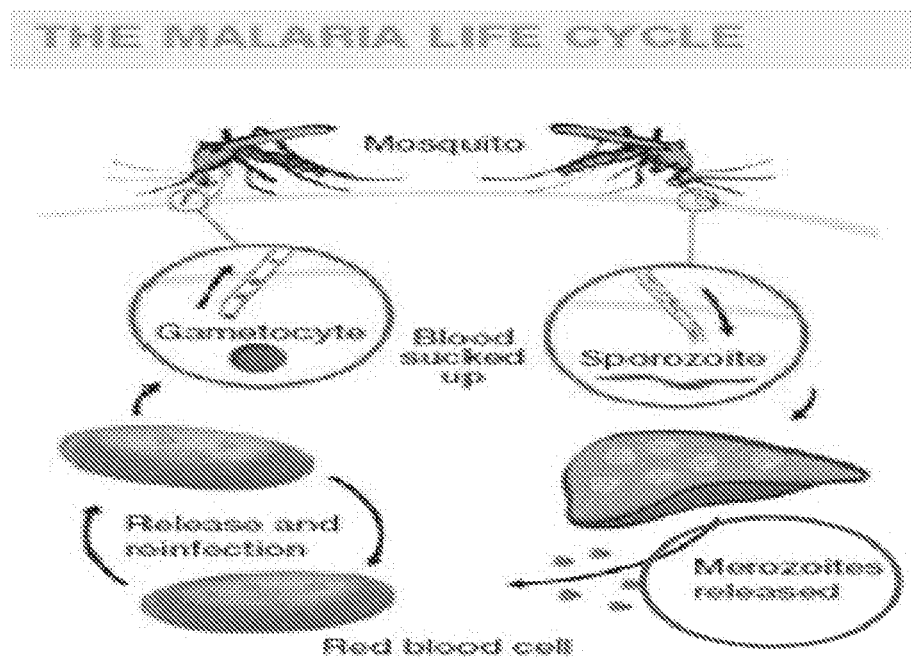

GlaxoSmithKline RTS,S malaria vaccine
- Recombinant protein and adjuvant vaccine
- Part of P falciparum CS protein fused to HepB surface antigen
- Fusion protein forms particulate structure
- Induces antibody and T cell responses
- Efficacy 30-45%
- Correlate of protection unknown, but not solely antibody

Model chimeric malaria VLP vaccine
- P. falciparum CS NANP repeat peptide
- P. yoelii CS immunodominant CTL epitope
- B cell adjuvant alum and MPLA
- T cell adjuvant Quil A

POLYIONIC PAPILLOMA VIRUS-LIKE PARTICLE (VLP) VACCINES

CROSS-REFERENCE TO RELATED APPLICATIONS

This application is a 35 U.S.C. §371 U.S. national entry of International Application PCT/US2011/050820 having an international filing date of Sep. 8, 2011, which claims the benefit of U.S. Provisional Application No. 61/380,813, filed Sep. 8, 2010, the contents of each of the aforementioned applications are herein incorporated by reference in their entireties.

FIELD OF THE INVENTION

The present invention relates to the field of vaccines. In particular, the present invention provides compositions and methods relating to virus-like particle (VLP) vaccines.

INCORPORATION-BY-REFERENCE OF MATERIAL SUBMITTED ELECTRONICALLY

This application contains a sequence listing. It has been submitted electronically via EFS-Web as an ASCII text file entitled "P11195-02_ST25.txt." The sequence listing is 36,219 bytes in size, and was created on Sep. 7, 2011. It is hereby incorporated by reference in its entirety.

BACKGROUND OF THE INVENTION

Virus-like particles (VLPs), which resemble in size and morphology true capsids but do not incorporate viral genetic material, are attractive vaccine candidates because they are non-infectious, they have the safety profile of subunit vaccines, but have superior immunological properties. See Grgacic et al., 40 METHODS 60-5 (2006). The particulate nature of VLPs, especially those in the size range of 40-50 nm (Fifis et al., 173 J. IMMUNOL. 3148-54 (2004), allows efficient uptake by dendritic cells (DCs), central players in initiation of the innate and adaptive immune response. VLPs can stimulate maturation of DCs, induce upregulation of major histocompatability complexes (MHC) and costimulatory molecules, and lead to production of cytokines. VLPs also serve as their own adjuvant, eliciting "danger signals," often through stimulation via Toll-like receptors. As exogenous antigens, VLPs are processed and presented by MHC class II, but they can also be taken up and processed via the MHC class I pathway by cross presentation. See Dickgreber et al., 182 J. IMMUNOL. 1260-69 (2009).

In order to expand the application of VLPs as vaccines, efforts have been made to devise chimeric VLPs that present epitopes of proteins that cannot self assemble. See Boisgérault et al., 1 EXPERT REV. VACCINES 101-09 (2002). The most common way in which this has been achieved is to construct fusions proteins of a VLP protein and a candidate vaccine peptide. Despite the described successes of this approach, there are limitations to the size and nature of epitopes that can be inserted into VLPs. Novel approaches for the generation of potent VLP vaccines are greatly needed.

SUMMARY OF THE INVENTION

The present invention relates to the field of vaccines. In particular, the present invention provides compositions and methods relating to virus-like particle (VLP) vaccines. The present invention is based, in part, on the discovery that polyionic papilloma VLPs can induce potent antibody responses and potent cellular immune responses. The VLPs of the present invention activate antigen presenting cells (APCs) due to its particulate structure and inherent properties to activate innate immune response.

In one aspect, the present invention provides chimeric papillomavirus VLPs comprising the L1 protein. In one embodiment, the VLP the HI loop of the L1 protein comprises negatively charged amino acids. In a specific embodiment, the HI loop of the L1 protein comprises about 4 to about 15 negatively charged amino acids. In another specific embodiment, the HI loop of the L1 protein comprises about 4 to about 12 negatively charged amino acids. In a more specific embodiment, the HI loop of the L1 protein comprises about 4 to about 8 negatively charged amino acids.

The negatively charged amino acids of the VLPs of the present invention can be glutamic acid, aspartic acid, or both. In a specific embodiment, the negatively charged amino acids are glutamic acids. In certain embodiments, the negatively charged amino acids are in consecutive order.

In further VLP embodiments, the HI loop of the L1 protein further comprises one or more cysteines. In a specific embodiment, the HI loop of the L1 protein further comprises one or more cysteines that are adjacent to the negatively charged amino acids.

The papillomavirus VLPs of the present invention can be human, bovine, equine, ovine, porcine, deer, canine, feline, or rabbit. In one embodiment, the papillomavirus is bovine. In another embodiment, the papillomavirus is human.

In the VLPs of the present invention, the L1 protein can be the full length protein. In other embodiments, the L1 protein is a L1 polypeptide fragment that is capable of forming a VLP. The VLPs of the present invention may further comprise the L2 protein. In one embodiment, the L2 protein is the full length protein. In another embodiment, the L2 protein is a L2 polypeptide fragment that is capable of forming a VLP with the L1 protein.

In a specific embodiment, a chimeric papillomavirus VLP comprises the L1 protein, wherein the amino acid sequence EEEEEEEEC (SEQ ID NO: 11) is inserted into the HI loop of the L1 protein. The papillomavirus can be human, bovine, equine, ovine, porcine, deer, canine, feline, or rabbit. In a specific embodiment, the papillomavirus is bovine. In another specific embodiment, the papillomavirus is human. In a more specific embodiment, the EEEEEEEEC (SEQ ID NO: 11) amino acid sequence replaces amino acids 347-355 of the HI loop of the L1 protein. In another embodiment, the EEEEEEEEC (SEQ ID NO: 11) amino acid sequence replaces amino acids 349-353 of the HI loop of the L1 protein.

In a specific embodiment, a chimeric bovine papillomavirus VLP comprises SEQ ID NO: 1. In another embodiment, a chimeric bovine papillomavirus VLP comprises SEQ ID NO:2. In a further embodiment, a chimeric bovine papillomavirus VLP comprises SEQ ID NO:3. In yet another embodiment, a chimeric bovine papillomavirus VLP comprises SEQ ID NO:4.

In another embodiment, a chimeric bovine papillomavirus VLP comprises the L1 protein, wherein the amino acid sequence EEEEEEEEC (SEQ ID NO:11) is inserted into the HI loop of the L1 protein. In a more specific embodiment, the EEEEEEEEC (SEQ ID NO: 11) amino acid sequence can be inserted into amino acid positions 346-356 of the HI loop of the L1 protein.

In another aspect, the present invention provides vaccines comprising a VLP as claimed herein. In particular embodiments, the vaccine further comprises a target antigen, wherein the target antigen comprises a region of positively charged amino acids, and wherein the negatively charged amino acids of the HI loop of the VLP are covalently bound to the positively charged region of the target antigen. The positively charged amino acids can be arginine, histidine, lysine, or a combination thereof. In a specific embodiment, the positively charged amino acids are arginine. In other embodiments, the region of positively charged amino acids is in consecutive order. In a further embodiment, one or more cysteines are adjacent to the region of positively charged amino acids.

In particular embodiments, the target antigen is a peptide or a polypeptide. In a specific embodiment, the target antigen is a peptide. The target is selected from the group consisting of a tumor antigen, viral antigen, bacterial antigen, fungal antigen, parasitic antigen, and a pathogenic self protein. In certain embodiments, the target antigen is fusion protein. In a specific embodiment, the target antigen is MUC1 peptide. In another embodiment, the target antigen is human papillomavirus 16 E7 CTL epitope amino acids 49-57. In an alternative embodiment, the target antigen is *P. falciparum* circumsporozoite NANP repeat protein B cell epitope. In a further embodiment, the target antigen is *P. yoellii* circumsporozoite protein CD8 T-cell epitope. In yet another embodiment, the target antigen is Dengue virus CD8 epitope. In yet another embodiment, the target antigen is Severe Acute Respiratory Syndrome (SARS) virus CD8 epitope.

The present invention also provides methods for inducing an immune response comprising administering a vaccine described herein. In certain vaccine embodiments, the chimeric papillomavirus VLP is human and further comprises a human papillomavirus VLP comprising native L1 protein.

In yet another embodiment, a chimeric papillomavirus VLP comprises the L1 protein, wherein the H4 loop of the L1 protein comprises negatively charged amino acids. In a more specific embodiment, a chimeric papillomavirus VLP comprises the L1 protein, wherein the amino acid sequence CEEEEEEEE is inserted into the H4 loop of the L1 protein. In a more specific embodiment, the CEEEEEEEE amino acid sequence replaces amino acids 413-421 of the H4 loop of the L1 protein.

BRIEF DESCRIPTION OF THE FIGURES

FIG. 1A is a Western blot analysis using a monoclonal anti-BPV L1 in lysates of Hi5 cells infected with the four recombinant baculoviruses BPV-BC-E8c (SEQ ID NO:1), BPV-DE-E8c (SEQ ID NO:2), BPV-HI-E8c (SEQ ID NO:3), BPV-H4-E8c (SEQ ID NO:4), and BPV-WT (SEQ ID NO:5) expressing the chimeric and native L1 proteins. FIG. 1B is a Western blot analysis of purified BPV-DE-E8c, BPV-HI-E8c, and BPV-H4-E8c. The BPVBC-E8c did not result in any particle formation. FIG. 1C shows BPV-HI-E8c VLPs, magnification 30 K, the scale bar is 100 nm. FIG. 1D shows BPV-H4-E8c capsomeres, magnification at 70 K, scale bar is 50 nm. FIG. 1E shows BPV-DE-E8c partially assembled VLPs, magnification at 30 K, the scale bar is 100 nm. For electron microscopy, the purified particles were loaded on carbon-coated copper grids, negatively stained with 2% potassium phosphotungstate (pH=7), and visualized under a JEOL 1200 TEM.

FIG. 2A presents SDS-PAGE and Coomasie brilliant blue staining of conjugated BPV-HI-E8c VLPs. Ten, twenty and thirty micrograms of conjugated VLPs and 100 ng of R8c-MUC1 (SEQ ID NO:6) (mass standard) were loaded on separate lanes. Due to overloading of the gel (at 30 μg), delayed band migration was observed. The L1 runs according to the theoretical MW of 56 kd. The R8c-MUC1 runs as ~6 kd. FIG. 2B shows immunogold labeling of BPV-HI-E8c VLPs conjugated with the R8c-MUC1 peptide. The conjugated VLPs were adsorbed on formvar/carbon-coated nickel grids. The primary antibody was monoclonal anti-MUC1 IgG, and the secondary was colloidal-gold-conjugated (6 nm) goat anti mouse IgG. Negative staining was performed with 1% sodium silicotungstate (pH=6.5). Magnification is at 40K and the scale bar is 100 nm.

In FIG. 3A, bone marrow dendritic cells (DC) (BMDC) were loaded with various BPV constructs (WT BPV, BPV-HI-E8c-MUC1, BPV-HI-E8c; BPVH4-E8c-MUC1, BPV-H4-E8c) for 24 h, and subsequently were stained for standard DC maturation markers CD40, CD80, CD86 and MHC class II and analyzed by flow cytometry (unconjugated vs. mock: p=0.000195; conjugated vs. mock: p=0.0000035). In FIG. 3B, supernatants harvested from DC cultures, 24 h post-treatment with various constructs, were used to assess IL-12 secretion using IL-12 ELISA (unconjugated vs. mock: p=0.0236; conjugated vs. mock: p=0.00346684). DC alone (untreated—UT), MUC1 peptide (250 ng-GVTSAPDTRPAPGSTAPPAH) (SEQ ID NO:7). *p<0.05; **p<0.01.

FIG. 8 shows the effect of reaction conditions on conjugation of MUC1 polycationic peptides on chimeric VLPs.

FIG. 12 shows the general features of the conjugation site between a polyanionic chimeric VLP and a polycationic target antigen. Negatively charged glutamic acids interact with positively charged arginines. Cysteines on both molecules form a disulfide bond under oxidizing conditions. FIG. 12 also presents exemplary target antigens of interest.

FIG. 14 shows that choice of surface loop and position of polyglutamic acid:cysteine sequence within the loop affects VLP and L1 protein yield and particle formation.

FIG. 23 shows the malaria life cycle and describes a current malaria vaccine, as well as target antigens that would make a model chimeric malaria VLP vaccine.

DETAILED DESCRIPTION OF THE INVENTION

Figure 1:
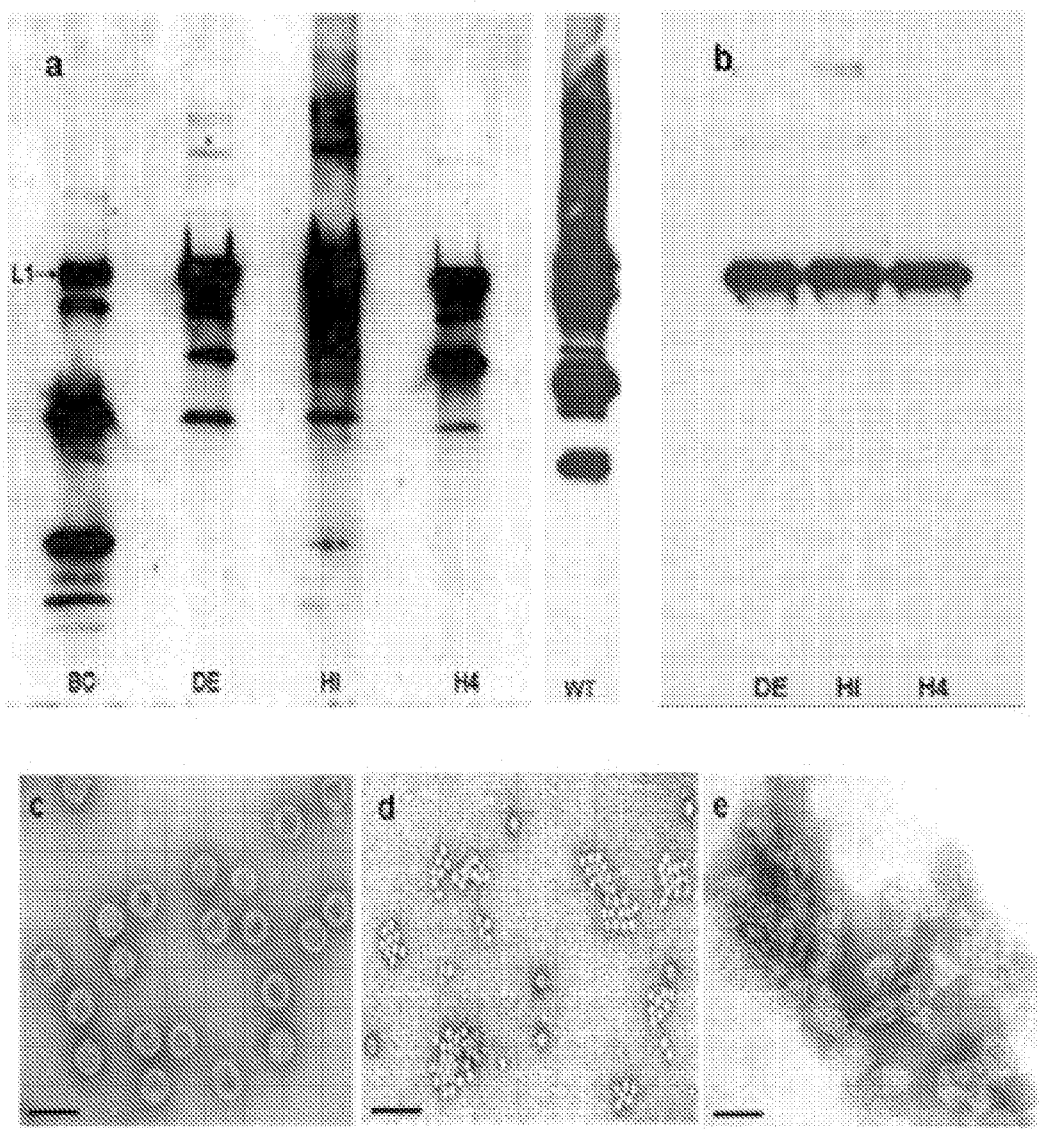
FIG. 1 shows the expression profile of chimeric L1 constructs and electron micrographs of purified chimeric particles.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Papillomavirus Virus-Like Particles

The present invention relates to the production of chimeric papillomavirus virus-like particles (VLPs), and use thereof as a vaccine platform. Papillomaviruses are small, double-stranded, circular DNA tumor viruses. The papillomavirus virion shells contain the L1 major capsid protein and the L2 minor capsid protein. Expression of L1 protein alone or in combination with L2 protein in eukaryotic or prokaryotic expression systems is known to result in the assembly of capsomeres and VLPs. As used herein, the term "capsomere" is intended to mean a pentameric assembly of papillomavirus L1 polypeptides (including full-length L1 protein and fragments thereof). Native L1 capsid proteins self-assemble via intermolecular disulfide bonds to form pentamers (capsomeres).

The papillomavirus virion contains 72 pentamers (capsomeres) of L1 protein. Trus et al., 4 NAT. STRUCT. BIOL. 413-20 (1997). The L1 protein is capable of self-assembly into capsid-like structures that are morphologically indistinguishable from native virions when expressed in eukaryotic cells. See Buck et al., 82 J. VIROL. 5190-97 (2008) and Roy et al., 4 HUM. VACCIN. 5-12 (2008). The L1 monomer contains 12 β-strands, 6 loops (BC, CD, DE, EF, FG, HI), and 5 helices (H1-H5). Most of the loops are highly exposed towards the outer surface of the capsid, and insertion of the polyionic docking site, as described herein, in these areas will result in the site being displayed on the outer surface of VLPs.

As used herein, the term "virus-like particle" or "VLP" refers to a particle comprised of a higher order assembly of capsomeres. VLPs are non-infectious and non-replicating, yet morphologically similar to native papillomavirus virion. One example of such a higher order assembly is a particle that has the visual appearance of a whole (72 capsomere) or substantially whole, empty papillomavirus capsid, which is about 50 to about 60 nm in diameter and has a T=7 icosahedral construction. Another example of such a higher order assembly is a particle of about 30 to about 35 nm in diameter, which is smaller than the size of a native papillomavirus virion and has a T=1 construction (containing 12 capsomeres). For purposes of the present invention, other higher order assemblies of capsomeres are also intended to be encompassed by the term VLP. In certain embodiments, the VLPs can replicate conformational epitopes of the native papillomavirus from which the L1 protein or polypeptide or L2 protein or polypeptide is derived. Methods for assembly and formation of human papillomavirus VLPs and capsomeres of the present invention are well known in the art. See, e.g., U.S. Pat. No. 6,165,471 and U.S. Pat. No. 6,153,201, as well as WO 94/020137.

In several embodiments, the chimeric papillomavirus VLP comprises an L1 polypeptide. In other embodiments, the VLP can comprise an L1 polypeptide and an L2 polypeptide. The L1 polypeptide can be full-length L1 protein or an L1 polypeptide fragment. In specific embodiments, the full-length L1 protein or L1 polypeptide fragment is VLP assembly-competent; that is, the L1 polypeptide will self-assemble to form capsomeres that are competent for self-assembly into a higher order assemblies, thereby forming a VLP. In more specific embodiments, the VLPs comprise a fully assembled papillomavirus capsid, a structure of about 50 nm and composed of 72 capsomeres.

The L1 sequences are known for substantially all papillomavirus genotypes identified to date, and any of these L1 sequences or fragments can be employed in the present invention. Examples of L1 polypeptides include, without limitation, full-length L1 polypeptides (e.g., Accession No. P03103) (SEQ ID NO:5), L1 truncations that lack the native C-terminus, L1 truncations that lack the native N-terminus, and L1 truncations that lack an internal domain. See Conway et al., 88(4) J. DENTAL RES. 307-17 (2009); Chen et al., 5 MOL. CELL. 557-67 (2000); and Paintsil et al., 223(1) VIROLOGY 238-44 (1996).

The L2 polypeptide can be full-length L2 protein or an L2 polypeptide fragment. The L2 sequences are known for substantially all papillomavirus genotypes identified to date, and any of these L2 sequences or fragments can be employed in the present invention. Examples of L2 polypeptides include, without limitation, full-length L2 polypeptides (e.g., Accession No. P03109) (SEQ ID NO:10), L2 truncations that lack the native C-terminus, L2 truncations that lack the native N-terminus, and L2 truncations that lack an internal domain.

The chimeric papillomavirus VLPs can be formed using the L1 and optionally L2 polypeptides from any animal papillomavirus, or derivatives or fragments thereof. Thus, any known (or hereafter identified) L1 and optional L2 sequences of human, bovine, equine, ovine, porcine, deer, canine, feline, rodent, rabbit, etc., papillomaviruses can be employed to prepare the VLPs or capsomeres of the present invention. See de Villiers et al., 324 VIROLOGY 17-27 (2004) for a near complete listing of papillomavirus genotypes and their relatedness.

In certain embodiments, the L1 and optionally L2 polypeptides that are used to form the VLPs are from a non-human papillomavirus or a human papillomavirus genotype other than HPV-6, HPV-11, HPV-16, and HPV-18. This embodiment may be commercially desirable, because it may avoid the possibility of inducing immune tolerance against any HPV genotypes that are utilized in commercial HPV vaccines. To the extent that commercial vaccine formulations are altered, then it is contemplated to utilize L1 and optionally L2 polypeptides derived from human papillomaviruses other than those presented in such vaccine formulations.

As used herein, the term "chimeric" is intended to denote VLPs that include polypeptide components from two or more distinct sources. This term is not intended to confer any meaning concerning the specific manner in which the polypeptide components are bound or attached together. In particular embodiments, a chimeric VLP (whether it comprises an L1 polypeptide or L1/L2 polypeptides) comprises a region of negatively charged amino acids on a surface exposed area that is capable of binding to a target antigen comprising a region of negatively charged amino acids. In further embodiments, the region of negatively charged amino acids may be flanked, on either or both sides, by one or more cysteine residues (referred to as polyanionic:cysteine or more specifically, polyglutamic acid:cysteine or polyaspartic acid:cysteine). In such cases, the conjugation of the VLP and target antigen would result from non-covalent binding between the complementary amino acid charges and a disulfide bond between the cysteines. In other embodiments, the cysteine(s) are one or more amino acids away from the region of charged amino acids such that any secondary/tertiary structure would bring the charged amino acid region in close proximity to the cysteine(s).

Negatively charged amino acids that can be used in producing the chimeric VLP include glutamic acid and aspartic acid. These amino acids can be used singly (e.g., polyglutamic acid) or in combination. In a specific embodiment, the region comprises glutamic acid. The number of negatively charged amino acids can vary, and can include about 4 to about 20 amino acids, about 6 to about 18 amino acids, about 8 to about 16 amino acids, and the like. In a specific embodiment, the region comprises about 8 negatively charged amino acids. In a more specific embodiment, the region comprises EEEEEEEEC (E8C) (SEQ ID NO: 11). In another embodiment, the region comprises CEEEEEEEEC (SEQ ID NO:29). One of ordinary skill in the art can, through routine experimentation, create a VLP that includes a polyionic region in a surface exposed area (e.g., one or more loops) and that is VLP assembly competent.

In alternative embodiments, the chimeric papillomavirus VLP is engineered to include display a region of positively charged amino acids and one or more cysteines (polycationic:cysteine) on a surface exposed area that is capable of binding to a target antigen that comprises a region of negatively charged amino acids and one or more cysteines (polyanionic:cysteine).

In specific embodiments, a chimeric VLP comprises an L1 polypeptide (e.g., full length) where a polyanionic:cysteine amino acid region is inserted into one or more loops of the L1 polypeptide (e.g., HI loop). Such regions can, for example, be inserted into the amino acid sequence encoding a particular loop (with no deletion of corresponding L1 amino acids), inserted and replacement of L1 amino acids in the loop, or even an insertion and partial deletion of L1 amino acids in the particular loop). Indeed, through routine experimentation, one of ordinary skill in the art can optimize the chimeric VLP vaccine platform to suit particular target antigens.

The genetic constructs encoding the chimeric L1 protein (e.g., full or partial length L1 polypeptide), and optionally the L2 protein (e.g., full or partial length L2 polypeptide), can be prepared according to standard recombinant procedures well known to those of ordinary skill in the art. DNA molecules encoding the various polypeptide components are ligated together to form an in-frame gene fusion that results in, for example, a single open reading frame that expresses the polyionic papillomavirus capsid polypeptide (L1 or L1/L2). The DNA coding sequences, or open reading frames, encoding the whole or partial L1 and/or L1/L2 polypeptides can be ligated to appropriate regulatory elements that provide for expression (i.e., transcription and translation) of the fusion protein encoded by the DNA molecule. These regulatory sequences, typically promoters, enhancer elements, leader sequences, transcription terminal signals, etc., are well known in the art.

When a prokaryotic host cell is selected for subsequent transformation, the promoter region used to construct the recombinant DNA molecule should be appropriate for the particular host. As is well known in the art, the DNA sequences of eukaryotic promoters, for expression in eukaryotic host cells, differ from those of prokaryotic promoters. Eukaryotic promoters and accompanying genetic signals may not be recognized in or may not function in a prokaryotic system, and, further, prokaryotic promoters are not recognized and do not function in eukaryotic cells.

Thus, the DNA molecules encoding the polypeptide products to be expressed in accordance with the present invention can be cloned into a suitable expression vector using standard cloning procedures known in the art, including restriction enzyme cleavage and ligation with DNA ligase as described by Sambrook et al., Molecular Cloning: A Laboratory Manual, Second Edition, Cold Spring Harbor Press, NY (2001), and Ausubel et al., Current Protocols in Molecular Biology, John Wiley & Sons, New York, N.Y. (2008), each of which is hereby incorporated by reference in its entirety. Recombinant molecules, including plasmids, can be introduced into cells via transformation, particularly transduction, conjugation, mobilization, or electroporation. Once these recombinant plasmids are introduced into unicellular cultures, including prokaryotic organisms and eukaryotic cells, the cells are grown in tissue culture and vectors can be replicated.

For the recombinant expression of the papillomavirus L1 protein (and optionally an L2 protein), and resulting VLP assembly, the recombinant vectors produced above are used to infect a host cell. Any number of vector-host combinations can be employed, including plant cell vectors (Agrobacterium) and plant cells, yeast vectors and yeast hosts, baculovirus vectors and insect host cells, vaccinia virus vectors and mammalian host cells, or plasmid vectors in $E. coli$. Additional mammalian expression vectors include those derived from adenovirus adeno-associated virus, nodavirus, and retroviruses.

In particular embodiments, the VLPs of the present invention are formed in Sf-9 insect cells upon expression of the L1 protein using recombinant baculovirus. General methods for handling and preparing baculovirus vectors and baculovirus DNA, as well as insect cell culture procedures, are known to those of ordinary skill in the art. See, e.g., Volpers et al., 69 J. VIROL. 3258-64 (1995); Kirnbauer et al., 67(12) J. VIROL. 6929-36 (1993); Kool et al., 130 ARCH. VIROL. 1-16 (1993); Rose et al., 67(4) J. VIROL. 1936-44 (1993).

In alternative embodiments, recombinant expression vectors and regulatory sequences suitable for expression of papillomavirus VLPs in yeast or mammalian cells are well known and can be used in the present invention. See, e.g., Buonamassa et al., 293(2) VIROLOGY 335-44 (2002); Sasagawa et al., 2016 VIROLOGY 126-95 (1995); Hagensee et al., 67(1) J. VIROL. 315-22 (1993). See also, U.S. Pat. No. 7,112,330 and U.S. Patent Publication No. 20080166371.

Regardless of the host-vector system utilized for the recombinant expression and self-assembly of capsomeres and/or VLPs, these products can be isolated from the host cells, and then purified using known techniques. In one embodiment, chimeric papillomavirus VLPs can be purified by centrifugation in CsCl or sucrose gradients. See Sasagawa et al., 2016 VIROLOGY 126-95 (1995); Volpers et al., 69 J. VIROL. 3258-64 (1995); Rose et al., 75 J. GEN. VIROL. 2445-49 (1994); Kirnbauer et al., 67(12) J. VIROL. 6929-36 (1993); Rose et al., 67(4) J. VIROL. 1936-44 (1993). Substantially pure VLP preparations can be conjugated with a polyionic target antigen, and then used as the active agent in a vaccine.

II. Target Antigens

In certain embodiments, the polyionic papillomavirus VLPs of the present invention are conjugated with a target antigen. Target antigens can include tumor antigens, viral antigen, bacterial antigens, fungal antigens, parasitic antigens, and pathogenic self proteins.

In certain embodiments, the target antigen is a polypeptide. As used herein, the terms "polypeptide," "peptide," and "protein" are used interchangeably to refer to polymers of amino acids of any length. Thus, peptides, oligopeptides, and proteins are included within the definition of polypeptide. This term also encompasses post expression modifications of the polypeptide, for example, glycosylations, acetylations, phosphorylations and the like. Included within the definition are, for example, polypeptides containing one or more analogues of an amino acid (including, for example, unnatural amino acids, etc.), polypeptides with substituted linkages, as well as other modifications known in the art, both naturally occurring and non-naturally occurring.

In particular embodiments, the polypeptide target antigen is engineered to include a region of positively charged amino acids that is capable of binding to the chimeric VLP that displays a region of negatively charged amino acids present on a surface exposed region. In further embodiments, the region of positively charged amino acids may be flanked, on either or both sides, by one or more cysteine residues. In such cases, the conjugation of the VLP and target antigen would results from non-covalent binding between the complementary charges and a disulfide bond between cysteines. In other embodiments, the cysteine(s) are one or more amino acids away from the region of amino acids such that any secondary/tertiary structure would bring the charged amino acid region in close proximity to the cysteine(s).

Positively charged amino acids that can be used in producing the target antigen include arginine, histidine and lysine. These amino acids can be used singly (e.g., polyarginine) or in combination. In a specific embodiment, the region comprises arginine. The number of positively charged amino acids can vary, and can include about 4 to about 20 amino acids, about 6 to about 18 amino acids, about 8 to about 16 amino acids, and the like.

In a specific embodiment, the region comprises about 8 positively charged amino acids. In a more specific embodiment, the region comprises RRRRRRRRC (R8C) (SEQ ID NO:12). In another embodiment, the region comprises CRRRRRRRRC (SEQ ID NO:13). In a more specific embodiment, the region comprises CRRRRRRRR (SEQ ID NO:16).

The target antigen sequence can further be optimized to include a leader or linker sequence, e.g., between the poly-ionic:cysteine region and the target antigen sequence. Examples of leader sequences used herein include GSG (SEQ ID NO:6, MUC1 target antigen), AAY (SEQ ID NO:8, HPV 16 E7 CTL eptiope aa49-57), AAY (SEQ ID NO:18) P. falciparum circumsporozoite protein B-cell epitope, AAY (SEQ ID NOS:20-25, Dengue virus target antigen), and AAY (SEQ ID NO:26, SARS virus target antigen). One of ordinary skill in the art, through routine experimentation, can optimize the target antigen sequence and, in some cases, utilize a leader or linker sequence.

In alternative embodiments, the polypeptide target antigen is engineered to include a region of negatively charged amino acids that is capable of binding to the chimeric VLP that displays a region of positively charged amino acids present on a surface exposed region.

A. Tumor Antigens

Immunotherapy directed against cancer is a very active area of research and one approach is to induce immune responses to tumor-associated antigens by active vaccination. Accordingly, the compositions of the invention can include one or more tumor or cancer antigens. Tumor antigens include, but are not limited to, (a) polypeptide-containing tumor antigens, including polypeptides (which can range, for example, from about 8 to about 20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

Moreover, tumor antigens can be (a) full length molecules associated with cancer cells, (b) homologs and modified forms of the same, including molecules with deleted, added and/or substituted portions, (c) fragments of the same, and (d) extracts or lysates of tumor cells. Tumor antigens can also be provided in recombinant form. Tumor antigens include, for example, class I-restricted antigens recognized by $CD8^+$ lymphocytes or class II-restricted antigens recognized by $CD4^+$ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl $Le^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY—CO-1, RCAS1, SDCCAG16, TA-90 (Mac-2 binding protein\cyclophilin C-associated protein), TAAL6, TAG72, TLP, TPS, and the like.

B. Pathogen-Specific Antigens

The pathogen-specific antigens of the present invention can be derived from a virus, a bacterium a protozoan, or a fungus. Viral pathogens include, but are not limited to, RNA viruses; DNA viruses; adenovirdiae (e.g., mastadenovirus and aviadeno virus); herpesviridae (e.g., herpes simplex virus 1, herpes simplex virus 2, herpes simplex virus 5, and herpes simplex virus 6); leviviridae (e.g., levivirus, enterobacteria phase MS2, allolevirus); poxyiridae (e.g., chordopoxyirinae, parapoxvirus, avipoxvirus, capripoxvirus, leporipoxvirus, suipoxvirus, molluscipox virus, and entomopoxyirinae); papovaviridae (e.g., polyomavirus and papillomavirus); paramyxoviridae (e.g., paramyxovirus, parainfluenza virus 1, mobillivirus such as measles virus, rubulavirus (such as mumps virus)); pneumonoviridae (e.g., pneumovirus, human respiratory syncytial virus); metapneumovirus (e.g., avian pneumovirus and human metapneumo virus); picornaviridae (e.g., enterovirus, rhinovirus, hepatovirus such as human hepatitis A virus, cardiovirus, and apthovirus); reoviridae (e.g., orthoreo virus, orbivirus, rotavirus, cypo virus, fijivirus, phytoreo virus, and oryzavirus); retroviridae (e.g., mammalian type B retroviruses, mammalian type C retroviruses, avian type C retroviruses, type D retrovirus group, BLV-HTLV retroviruses, and lentivirus (such as human immunodeficiency virus 1 and human immunodeficiency virus 2, and spuma virus)); flaviviridae (e.g., hepatitis C virus); hepadnaviridae (e.g., hepatitis B virus); togaviridae (e.g., alphavirus (such as sindbis virus and rubivirus such as rubella virus); rhabdoviridae (e.g., vesiculovirus, lyssavirus, ephemera virus, cytorhabdovirus, and necleorhabdovirus); arenaviridae (e.g., arenavirus, lymphocytic choriomeningitis virus, Ippy virus, and lassa virus); and coronaviridae (e.g., coronavirus and torovirus); Cytomegalovirus (mononucleosis); Dengue virus (dengue fever, shock syndrome); Epstein-Barr virus (mononucleosis, Burkitt's lymphoma); Human T-cell lymphotropic virus type 1 (T-cell leukemia); Influenza A, B, and C (respiratory disease); Japanese encephalitis virus (pneumonia, encephalopathy); Poliovirus (paralysis); Rhinovirus (common cold); Rubella virus (fetal malformations); Vaccinia virus (generalized infection); Yellow fever virus (jaundice, renal and hepatic failure); and Varicella zoster virus (chickenpox).

Other embodiments of the present invention relate to a composition that is effective for generating an HIV-specific immune response. The composition can contain peptides derived from HIV early regulatory proteins including HIV Tat, Rev, and Nef (e.g., Nef-V3) proteins, or other HIV proteins such as Gag, Pol, Env, Vif, Vpr, and Vpu. In particular, peptide epitopes of these proteins are those that are capable of generating neutralizing antibodies. Numerous HIV CTL/CD8+ and T-helper/CD4+ epitopes are known in the art (HIV MOLECULAR IMMUNOLOGY, Korber, et al. (eds.), Los Alamos National Laboratory, Theoretical Biology and Biophysics, Los Alamos, N. Mex. (2006/2007)), and are contemplated for use in compositions effective for generating an HIV-specific immune response.

Bacterial pathogens include, without limitation, *Bacillus anthracis, Bordetella pertussis, Borrelia burgdorferi, Campylobacter jejuni, Chlamydia trachomatis, Clostridium botulinum, Clostridium tetani, Corynebacterium dipththeriae, Escherichia coli*, enterohemorrhagic *E. coli*, enterotoxigenic *E. coli, Haemophilus influenzae* type B and nontypable, *Helicobacter pylori, Legionella pneumophila, Listeria monocytogenes, Mycobacterium* spp., *Mycobacterium leprae, Mycobacterium tuberculosis, Neisseria gonorrhoeae, Neisseria meningitidis, Pneumococcus* spp., *Pseudomonas aeruginosa, Rickettsia, Salmonella* spp., *Shigella* spp., *Staphylococcus* spp., *Staphylococcus aureus, Streptococcus* spp., *Streptococcus pneumoniae, Streptococcus pyogenes, Streptococcus* B, Group A beta hemolytic *Streptococcus, Streptococcus mutans, Treponema pallidum, Vibrio cholerae*, and *Yersinia pestis*.

Pathogenic fungi include, but are not limited to, the genera *Aspergillus* (e.g., *Aspergillus fumigates*), *Blastomyces, Candida* (e.g., *Candida albicans*), *Coccidiodes, Cryptococcus, Histoplasma, Phycomyces, Tinea corporis, Tinea unguis, Sporothrix schenckii*, and *Pneumocystis carinii*. Pathogenic protozoa include, without limitation, *Giardia* spp. such as *Giardia lamblia*.

In a specific embodiment, the target antigen is MUC1. Human mucin-1 (MUC1) is aberrantly expressed on a wide range of ductal adenocarcinomas and has been intensively studied as a candidate cancer vaccine antigen. Li et al., 7 CURR. CANCER DRUG TARGETS 259-71 (2007); and Vlad et al., 82 ADV. IMMUNOL. 249-93 (2004). MUC1 is an integral membrane protein with an extracellular, transmembrane and cytoplasmic domain. Much of the extracellular domain of MUC1 consists of a tandemly repeating sequence of 20 amino acids. This core peptide (TRD) encodes B and T cell epitopes. In certain embodiments, chimeric papillomavirus VLP vaccines are formulated by coupling a 20 amino acid core MUC1 peptide with an N-terminal polyarginine cysteine tag to bovine papillomavirus VLPs with a polyglutamic acid cysteine sequence inserted into a surface exposed region of the L1 major capsid protein. In a specific embodiment, the target antigen comprises the sequence RRRRRRRRCGSGGVTSAPDTRPAPGSTAPPAH (SEQ ID NO: 6), wherein RRRRRRRRC (SEQ ID NO: 12) is the polycationic:cysteine region, GSG is a leader sequence, and GVTSAPDTRPAPGSTAPPAH (SEQ ID NO:7) is the 20 amino acid MUC1 peptide.

In yet another embodiment, the target antigen is human papillomavirus (HPV) 16 E7 CTL epitope aa49-57, a well-characterized model CTL epitope. In a specific embodiment, the target antigen sequence comprises CRRRRRRRRCAAYRAHYNIVTF (SEQ ID NO:8), wherein CRRRRRRRRC (SEQ ID NO: 13) is the polycationic:cysteine region, AAY is a leader sequence, and AAYRAHYNIVTF (SEQ ID NO: 14) is the E7 epitope.

In an alternative embodiment, the target antigen is *P. falciparum* circumsporozoite protein B-cell epitope. In a particular embodiment, the target antigen sequence comprises CRRRRRRRRCGNANPNVDPNANPNVDPNANPNVDPNANP (SEQ ID NO: 15), wherein CRRRRRRRR (SEQ ID NO: 16) is the polycationic: cysteine region, CG is the leader sequence and NANPNVDPNANPNVDPNAN-PNVDPNANP (SEQ ID NO: 17) is the antigen sequence. In another embodiment, the target antigen sequence comprises CRRRRRRRRCAAYSYVPSAEQI (SEQ ID NO:18), wherein CRRRRRRRRC (SEQ ID NO: 13) is the polycationic: cysteine region, AAY is the leader sequence, and SYVPSAEQI (SEQ ID NO:19) is the antigen sequence.

In other embodiments, the target antigen is a Dengue virus CD8 epitope. In particular embodiments, these antigens may comprise a CRRRRRRRRCAAY (SEQ ID NO:20) sequence at the N-terminus of the viral antigen sequence. Dengue viral antigen sequences can include, but are not limited to, YFSLGVLGM (SEQ ID NO:21), IGCYSQVN-PITLTAA (SEQ ID NO:22), YSQVNPITL (SEQ ID NO:23), RMLINRFTM (SEQ ID NO:24), and VAFLRFLTI (SEQ ID NO:25).

In a further embodiment, the target antigen is a severe acute respiratory syndrome (SARS) virus (e.g. sars coronavirus). The target antigen sequence may comprise CRRRRRRRRCAAYVNFNFNGL (SEQ ID NO:26), wherein CRRRRRRRRCAAY (SEQ ID NO:20) is the polycationic:cysteine sequence with the AAY leader sequence, and VNFNFNGL (SEQ ID NO:27) is the target antigen sequence.

The embodiments listed above are examples of target antigen constructs that can be conjugated to the chimeric papillomavirus VLPs of the present invention. It is within the scope of the invention to conjugate other target antigens to the vaccine platform described herein. Those of ordinary skill in the art, using techniques well known in the art, can produce VLP vaccine using any target antigen. For example, through routine experimentation, variations of target antigen sequence, polyionic:cysteine sequence, and/or leader sequences can be produced and tested to determine the optimal target antigen sequence to be used with the chimeric papillomavirus VLP vaccine platform.

III. Papillomavirus VLP Kits

Any of the compositions described herein may be included in a kit. In a non-limiting example, reagents for preparing a VLP and/or administering a VLP, or antibodies generated by vaccination with VLP can be included in a kit. The kit may further include reagents for assessing the activity of the VLP both in vitro and in vivo. The kits will thus comprise, in suitable container, a VLP composition. In certain aspects, the kit can include reagents and/or devices for administration, e.g., inhaler or nebulizer. It may also include one or more buffers, compounds, or devices for preparing the composition for administration.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention can also include a means for containing the containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container.

A kit may also include instructions for employing the kit components as well the use of any other reagent not included in the kit. Instructions may include variations that can be implemented. It is further contemplated that such reagents are embodiments of kits of the invention. Such kits, however, are not limited to the particular items identified above and may include any reagent used for the preparation and/or administration of a VLP vaccine of the invention. Among other uses, kits of the invention can be used in experimental applications. A skilled worker will recognize components of kits suitable for carrying out a method of the invention.

IV. Vaccine Compositions, Formulations, and Administration

Accordingly, particular embodiments of the methods of the present invention relate to the administration of effective amounts of compositions comprising papillomavirus VLPs. As used herein, the term "effective," means adequate to accomplish a desired, expected, or intended result. More particularly, an "effective amount" refers to an amount of a composition of the present invention (e.g., a papillomavirus VLP conjugated with a target antigen), either alone or in combination with another therapeutic agent (e.g., papillomavirus VLP comprising native L1 protein), necessary to provide the desired therapeutic effect, e.g., an amount that is effective to prevent, alleviate, treat or ameliorate symptoms of disease or prolong the survival of the subject being treated. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" or "prophylactically effective amount" in any individual case can be determined by one of ordinary skill in the art by reference to the pertinent texts and literature and/or by using routine experimentation. It is understood that reference to a pharmaceutical composition (e.g., a vaccine), its formulation, administration, and the like, can refer to, depending on the context, one or more of a papillomavirus VLP, a papillomavirus VLP conjugated with a target antigen, a papillomavirus VLP comprising native L1 protein, or mixtures of the foregoing including mixtures of VLPs conjugated with different target antigens.

The compositions of the present invention are in biologically compatible form suitable for administration in vivo for subjects. The pharmaceutical compositions further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the VLP is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can also include an effective amount of an additional adjuvant. As noted herein, papillomavirus VLPs have adjuvant properties. Suitable additional adjuvants include, but are not limited to, Freund's complete or incomplete, mineral gels such as aluminum hydroxide, surface active substances such as lysolecithin, pluronic polyols, polyanions, peptides, oil emulsions, dinitrophenol, and potentially useful human adjuvants such as *Bacille Calmette-Guerin, Carynebacterium parvum*, and non-toxic Cholera toxin.

The pharmaceutical compositions of the present invention can take the form of solutions, suspensions, emulsions, tablets, pills, capsules, powders, sustained-release formulations and the like. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a VLP of the present invention together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In particular embodiments, the compositions are administered at or near the target area, e.g., intratumoral injection.

In general, the pharmaceutical compositions may be used alone or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical composition and various therapeutic agents may be independently optimized and combined to achieve a synergistic result wherein the pathology is reduced more than it would be if either was used alone.

In particular, toxicity and therapeutic efficacy of the pharmaceutical composition may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

It would be readily apparent to one of ordinary skill in the art that the pharmaceutical compositions of the present invention can be combined with one or more therapeutic agents. In particular, the compositions of the present invention and other therapeutic agents can be administered simultaneously or sequentially by the same or different routes of administration. The determination of the identity and amount of therapeutic agent(s) for use in the methods of the present invention can be readily made by ordinarily skilled medical practitioners using standard techniques known in the art.

EXAMPLES

The following examples are put forth so as to provide those of ordinary skill in the art with a complete disclosure and description of how the biomarkers, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Generation of Recombinant Baculoviruses and Production of Bovine Papillomavirus (BPV) Virus-Like Particles (VLPs).

Figure 7:
FIG. 7 shows the bovine papillomavirus type-1 L1 protein 3-D structure with prediction of virion surface-exposed areas. The L1 monomer contains 6 loops (BC, CD, DE, EF, FG, HI), and 5 helices (H1-H5). In red are the 3 loops and the one helix that we replaced one at a time with a polyglutamic-cysteine epitope, and generated four chimeric constructs.

The entire open reading frame (ORF) of BPV L1 with a Kozak consensus and unique restrictions sites at each end (EcoR1/NotI) was artificially engineered by PCR-based gene synthesis (GeneScript, Piscataway, N.J.) and cloned in a pUC18 vector. The entire ORF was codon-modified for efficient expression in insect cells and contained insertion of a peptide with eight glutamic acid residues and a cysteine residue (E8C). Four synthetic L1 constructs were generated, each with a deletion of 9 wild type amino acids and insertion of the E8C peptide in the BC(aa 51-61), DE(aa 128-138), HI(aa 346-356) and H4(aa 412-422) loops, respectively (FIG. 7). The modified BPV L1 genes were subcloned between the EcoR1/NotI sites of the pORB baculovirus transfer vector (Orbigen, San Diego, Calif.). The transfer vectors were co-transfected with the Diamondback linear baculovirus DNA (Sigma-Aldrich Co., LLC, St. Louis, Mo.) in Spodoptera frugiperda sf9 cells using the Escort reagent (Sigma), as suggested by the manufacturer. Five days post-transfection, the recovered recombinant baculoviruses were further amplified by large scale infections of sf9 cells. Small scale infections to confirm expression of the modified L1 proteins were conducted with $2 \times 10^6$ Trichoplusia ni (High Five) cells (Invitrogen, Carlsbad, Calif.), growing in 6-well plates and infected with 20 µl of Baculovirus stocks. Seventy-two hours post-infection, the cells were lysed in 500 µl of RIPA buffer and the clarified lysates were subjected to Western blot analysis using a mAb against BPV L1 (Millipore, Temecula, Calif.). For large-scale production of VLPs, approximately $2 \times 10^9$ Trichoplusia ni (High Five) cells (Invitrogen, Carlsbad, Calif.) growing in spinner flasks were infected with 40 ml of a high-titer recombinant baculovirus stock in 500 ml of TNM-FH/10% FBS. After 96 h of incubation at 27° C., the cells were harvested, and collected by centrifugation at 2,000 rpm (Sorvall FH18/250 rotor) for 5 min. The cell pellets were resuspended in VLP extraction buffer (50 mM Tris pH=7, 150 mM NaCl, 2 mM $MgCl_2$, 1 mM $CaCl_2$), and the VLPs released by 3 freeze-thaw cycles. The lysates were clarified by centrifugation at 8,000×g for 30 min and further dilipidated by Freon extraction. The lysates were then loaded onto a cushion of 40% sucrose in VLP buffer and centrifuged in a SW-28 rotor at 27,000 rpm for 4 h at 4° C. The resulting pellets were resuspended in VLP buffer with 0.5 M NaCl, loaded on a discontinuous OptiPrep gradient (26%, 32%, 38%), and centrifuged in a SW-40 rotor at 37,000 rpm for 4 h at 16° C. The bands collected at the 26/32 (capsomeres) and 32/38 (capsids) interfaces were diluted 3-fold with VLP buffer, loaded on a discontinuous CsCl gradient (densities of 1.1, 1.2, 1.3, and 1.4 gr/ml), and centrifuged in a SW-40 rotor at 37,000 rpm for 4 h at 4° C. Capsids were collected from the bottom of the 1.3 phase, and capsomeres from the 1.2/1.3 interface and stored frozen at −70° C. A small fraction (<10% of the overall yield) of VLPs enter the 1.4 phase, and those were collected separately and were not used for the conjugation and immunization studies. These denser VLPs contain considerable more encapsidated nucleic acid. VLPs produced in insect cells may encapsidate some nucleic acid in a non-specific manner, especially after prolonged infections with recombinant Baculoviruses. The density of the light and heavy VLPs was 1.31 and 1.33 gr/ml, respectively. To estimate the amount of encapsidated nucleic acid, 200 µg of light and heavy WT and chimeric VLPs, purified from 4 different batches, were treated for 2 hrs at 42° C. with proteinase K in digestion buffer (20 mM Tris pH=8, 10 mM EDTA, 1% SDS), phenol/chloroform extracted, and the nucleic acid was precipitated by isopropanol. The pellet was resuspended in 10 µl of water and the concentration of nucleic acid (assumed to be composed by equal amounts of DNA and RNA) was estimated using a NanoDrop ND-1000 spectrophotometer.

Conjugation of BPV Polyanionic Particles with a Poly-Arginine MUC1 Peptide.

To construct a vaccine based on the epithelial antigen mucin-1 (MUC1), we synthesized the 20 amino acids long MUC1 tandem repeat peptide with N-terminal polyarginine, cysteine, and GSG spacer sequences (RRRRRRRRCGSGGVTSAPDTRPAPGSTAPPAH), R8CMUC1 (SEQ ID NO:6). The presence of the polyarginine moiety allows docking of the peptide to the polyanionic site (E8C) inserted in the various loops of the mutant L1 particles. Covalent cross-linking between the two cysteine residues should render this association irreversible under oxidizing conditions. For the conjugation reactions, purified L1 particles were dialyzed in conjugation buffer (20 mM Tris/HCl pH=7.5, 150 mM NaCl, 5% glycerol, 0.5 mM $CaCl_2$) and then the peptide and the oxidizing reagents were added, allowing the reaction to proceed for 16 hrs at 4 C. Initially, a 4:1 ratio of oxidized (GSSG):reduced (GSH) glutathione was used in the conjugation reaction (2 mM GSSG, 0.5 mM GSH) and the highest possible molar ratio of peptide/assembled L1 protein that would not result in aggregation was estimated. The ratio of GSSG:GSH was then further optimized by testing ratios from 8:1-2:1. Titration experiments were also conducted to evaluate conjugation efficiency under variable ionic strength (100-400 mM NaCl). At the end of the incubation, the reaction mixtures were applied to a size-exclusion column (Sephadex G-100, Pharmacia, volume 20 ml, flow rate 1 ml/min, 10 mM Tris/HCl (pH=7.4), 150 mM NaCl, 0.5 mM $CaCl_2$) to remove unconjugated peptide and exchange buffer. Conjugated particles that eluted in the void volume were identified by the presence of the L1 protein on SDS-PAGE. The conjugated particles were analyzed by electron microscopy. Conjugation efficiency was estimated using an ELISA assay with an anti-MUC1 mAb (BD Pharmingen, San Diego, Calif.). Free R8c-MUC1 peptide was used for generating a standard curve.

Electron Microscopy and Immunogold Labeling.

To facilitate direct visualization of the constructs, an aliquot of diluted particles was placed on 300-mesh formvar/carbon-coated copper grids (Electron Microscopy Sciences, Hatfield, Pa.), negatively stained with 2% phosphotungstic acid (pH=7.0) and examined by transmission electron microscopy (TEM). For immunogold labeling, an aliquot of either conjugated or unconjugated (negative control) diluted particles was adsorbed onto 300-mesh formvar/carbon-coated nickel grids and blocked with 3% BSA in TBS for 2 hrs. The anti-MUC1 monoclonal antibody was diluted 1:25 in 1% BSA/TBS and adsorbed to the grid for 1 hr at room temperature. Bound IgG was detected by incubation for 1 h at room temperature with colloidal-gold-conjugated (6 nm) goat anti mouse IgG (Electron Microscopy Sciences, Hatfield, Pa.) diluted 1/50 in blocking solution. The grids were negatively stained with 1% sodium silicotungstate (pH=6.5) and examined by TEM.

Cell Lines and Mice.

Cells were cultured in complete DMEM containing 10% FBS, penicillin and streptomycin, L-glutamine, sodium pyruvate, nonessential amino acids, HEPES buffer and β-mercaptoethanol. The previously described MUC1-specific T cell hybridoma line VF5 was the source of the TCR for generation of VFT mice. Vlad et al., 196 J. EXP. MED. 1435-46 (2002). VFT mice transgenic for a T cell receptor (TCR) specific for an MHC Class II-restricted epitope, a 12 amino acid peptide GVTSAPDTRPAP (SEQ ID NO:28) derived from the epithelial cell mucin1, were used as source of antigen specific T cells. Alajez et al., 105 BLOOD 4583-89 (2005). MUC1-Tg mice (6-8 wk old) on a C57BL/6 background were purchased from Dr. S. Gendler (Mayo Clinic, Scottsdale, Ariz.), and conventional C57BL/6 mice (wild type—WT) were obtained from The Jackson Laboratory (Bar Harbor, Me.). All mice were maintained in a standard pathogen-free environment at the University of Pittsburgh Cancer Institute and treated in accordance with the guidelines set by the Institutional Animal Care and Use Committee of the University of Pittsburgh.

Generation of Bone Marrow Derived Dendritic Cells (BMDC) and Maturation Assays.

BMDC were generated as described previously. Turner et al., 178 J. IMMUNOL. 2787-93 (2007). Briefly, bone marrow (BM) cells removed from the tibiae and femurs of C57BL/6 mice were cultured in complete AIM V (cAIM V) medium containing penicillin and streptomycin, L-glutamine, sodium pyruvate, nonessential amino acids and HEPES buffer (without the addition of 2-ME, a reducing agent, in order to prevent destruction of the dicysteine bond between the conjugated R8c-MUC1 peptide and the E8C core of the chimeric VLPs) containing 20 ng/ml each of GMCSF. Cells were fed on days 2, 4, and 6 by adding 5 ml of cAIM V containing 20 ng/ml GMCSF. On day 7 of culture, immature DC were harvested and loaded with the various BPV chimeric particles or soluble antigen for 24 h. Following culture, cell supernatants were harvested for the detection of a T cell stimulatory cytokine, IL-12, and the cells were stained for the upregulation of costimulatory and antigen presenting molecules. Briefly, DC were stained with allophycocyanine-conjugated anti-CD11c together with Fluorescein isothiocyanate-conjugated anti-CD40, anti-CD80, anti-CD86 or anti-MHC II antibodies (PharMingen, San Diego, Calif.). The cells were blocked with Fc block prior to staining to prevent nonspecific binding of antibodies. Flow cytometry was performed using a FACSLSRII and the data analyzed with FACSDiva software (BD Pharmingen, San Diego, Calif.). The percent of BMDC expressing high levels of costimulatory molecules was determined by gating on the cells that were positive in untreated cells.

Antigen Presentation and T-Cell Stimulation Assays.

Spleens from VFT mice were harvested and processed to single cell suspension. Following lysis of RBC, 1, 5, or 25 μg of chimeric MUC-conjugated VLPs were added to total splenocytes in cAIM V media (without the addition of β-ME). Splenocytes were also treated with increasing amounts (10, 50, and 250 ng) of free MUC1 20-mer peptide. Based on the experiments contacted to determine R8c-MUC1 conjugation efficiency on chimeric VLPs, these are the amounts of MUC1 present on 1, 5 and 25 μg of conjugated chimeric VLPs. Following 3 days of culture in cAIM V, supernatants were harvested to determine IFNγ production as a measure of antigen-specific T cell stimulation, using ELISA (BD Pharmingen, San Diego, Calif.). The cells were then re-cultured in cAIM V containing 1 μCi/100 μl tritiated thymidine for 24 h to measure proliferation. Twenty-four hours following culture, cells were lysed using a semiautomatic cell harvestor (Skatron Instruments, Sterling, Va.) and the amount of incorporated tritiated thymidine measured using a β-counter.

Vaccination and Tumor Challenge.

MUC1-Tg mice were immunized subcutaneously (s.c.) in the right flank with 5 μg of BPVHI-E8c-MUC1 in 100 μl of PBS (vaccine) or 5 μg of BPV-HI-E8c (vector control) or PBS (negative control). Two more boosts were administered similarly at 2-wk intervals. Two weeks following the final boost, mice were challenged with $5 \times 10^4$ RMA-MUC1 cells s.c. also in the right flank. RMA-MUC1 cells are a T cell lymphoma line on a C57BL6 background that was transfected by electroporation with the pR/CMV-MUC1 plasmid containing full-length MUC1 cDNA with 42 tandem repeats. Soares et al., 166 J. IMMUNOL. 6555-63 (2001). Tumor growth and general condition of the mice were monitored every 2-3 days. Tumor size was recorded using vernier calipers and mice were sacrificed according to the University of Pittsburgh IUCAC guidelines, when the tumor reached a size of 2 cm.

T-Cell Activation Assays.

Spleen cells were prepared by mechanical disruption and RBC lysis using red blood cell lysing buffer (Sigma Aldrich, St. Louis, Mo.). The splenocytes were then stained with Carboxyfluorescein succinimidyl ester (CFSE) as well as antibodies to CD4 and CD8 (BD Pharmingen, San Diego, Calif.) to evaluate for proliferation and stimulated in vitro with BPVHI-E8c (5 μg/ml) or BPV-HI-E8c-MUC1 (5 μg/ml) or concanavalin A (ConA −5 μg/ml) for 1 or 5 days. On day 1, cells were stained with anti-CD8 and anti-CD107a antibodies (BD Pharmingen, San Diego, Calif.) and evaluated for lytic capabilities by measurement of CD107a. Devêvre et al., 311 J. IMMUNOL. METHODS 31-46 (2006). On day 5, cell culture supernatants were harvested for measurement of IFNγ production by ELISA (BD Pharmingen, San Diego, Calif.) and cell proliferation was assessed using flow cytometry.

MUC1-Specific ELISA.

Fourteen days after the last boost, blood samples were collected by tail bleeding, and the serum was tested for the presence of MUC1-specific antibodies with a MUC1-specific ELISA. Briefly, 96-well Immulon 4 plates (Dynatech, Chantilly, Va.) were coated at room temperature overnight with 10 μg/ml of 100-aa MUC1 peptide in PBS. The plates were washed three times with PBS and incubated with 1:40 dilution of the immune serum for 2 h at room temperature (RT). After three washes with PBS/0.1% Tween 20, the plates were incubated with polyclonal goat anti-mouse-IgG HRP-conjugated secondary Abs (Sigma, St. Louis, Mo.) for 1 h at RT. The plates were washed three times with PBS/0.1% Tween 20 and then incubated with the TMB substrate (BD Biosciences, San Diego, Calif.) for 30 min. The reaction was stopped with 2.5 M sulfuric acid, and the absorbance was measured at 450 nm.

Statistical Analysis.

The statistical significance for two group comparisons was calculated by a paired, two-tailed t test. Multiple group comparisons were performed using one-way analysis of variance and Fisher's least significant difference. Values of p<0.05 were considered significant.

Example 1

Production of Polyanionic BPV Chimeric VLPs

In the present study, recombinant baculoviruses expressing chimeric BPV L1 protein with insertion of a polyglutamic cysteine peptide and replacement of native residues in the BC, DE and HI loops and the H4 helix respectively were generated. Western blot analyses of lysates from Hi5 cells infected with the baculoviruses revealed different patterns of expression for the L1 protein (FIG. 1A). The BPV-BC-E8c baculovirus construct displayed extensive degradation of L1; the H4 had moderate degradation, while degradation of L1 in the BPVDE-E8c and BPV-HI-E8c was minimal. Large scale infections of insect cells with the four recombinant baculoviruses, and subsequent purification in step gradients revealed different banding patterns for the four constructs. For the BPV-BC-E8c preparation, no L1 reactivity (by Western blot) was observed anywhere in the gradient, suggesting no particle assembly. The majority of the L1 reactivity in the BPV-H4-E8c preparation was detected in fractions with lower density, while, the majority of BPV-HI-E8c was detected in fractions with higher density. The BPV-DE-E8c had L1 reactivity in fractions of both low and heavy density with no obvious peak, indicating the presence of several assembled forms in this preparation. No L1 degradation products were observed in the purified preparations (FIG. 1B). Analysis of the 3 purified preparations by electron microscope confirmed that the BPV-HI-E8c was composed primarily of fully assembled VLPs with approximate size of 45-55 nm (FIG. 1C), BPV-H4-E8c contained capsomeres of approximately 4-5 nm (FIG. 1D), and the BPV-DEE8c was partially assembled VLPs (FIG. 1E). As described above, fully formed VLPs were recovered in two predominant fractions. The light fraction, with density of 1.31 gr/ml, is the predominant one, and that was what was used for immunizations. The amount of nucleic acid present in this fraction was 7.8±1.5 ng per µg of VLP. Given that mice are immunized with 5 µg of VLP, it is not expected that this amount of nucleic acid is enough to serve as an adjuvant. Even CpG oligonucleotides, which are designed for increased immunogenicity, are used at doses of several micrograms. The denser fraction, with density of about 1.33 gr/ml, contains 56±5 ng per µg of VLP. These VLPs are further evaluated for increased immunogenicity.

Example 2

Conjugation of Purified VLPs and Capsomeres with the R8C-MUC1 Peptide

Figure 2:
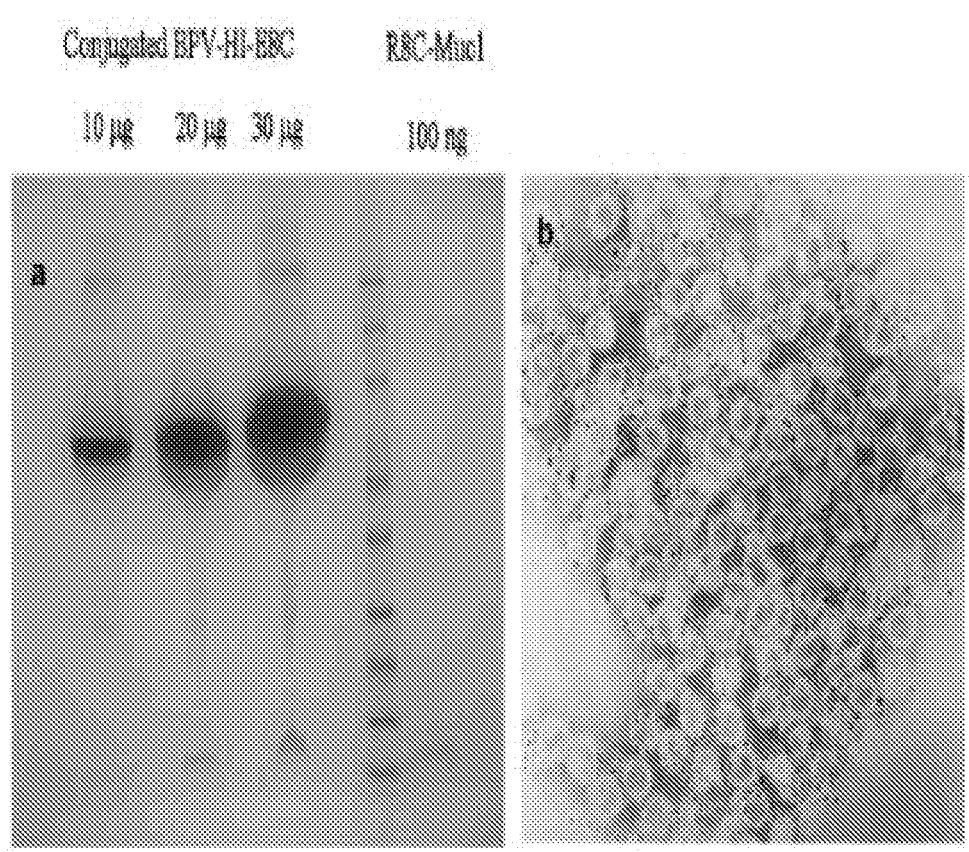
FIG. 2 shows the quantitative and qualitative assessment of MUC1 peptide conjugation on chimeric VLPs.
Figure 8A:
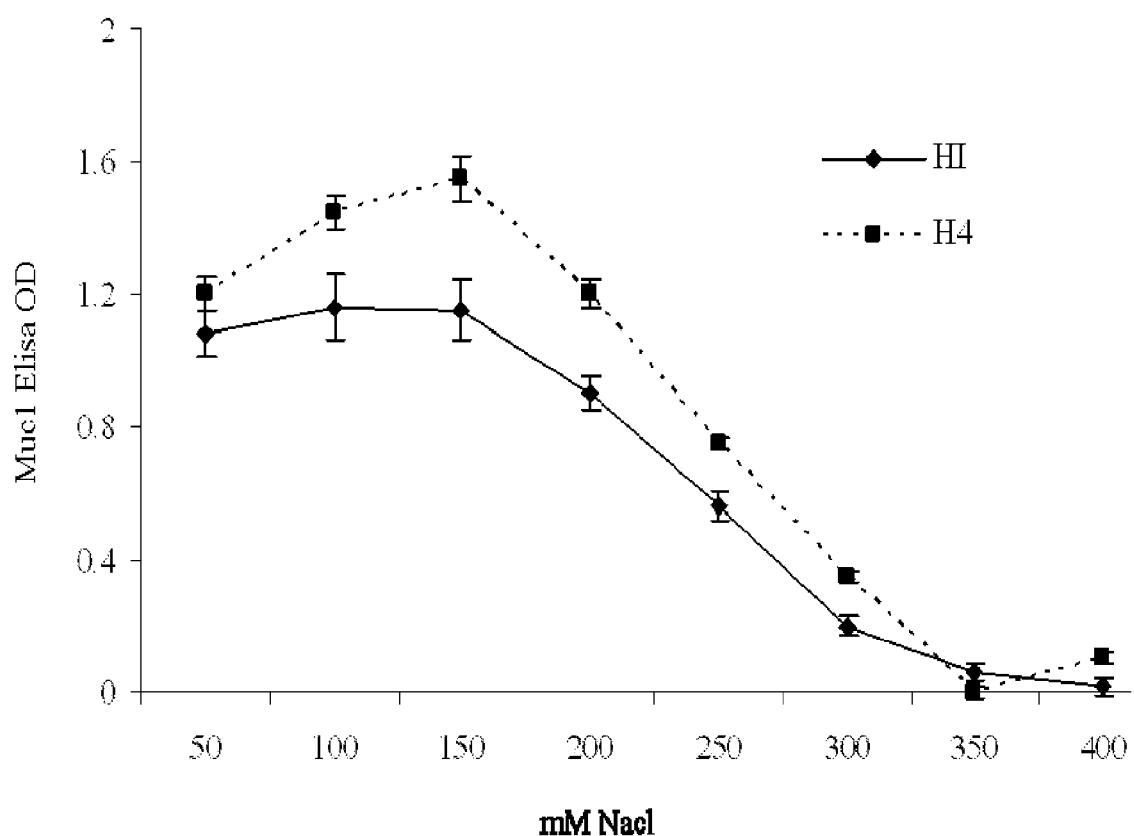
FIG. 8A shows the effect of ionic strength on conjugation efficiency of BPV-HI-E8c, and BPV-H4-E8c with the polyarginine MUC1 peptide R8c-MUC1. The conjugation efficiency is presented as the amount of MUC1 reactivity (OD) in ELISA assays where the plates were coated with conjugated particle.
Figures 8B, 8C:
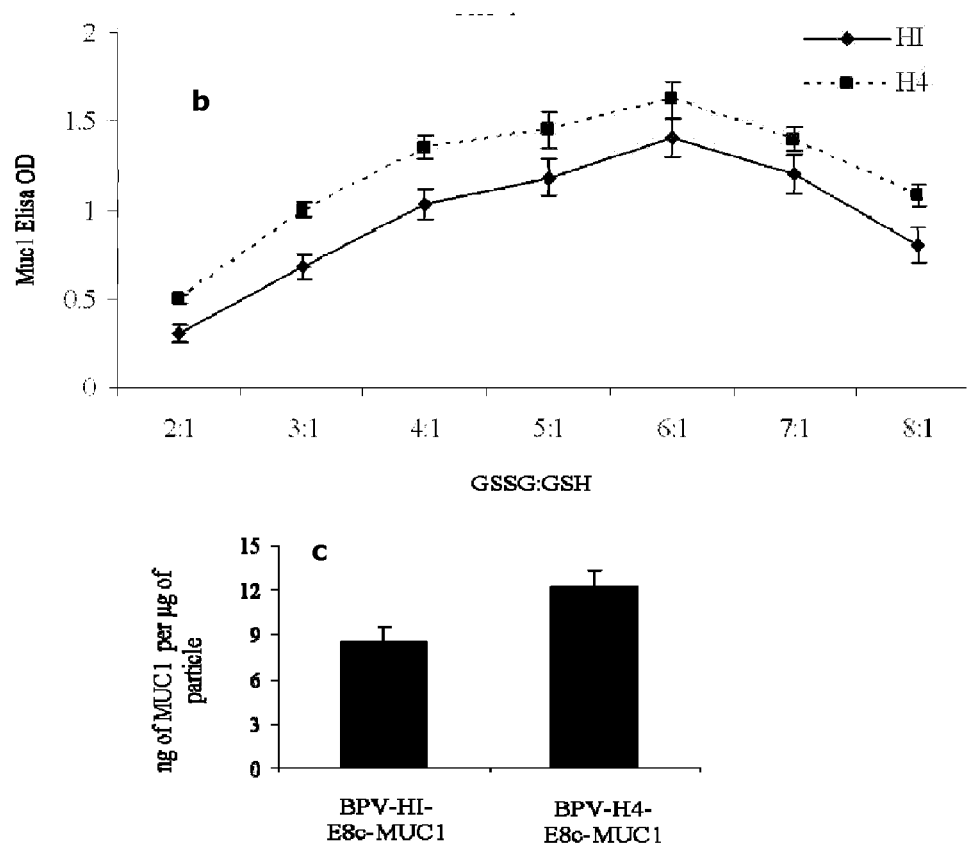
FIG. 8B shows the effect of the ratio of oxidized (GSSG) to reduced glutathione (GSH) on conjugation efficiency of BPV-HI-E8c, and BPV-H4-E8c with the polyarginine MUC1 peptide R8c-MUC1.
FIG. 8C shows the quantitative assessment of conjugation efficiency in the BPV-HI-E8c, and BPV-H4-E8c with the polyarginine MUC1 peptide R8c-MUC1. The MUC1 reactivity of conjugated particles in ELISA assays were compared to the reactivity of various amounts of free R8c-MUC1 peptide.

Based on SDS-PAGE and electron microscopy, particle preparations were more than 90% pure. Therefore, the amount of particles (in µg of protein) was assumed to represent the amount of L1 protein. L1 is composed of 495 aa with a theoretical MW of 55.56 kd, while the 32-mer peptide has a theoretical MW of 3.44 kd. A 16:1 L1/peptide mass ratio was therefore assumed to represent a 1:1 molar ratio. A peptide/L1 molar ratio of greater than 2:1 resulted in substantial aggregation of particles, and subsequent conjugation reactions utilized that ratio which is equivalent to 1 µg of peptide for every 8 µg of purified particles. The effect of ionic strength and the ratio of oxidized/reduced glutathione (GSSG:GSH) in the conjugation reaction was also optimized. The conjugation efficiency, as estimated by the amount of MUC1 reactivity in ELISA assays, was substantially inhibited at NaCl concentrations greater than 150 mM, and a GSSG:GSH ratio of 5:1 was found to be optimal without affecting the morphology of particles and/or inducing aggregation (FIGS. 8A and 8B). Based on quantitative ELISA estimates, each µg of HI VLPs had 8.5±1.0 ng of conjugated peptide (14% conjugation efficiency), while each µg of H4 capsomeres had 12.3±1.1 ng of conjugated peptide (20% conjugation efficiency) (FIG. 8C). To further evaluate this estimate, various amounts of conjugated BPV-HI-E8c VLPs (30, 20, 10 µg) and free R8c-MUC1 (100 ng) were subjected to SDS-PAGE and Coomasie brilliant blue staining (FIG. 2A). In comparison with the intensity of staining of 100 ng of free R8c-MUC1, 10 µg of conjugated BPV-HI-E8c VLPs appear to contain-60-80 ng of peptide, thus confirming our estimations based on the ELISA assays. Furthermore, immunogold labeling an anti-MUC1 mAb verified the integrity of the VLPs and successful attachment of the MUC1 peptide (FIG. 2B). The conjugation efficiency of VLPs in the present study is higher than what has been previously reported for conjugation of antibody fragments in polyomavirus VLPs using similar strategy (11). The reason for increased conjugation efficiency is probably due to the smaller peptide and reduced steric hydrance (MUC1-32mer vs. Fab fragment).

Example 3

Differential Ability of MUC1-Conjugated Chimeric VLPs and Capsomeres to Activate Dendritic Cells (DC)

Figure 3:
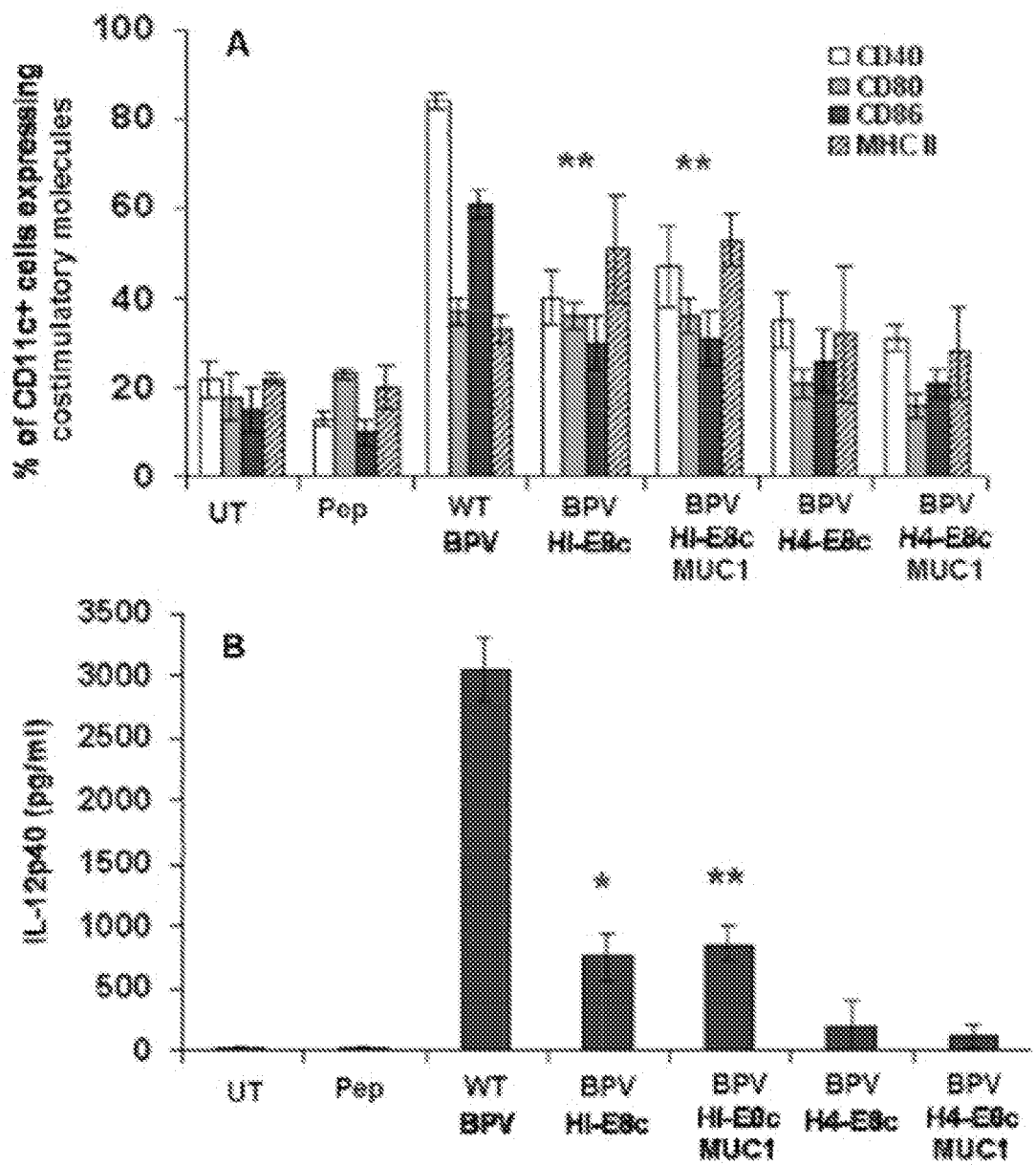
FIG. 3 relates to BMDC activation following uptake of BPV and BPV-MUC1.
Figure 9:
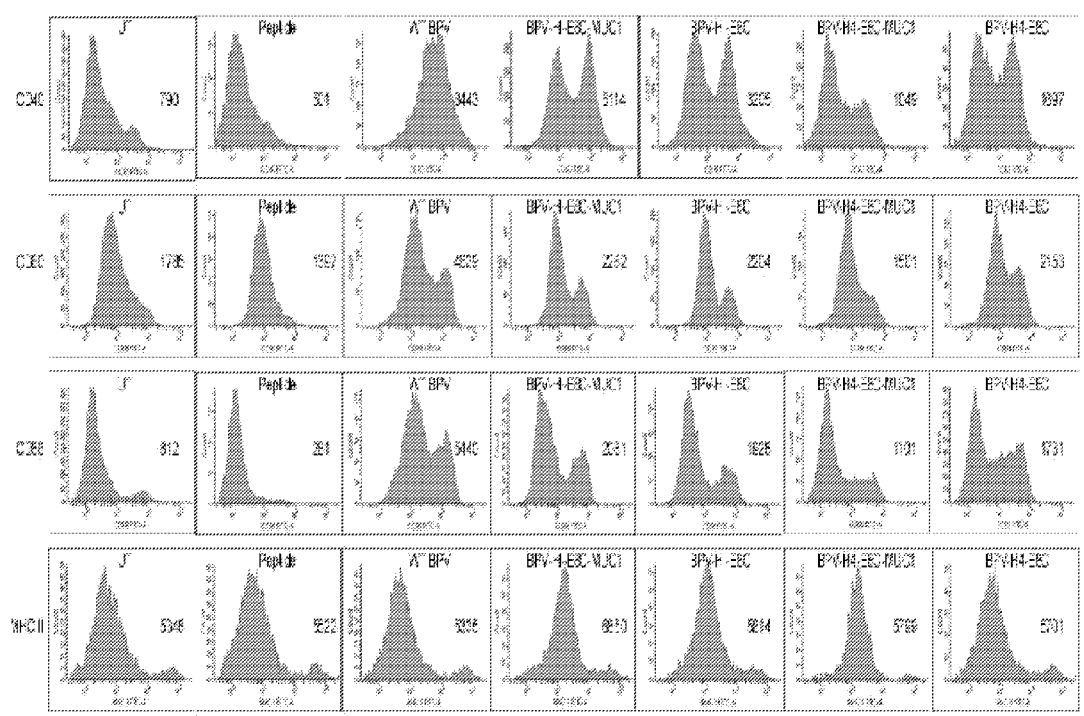
In FIG. 9, BMDC were loaded with various BPV constructs (WT BPV, BPV-HI-E8c-MUC1, BPV-HI-E8c; BPV-H4-E8c-MUC1, BPV-H4-E8c) for 24 h were stained for standard DC maturation markers CD40, CD80, CD86 and MHC class II and analyzed by flow cytometry. Shown here are representative histograms for each of the costimulatory molecules analyzed: DC alone (untreated—UT), MUC1 peptide (250 ng-GVTSAPDTRPAPGSTAPPAH) (SEQ ID NO:7).

Native papillomavirus VLPs are known to activate DC. To determine whether chimeric VLPs and capsomeres retain this property, bone marrow-derived DC were exposed to the chimeric constructs and assessed for increased expression of several DC activation and maturation markers. Immature BMDC were left untreated, or loaded with 250 ng of the 20aa MUC1 free peptide, 5 µg of the various BPV particles without MUC1 or conjugated to MUC1, and wild type BPV. Twenty-four hours later, DC were stained with a monoclonal antibody specific for CD11c, a DC specific marker, and with antibodies specific for activation/maturation markers CD40, CD86, CD80 and MHC Class II and analyzed by flow cytometry. Robust upregulation of costimulatory molecules on DC was seen following treatment with WT BPV (FIG. 3A). The BPV-HI-E8c (unconjugated) and BPV-HI-E8c-MUC1 (conjugated) VLPs retained the ability to significantly (unconjugated vs. mock: p=0.000195; conjugated vs. mock: p=0.0000035) increase the expression of activation and maturation molecules on DC (FIG. 3A and FIG. 9). The BPV-H4-E8c capsomeres, however, induced an increase in some activation markers but the response was lower than that of fully formed VLPs. Induction of IL-12 production was also tested for, which is an important cytokine that promotes generation of T-helper 1 responses. Goriely et al., 13 CURR. OPIN. ORGAN TRANPLANT. 4-9 (2008). Extending the findings with the cell surface maturation markers, only DC exposed to either WT BPV, conjugated or unconjugated BPV-HI-E8c VLPs produced significant (unconjugated vs. mock: p=0.0236; conjugated vs. mock: p=0.00346684) levels of IL-12p40 (FIG. 3B). It is important to note that even though there was a significant increase in IL-12 production following treatment with fully formed VLPs, it was lower than the amount produced following treatment with WT BPV. This could be due to the modifications made in the VLP to accommodate the MUC1 peptide. Therefore, subsequent in vivo experiments to evaluate the immunogenicity and efficacy were conducted with chimeric MUC-conjugated fully formed VLPs.

Example 4

Figure 4:
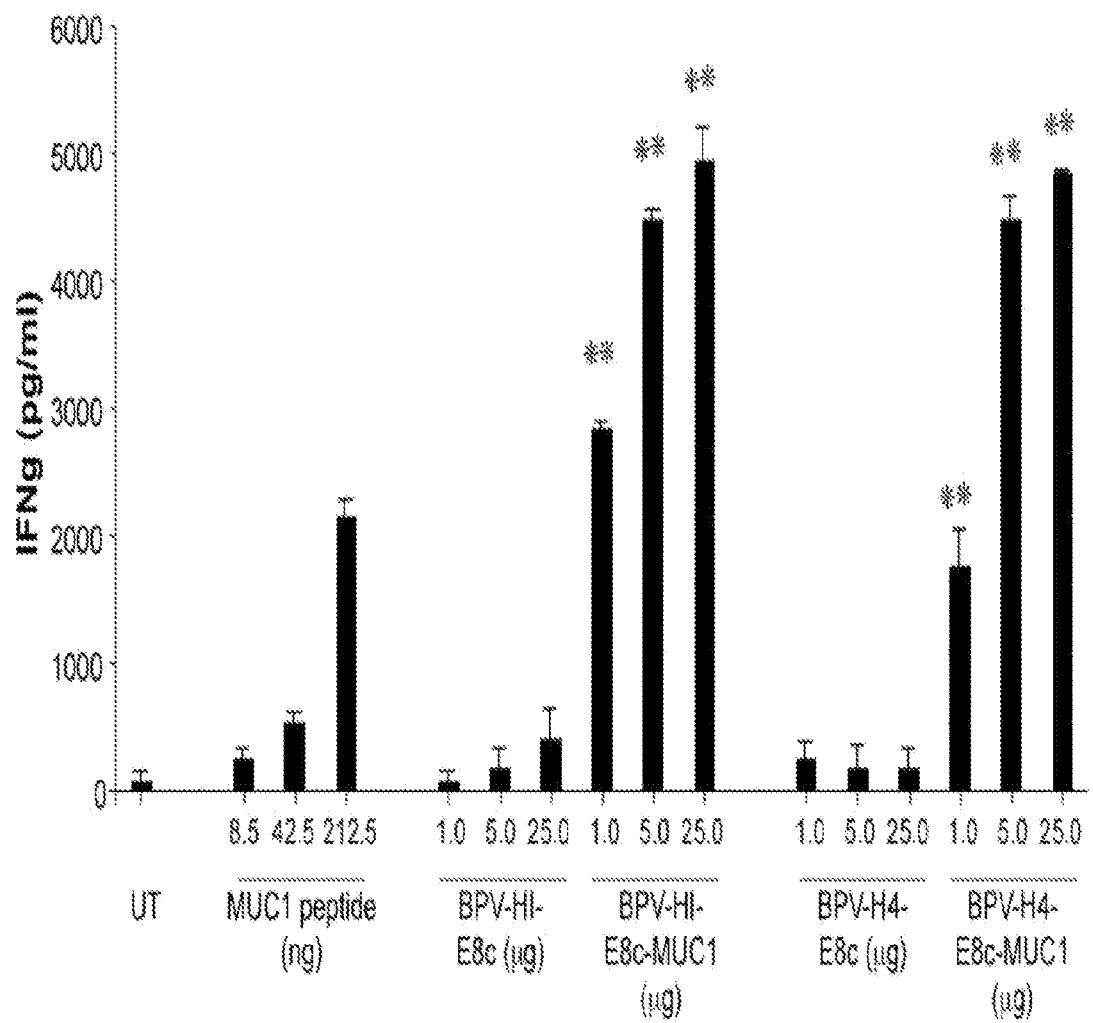
FIG. 4 demonstrates that MUC1 conjugated to chimeric BPV VLPs can be cross-presented to primary, naïve MUC1-specific T cells. The graph shows IFNγ production following mock-treatment (untreated), addition of MUC1 peptide (10, 50, 250 ng), or treatment with unconjugated (BPV-HI-E8c) and MUC1-conjugated (BPV-HI-E8c-MUC1) chimeric VLPs (1, 5, 25 μg). p values were calculated against peptide alone for each concentration shown. **p<0.01.

MUC1 Conjugated on Chimeric BPV Particles can be Processed and Presented to Primary MUC1-Specific T-Cells In order to induce adaptive, antigen-specific immunity, APC need to be able to uptake and also process the correct peptides, when antigen is delivered by various vehicles, such as chimeric VLPs. To test the ability of the MUC1-conjugated chimeric BPV VLPs to activate T cells in the context of many different APC, splenocytes from MUC1-specific TCR transgenic VFT mice that provide the APC and also a high frequency of naive MUC1-specific T cells were used. Splenocytes were cultured for three days with various amounts of soluble MUC1 peptide or with chimeric MUC1-conjugated or unconjugated VLPs. Supernatant was harvested for evaluation of IFNγ production, and the cells were cultured for an additional day in media containing [3H]-thymidine to evaluate T cell proliferation. Following culture with the MUC1 decorated chimeric BPV particles, but not with the unconjugated BPV particles, MUC1-specific TCR transgenic splenocytes underwent proliferation (data not shown) and secreted significant ($p<0.01$ for both conjugated VLP and capsomeres against peptide alone for each concentration shown) amounts of IFNγ (FIG. 4). The response was significantly higher when MUC1 was delivered conjugated to VLPs than as a free peptide.

Example 5

BPV-HI-E8c-MUC1 Vaccine Activates Primarily CD8+ T-Cells

Figure 5A:
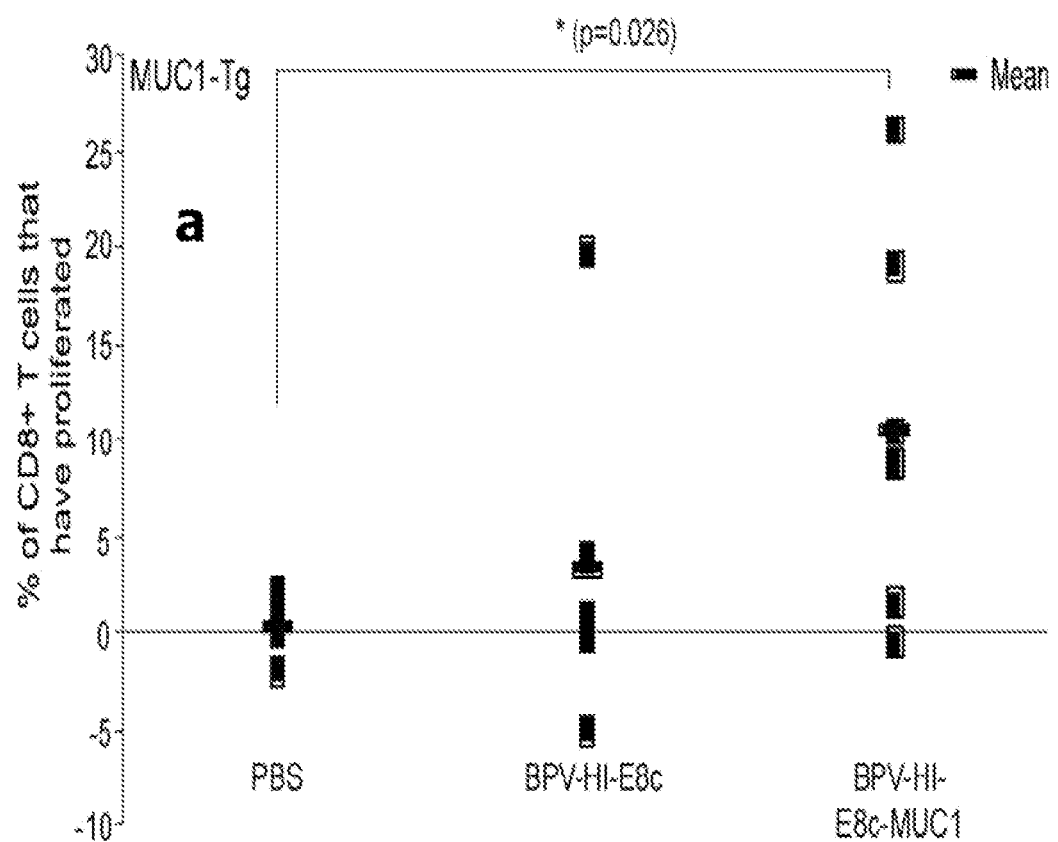
FIG. 5 shows T-cell activation in MUC1-Tg mice. Proliferation of MUC1-specific CD8+ T cells (FIG. 5A) and CD4+ T cells (FIG. 5B) following in vitro culture of CFSE-labeled splenocytes for 5 days with the immunizing antigens as indicated.
As shown in FIG. 5C, on day 5, supernatants were harvested and measured for the presence of IFNγ using ELISA. The results shown are for individual mice. *Values of p<0.05 were considered significant. n=6-7 mice per group.
Figure 5B:
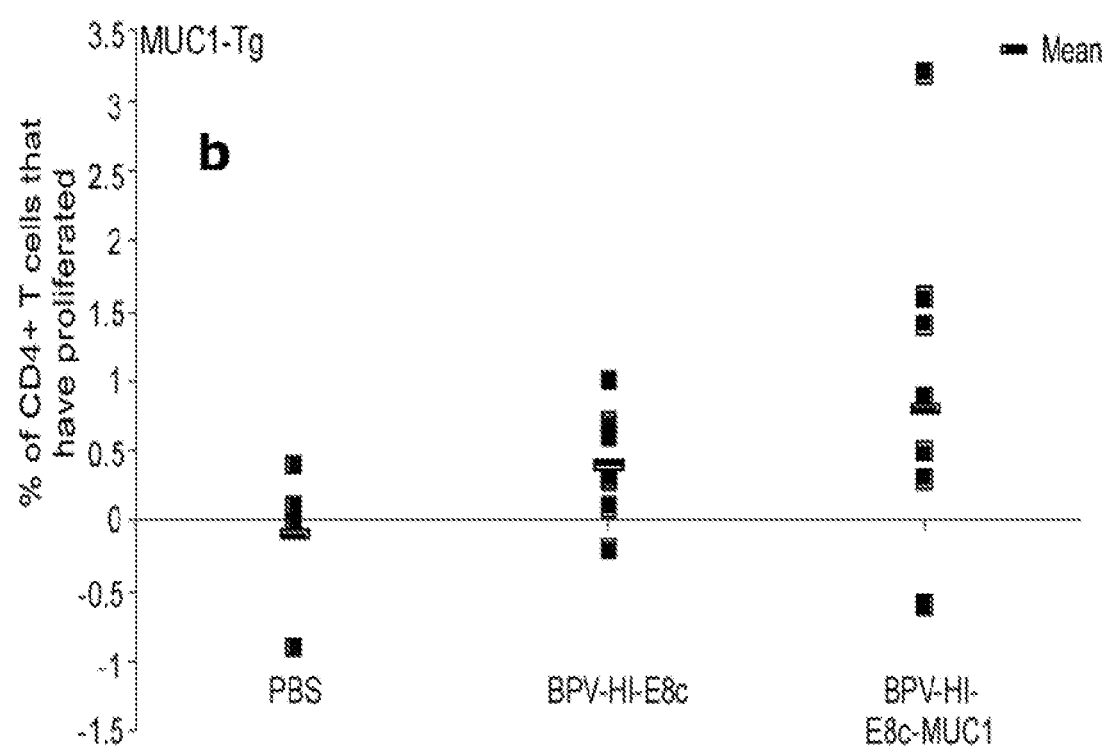
Figure 5C:
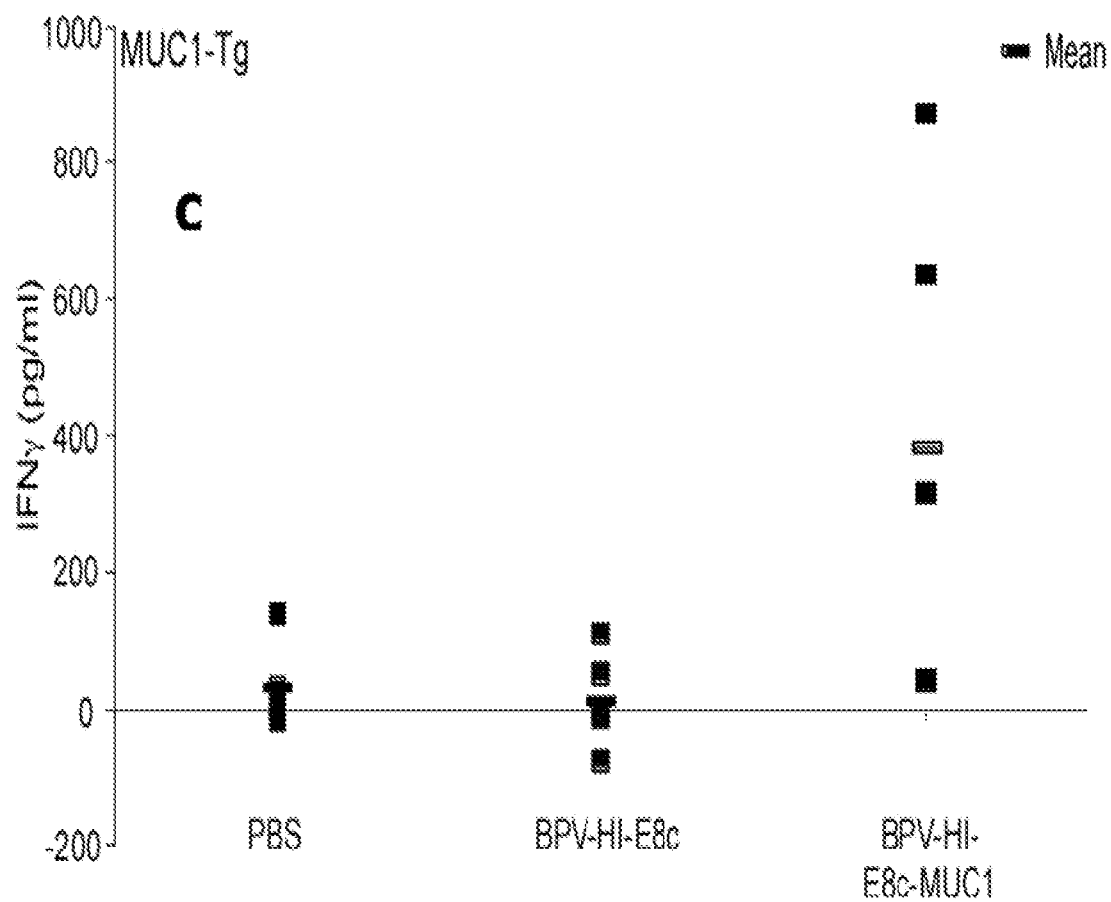

MUC1-Tg mice contain human MUC1 that is both spatially and temporally expressed similarly to that in humans and serves as a model to assess the ability of the vaccine to overcome potential tolerance in these mice to this endogenous tumor-associated antigen. Thus, MUC1-Tg mice were immunized three times, 2 weeks apart with 5 g per dose, each of vector alone (BPV-HI-E8c) or the vaccine (BPV-HI-E8c-MUC1), or PBS (controls). Two weeks following the last booster, mice were injected with RMA-MUC1 tumor cells to mimic tumor development in humans in the presence of pre-existing immunity. Approximately 11 days following vaccination, some mice from each group were sacrificed and spleens were harvested to evaluate anti-MUC1 immunity. Splenoctyes were CFSE-labeled and cultured in the presence of BPV-HI-E8c-MUC1 or BPV-HI-E8c to further expand the number of MUC1-specific T cells. Five days post culture, supernatant was harvested to evaluate IFNγ, and cell proliferation was measured using CFSE dilution detected by flow cytometry. A significant increase in proliferation of MUC1-specific CD8+ T cells was seen in MUC1-Tg mice vaccinated with BPV-HI-E8c-MUC1 as compared to PBS treated controls and vector control BPV-HI-E8c (FIG. 5A). However, only a slight increase in specific CD4+ T cell proliferation was detected (FIG. 5B). Further evaluation of the functional capacity of the splenoctyes showed a trend ($p=0.058$) towards the production of increased levels of an important immunomodulatory cytokine, IFNγ, by bulk splenocytes from mice that were vaccinated compared to controls treated with vector or PBS (FIG. 5C). Based on the proliferation data, it is hypothesized that the activated CD8+ T cells were the major producers of IFNγ. Increased activation of CD8+ T cells in MUC1-Tg mice immunized with the MUC1 vaccine was further seen in the expression of lysosome associated markers, CD107a (LAMP-1) (data not shown). Appearance of this marker has been shown to be indicative of cytolytic activity of CTL. Aktas et al., 254 CELL. IMMUNOL. 149-54 (2009).

Figure 10:
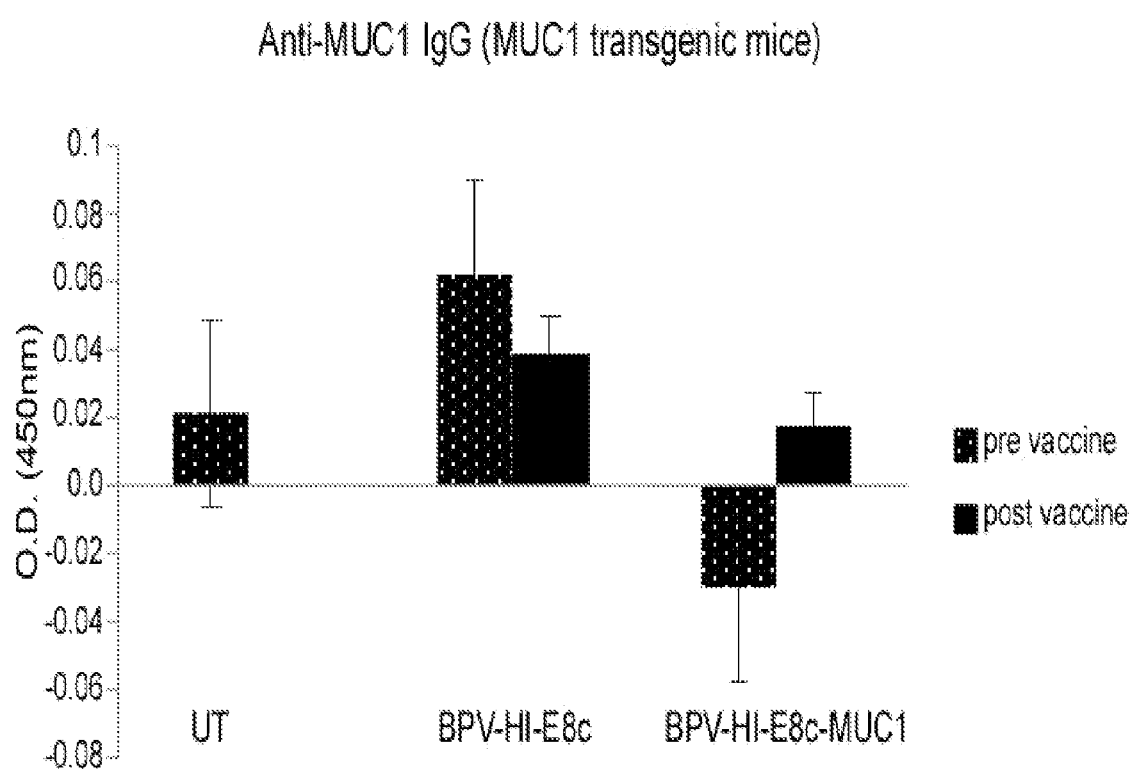
In FIG. 10, mice were vaccinated three times, two weeks apart, with vector control (BPV-HI-E8c), vaccine (BPV-HI-E8c-MUC1) or left untreated (UT). Blood was collected from the mice prior to vaccination (pre vaccine) and following final treatment (post vaccine). Serum (1:40 dilution) was then analyzed to determine the presence of antibodies to MUC1. Four mice were analyzed in the untreated group and 9 mice in the vector and vaccine groups.
Figure 11:
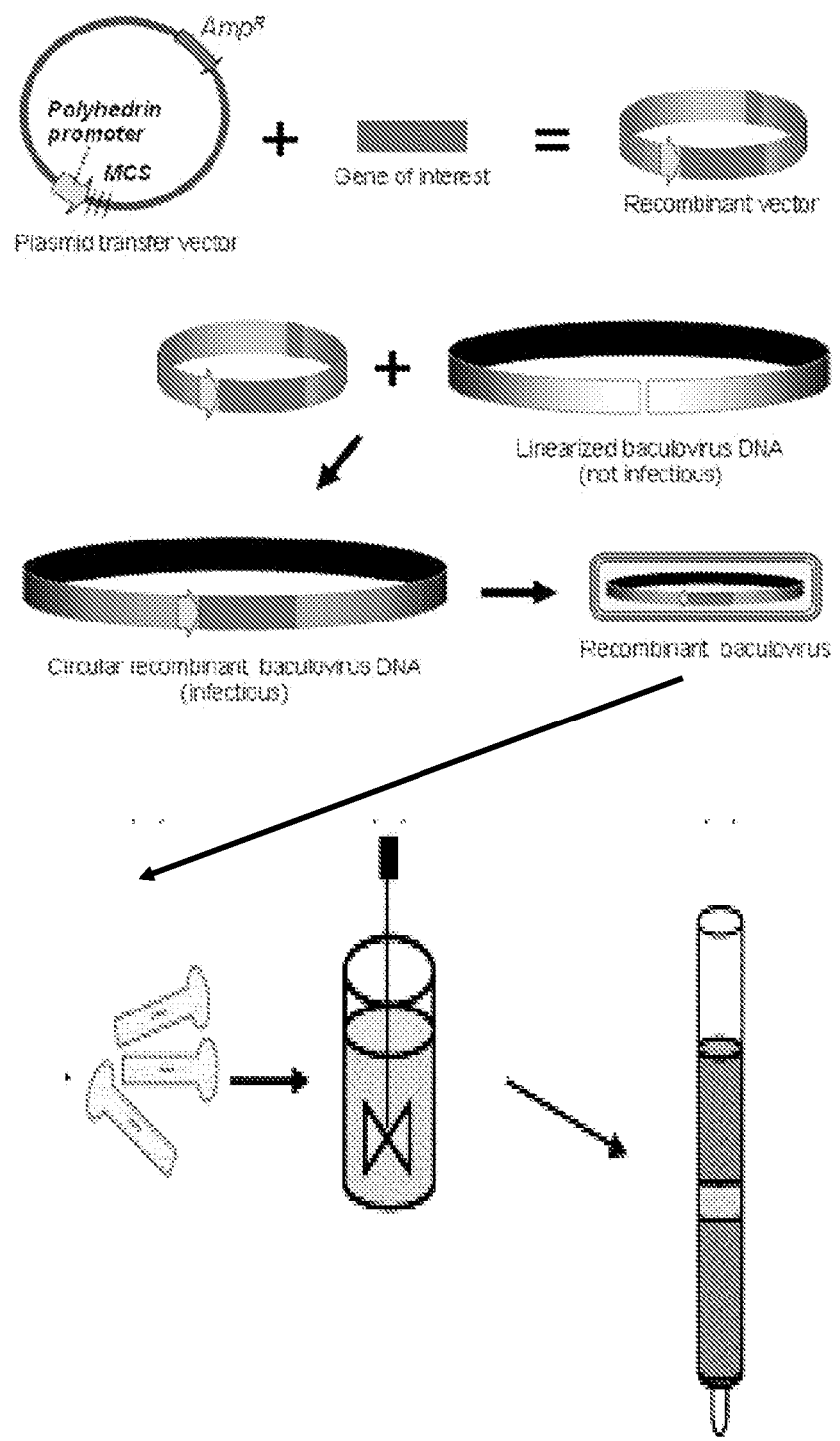
FIG. 11 presents a methodology for producing chimeric VLPs in insect cells from recombinant baculoviruses expressing the L1 major capsid protein. In certain embodiments, VLP purification includes freon extraction of cell lysate, and ultracentrifugation through sucrose cushion followed by discontinuous OptiPrep and then CsCl gradient procedures.
Figure 13:
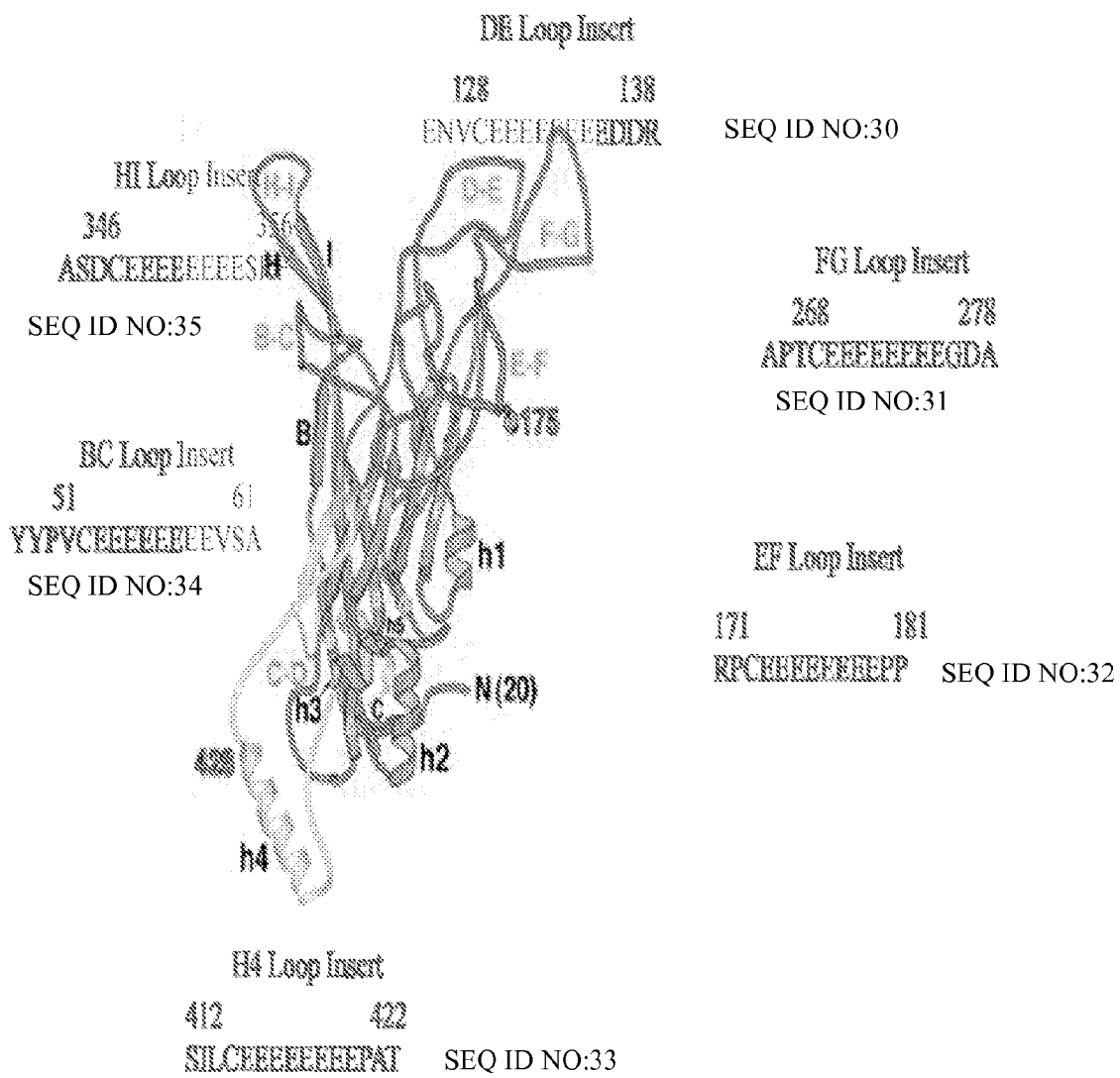
FIG. 13 shows the bovine papillomavirus L1 protein 3-D structure with polyglutamic acid:cysteine sequence inserts at the HI loop, DE loop, FG loop, EF loop, H4 loop and BC loops.
Figure 15A:
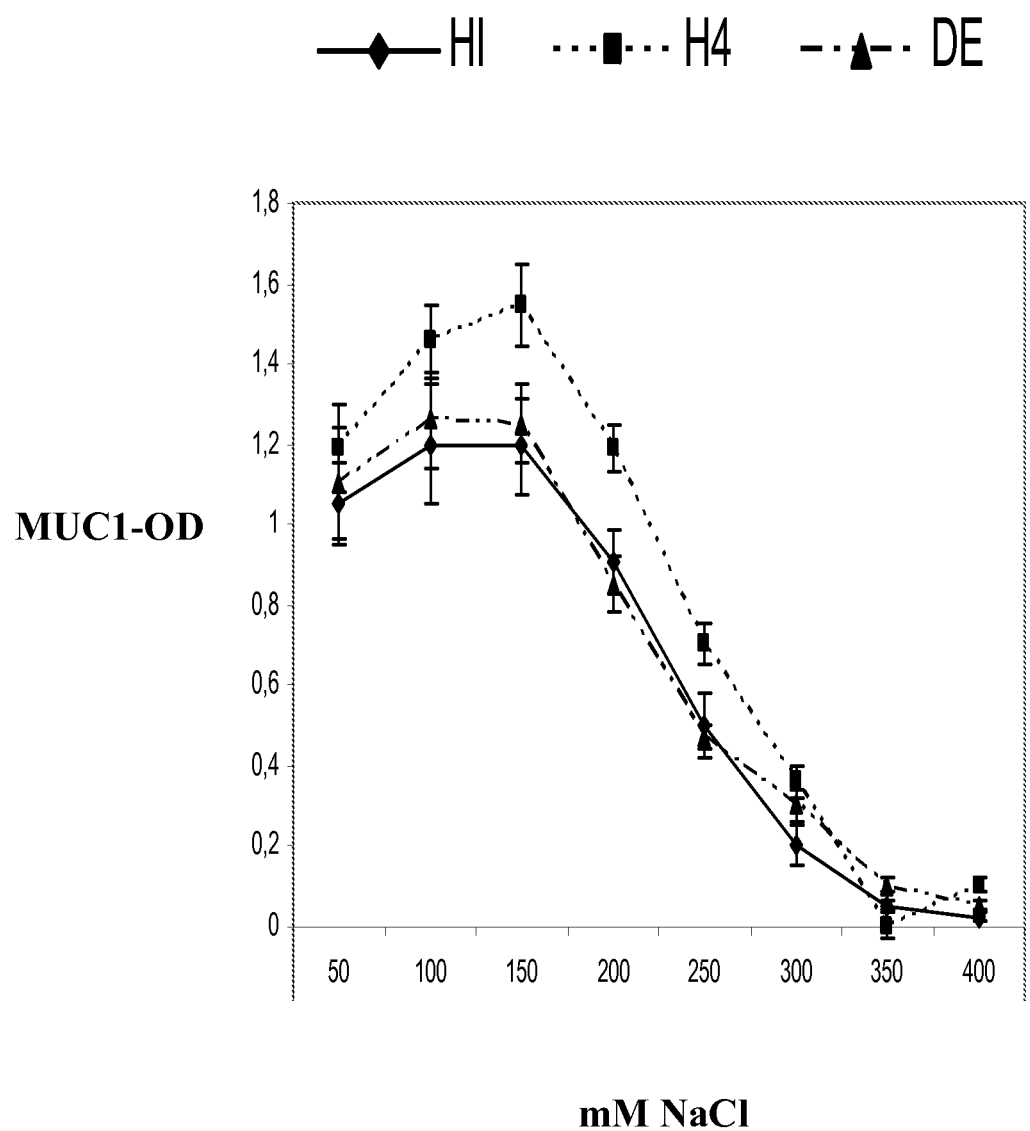
FIG. 15 shows that ionic strength and redox state (GSSG: GSH) determines efficacy of conjugation of polyarginine tagged peptides to polyionic VLPs. Conjugation efficiency was estimated using an ELISA assay with an anti-MUC1 peptide mAb.
Figure 15B:
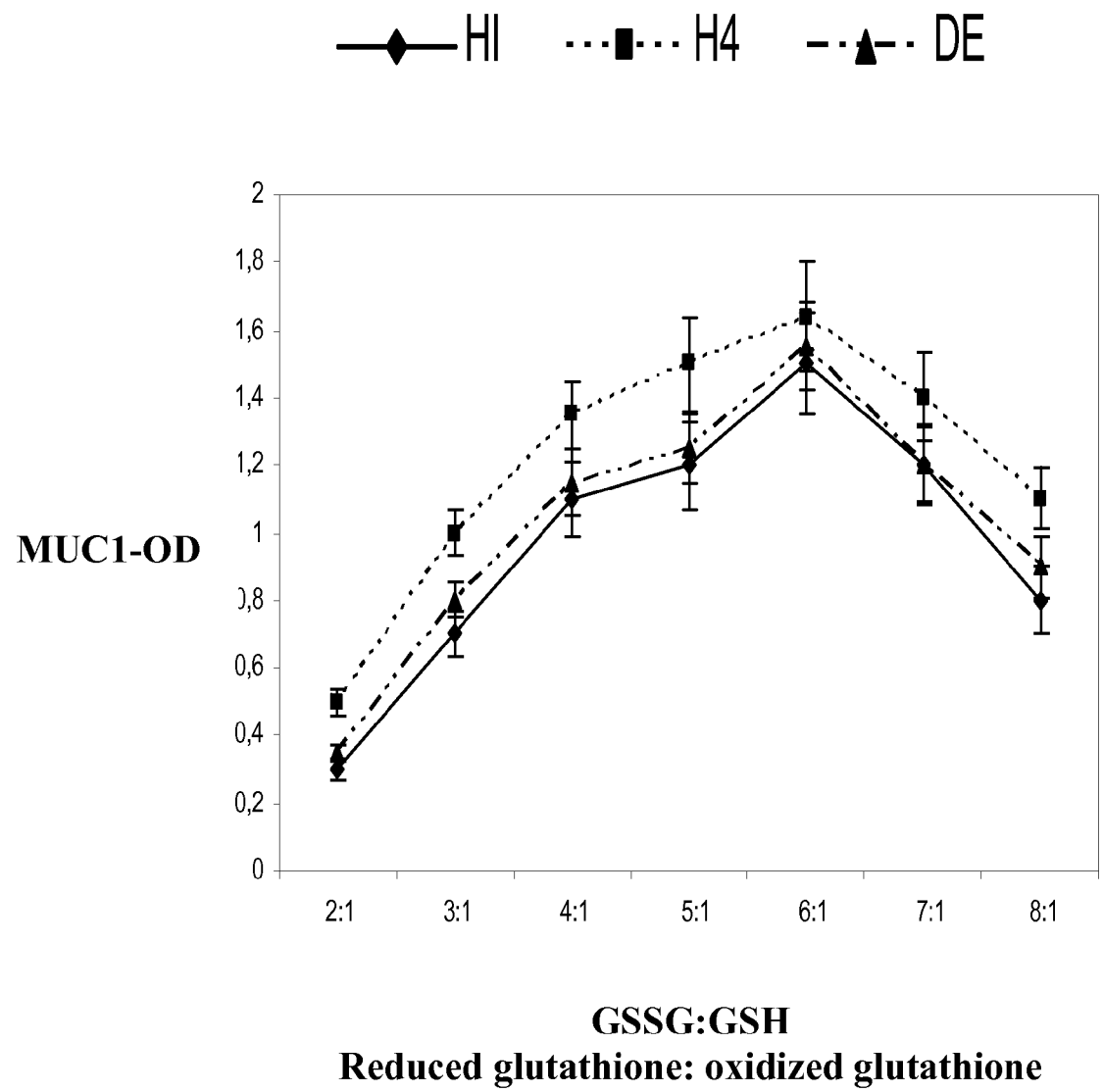
Figure 16:
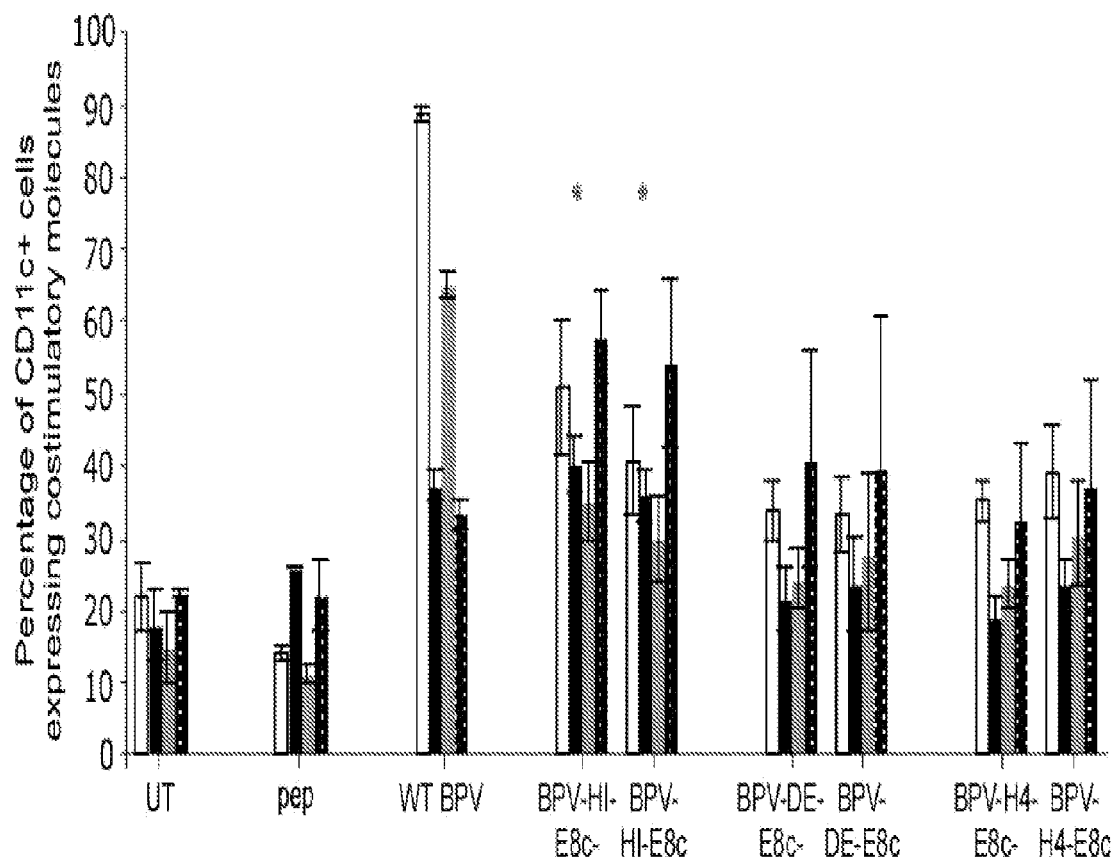
FIG. 16 shows that polyionic VLPs and MUC1 peptide-VLPs retain wild type VLP ability to activate dendritic cells. Capsids (HI Loop Insert), capsomeres (H4) and disordered VLPs (DE) have similar ability to activate DC. Bone marrow DC were loaded with constructs for 24 hours, stained for standard DC maturation markers and analyzed by FACS.
Figure 17:
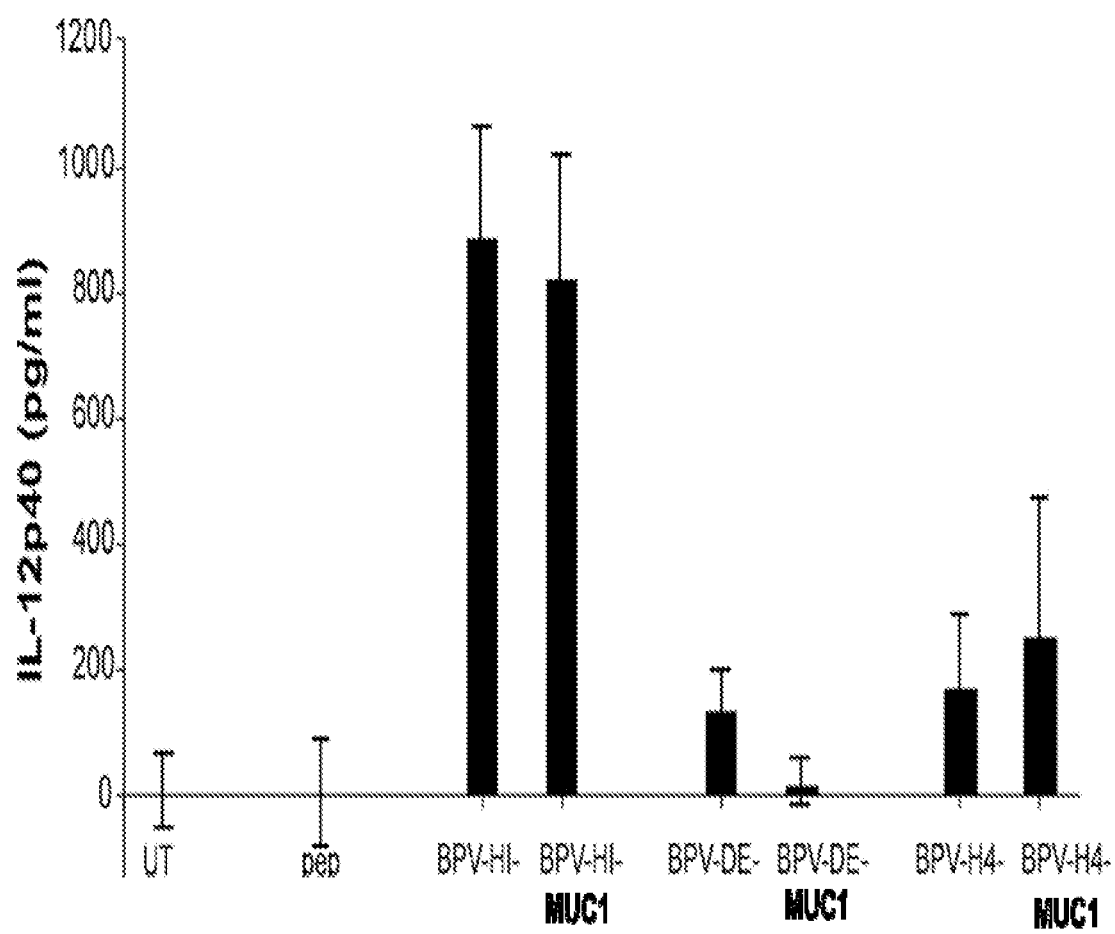
FIG. 17 shows that fully assembled VLPs (HI Loop Insert), but not capsomeres (HR) or disordered VLPs (DE), induce DC to secrete IL-12. IL-12 secretion was measured by ELISA in supernatants harvested from DC cultures, 24 h post-treatment with various VLP constructs.
Figure 18:
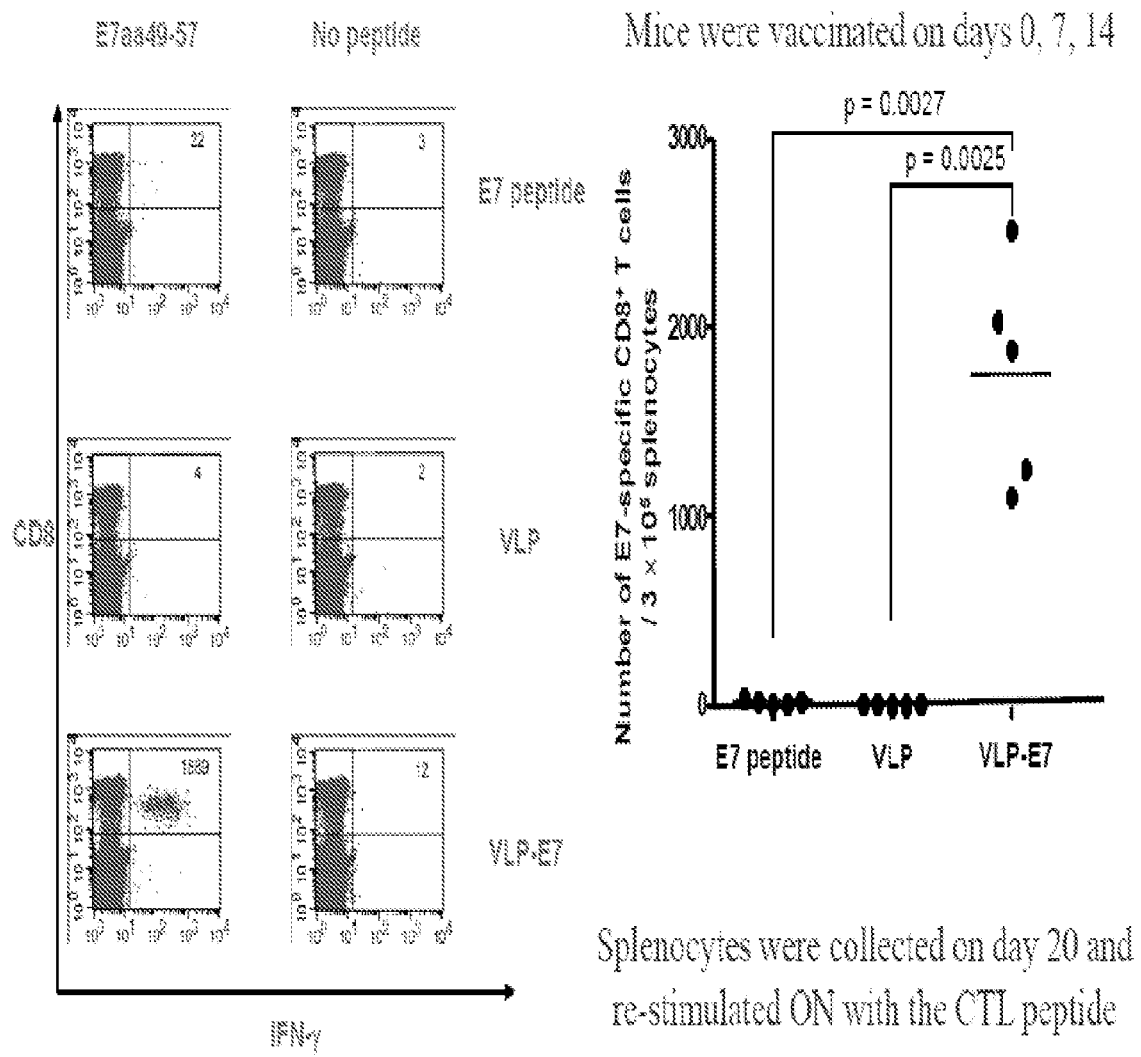
FIG. 18 shows that in vivo immunogenicity of BPV-VLP-HPV E7 (R8CAAY+human papillomavirus 16 E7 Kb CTL epitope aa49-57 (SEQ ID NO:8)) vaccination induces a potent CTL response.
Figure 19:
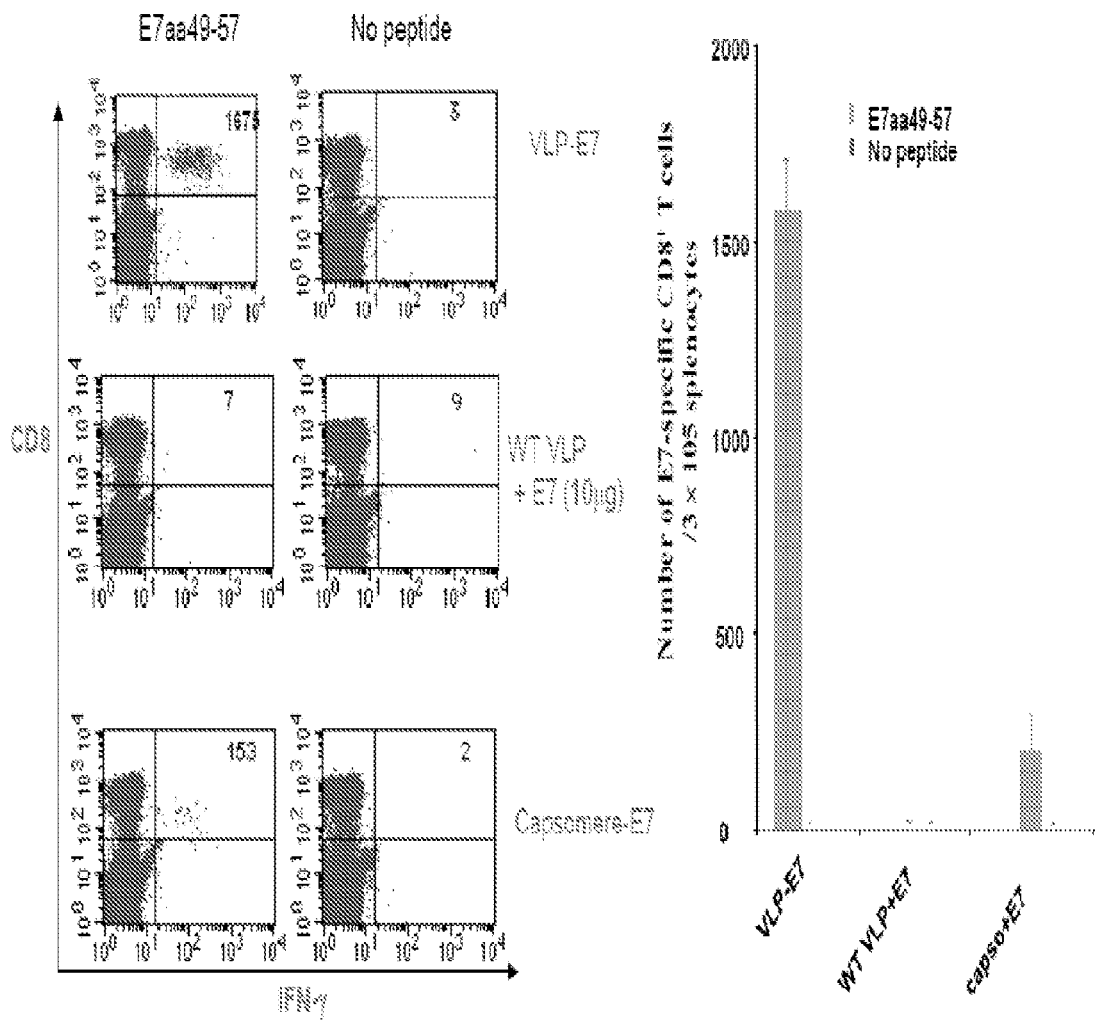
FIG. 19 shows that, in the immunogenicity and in vivo protection studies with HPV E7, wild type VLPs do not provide non-specific adjuvant effect. VLPs are more potent than capsomeres.
Figure 20:
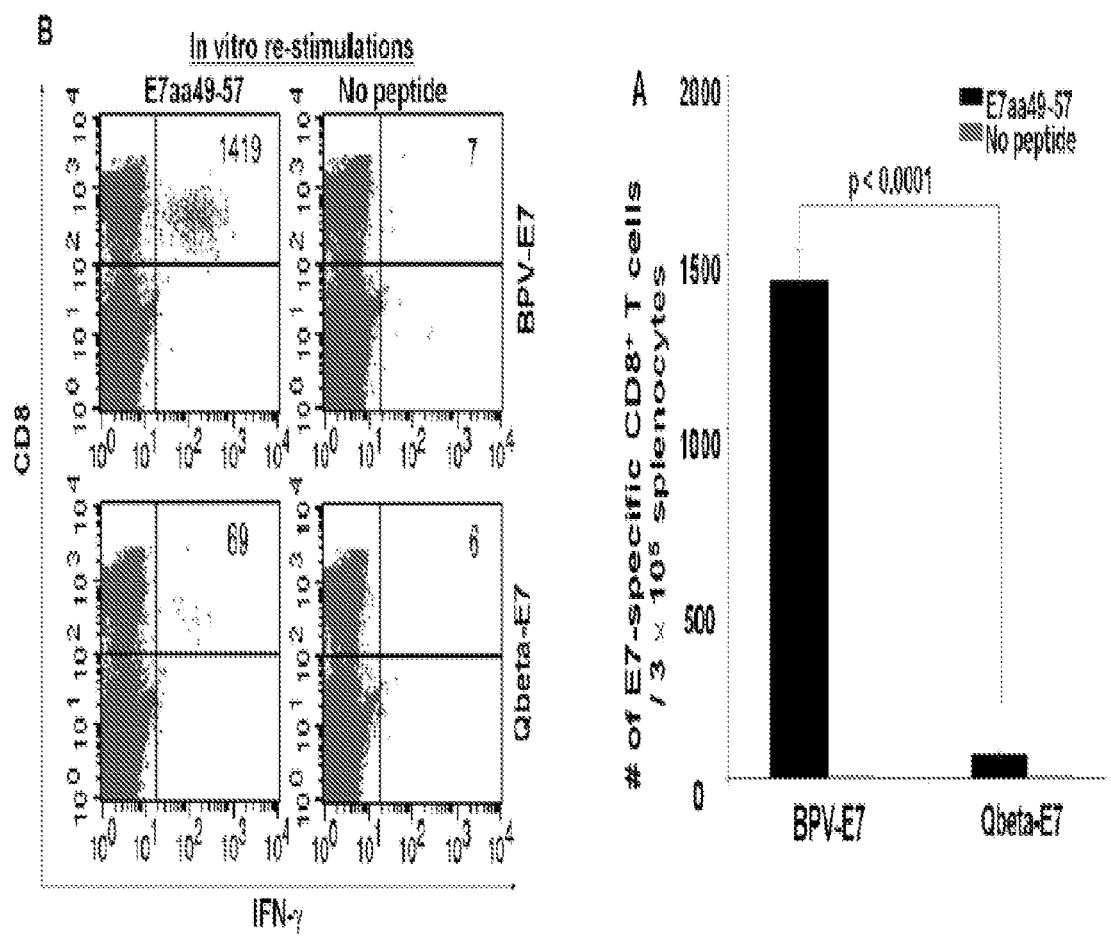
FIG. 20 shows that chimeric papilloma E7 VLPs, but not Qbeta E7 VLPs, induce an E7 specific CD8 T-cell response.
Figure 21:
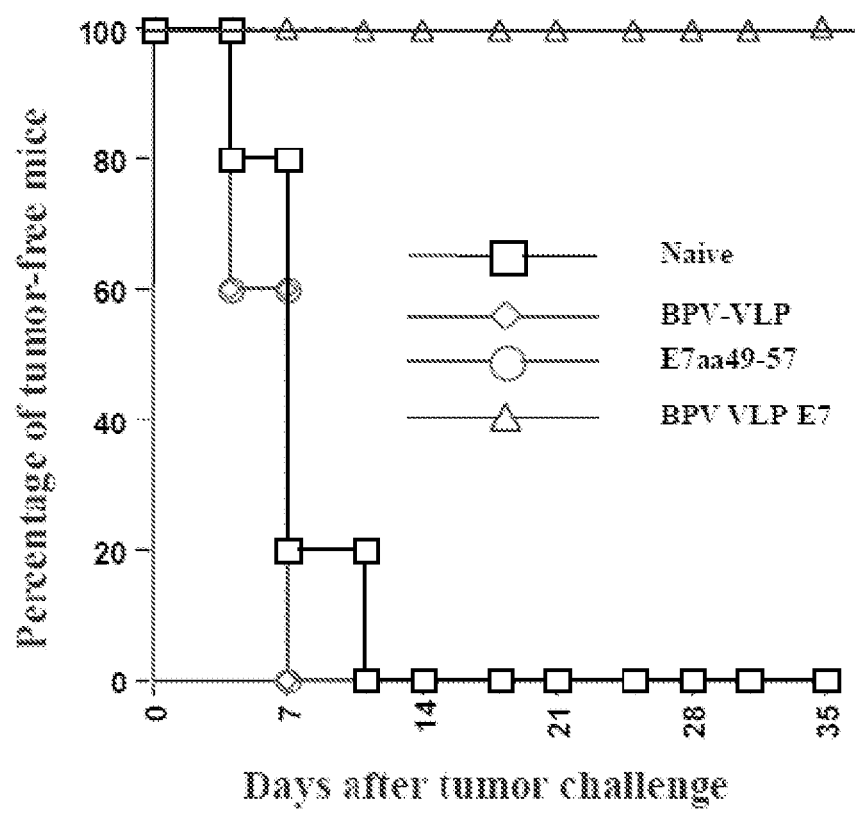
FIG. 21 shows the results of an in vivo protection study using a prophylactic model TC-1 tumor cell line. The TC-1 tumor cell line was derived from lung epithelia of C57BL/6, immortalized with HPV16 E6 and E7, transformed with oncogenic ras, expressed #6 and #7 constitutively at low levels. The cell line grows rapidly in syngeneic mice and is routinely used to test therapeutics for HPV tumors. TC-1 cells were injected subcutaneously on day 0, and mice were immunized on days 7, 14, and 20.
Figure 22:
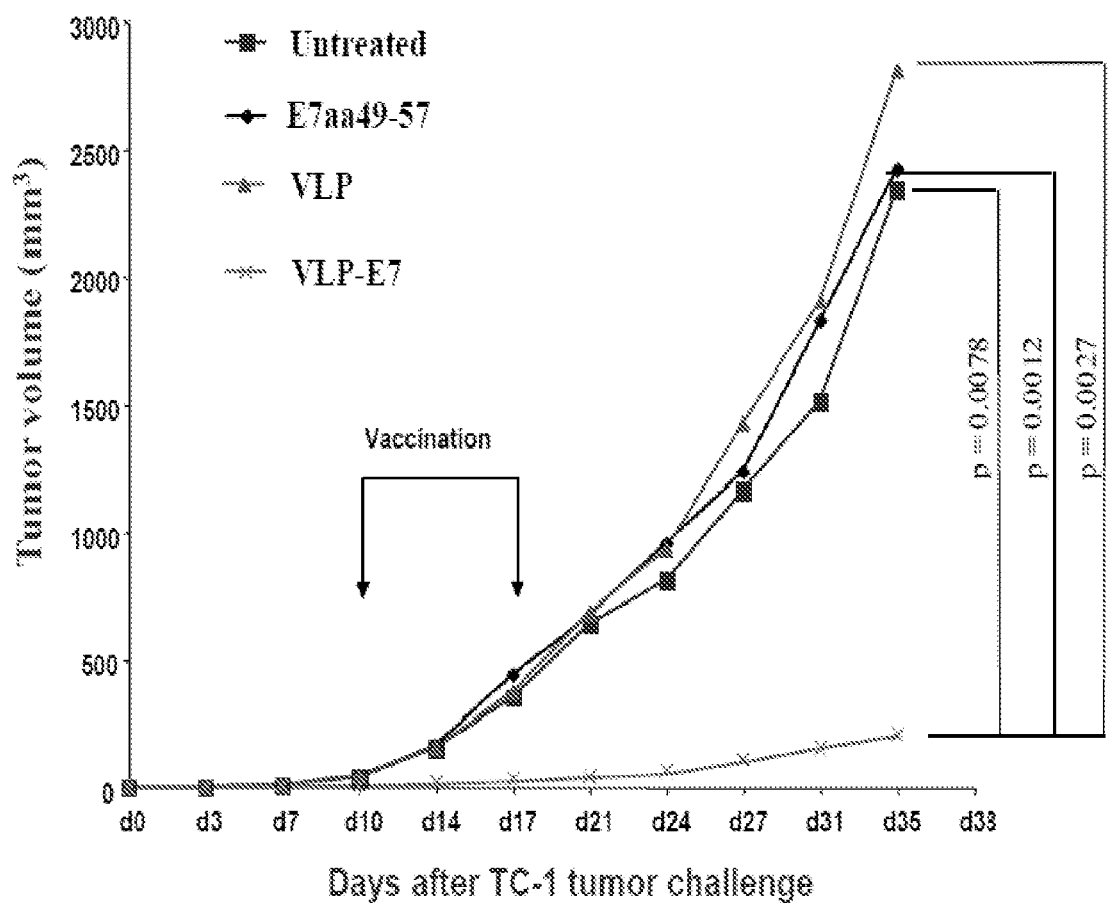
FIG. 22 shows the results of an in vivo protection study using a therapeutic model. Tumor cells were injected subcutaneously.
Figure 24:
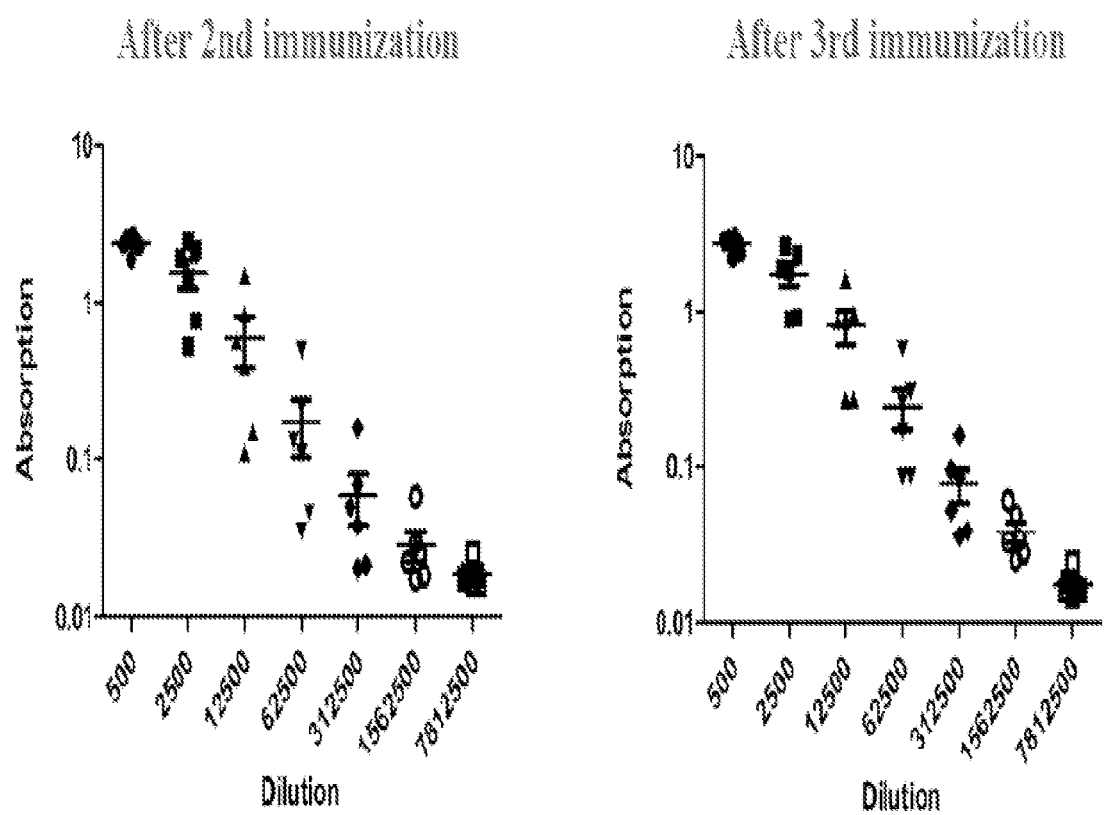
FIG. 24 shows titers of serum antibody to *P. falciparum* circumsporozoite (CS) peptide in ELISA after immunization with Alum/MPL adjuvanted chimeric polyionic BPV malaria B-cell vaccine.
Figure 25:
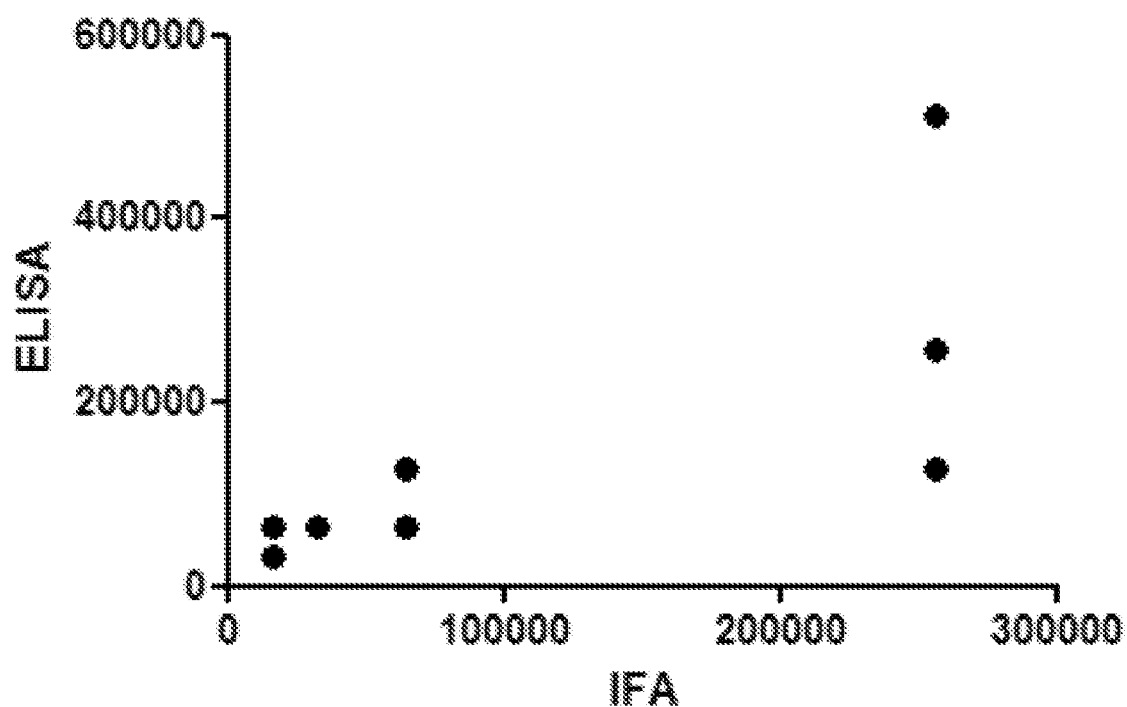
FIG. 25 shows that anti-peptide antibody by ELISA correlates with antibody titer measured by immunofluorescence assay (IFA).
Figure 26:
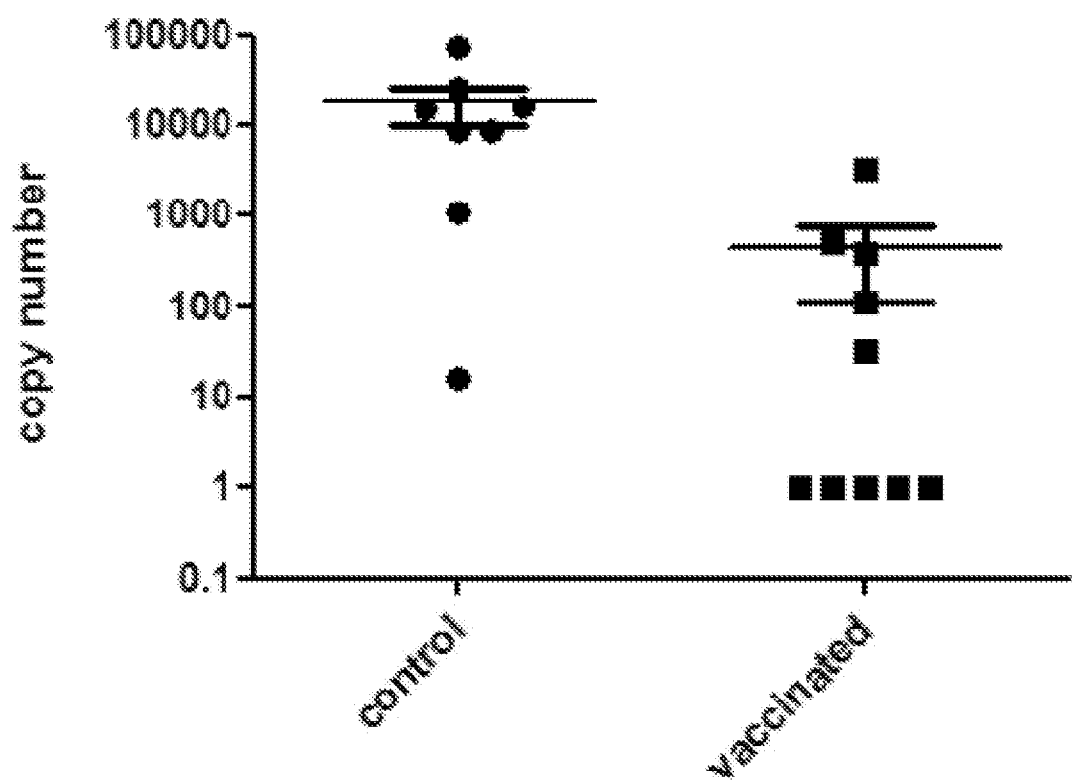
FIG. 26 shows the polyionic CS peptide VLPs protect mice against challenge with *Plasmodium* sporozoites. Mice were challenged intravenously with 15,000 live sporozoites and parasite load in the liver was measured 40 hours later by RT-PCR.
Figure 27:
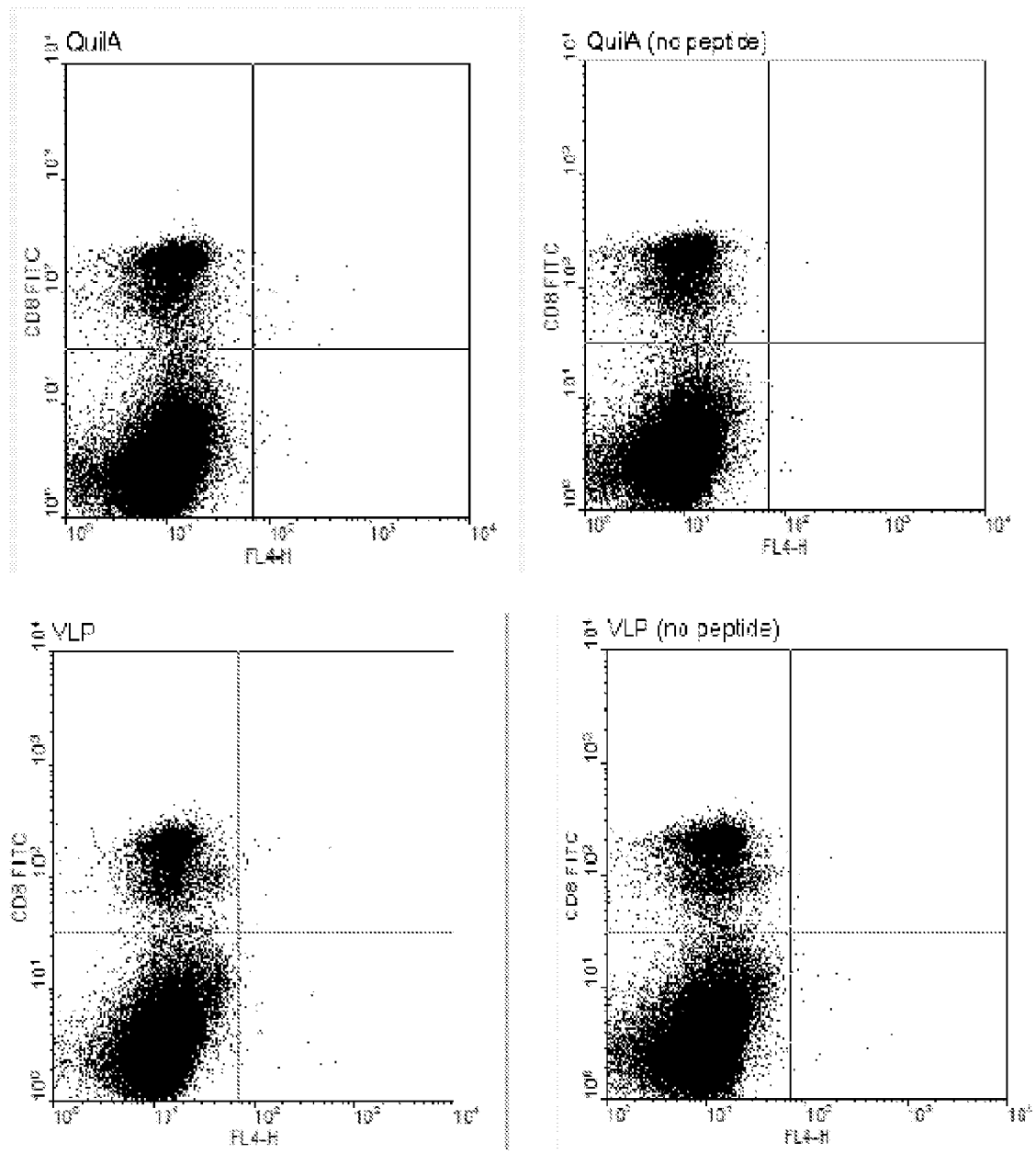
FIGS. 27 and 28 show antigen specific CD8 responses induced by chimeric malaria CS CTL peptide VLPs with and without Quil A adjuvant.
Figure 28:
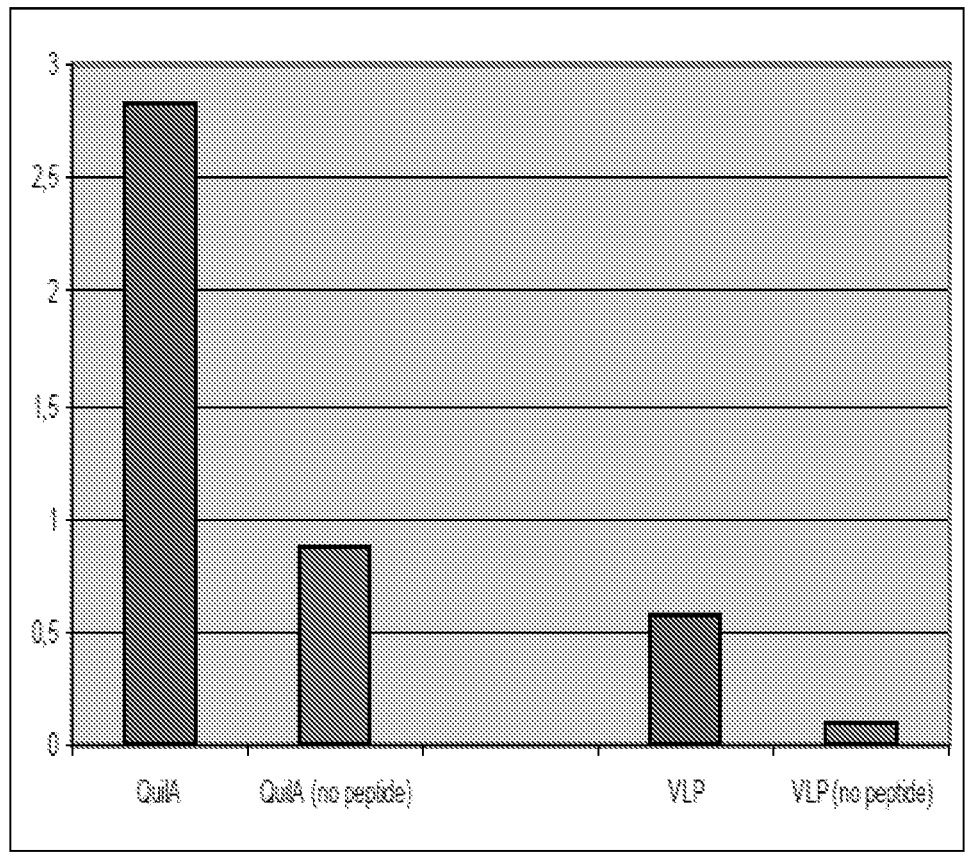

Further evaluation of the humoral arm of the immune response showed no detection of anti-MUC1 antibodies (FIG. 10) in serum samples from infected mice. This was not surprising considering that the short MUC1 peptide contained in the VLP is processed into shorter epitopes by DC for presentation primarily to T cells. These mice, however, were able to generate a robust humoral immunity against BPV VLP, showing that they still had a functional B cell compartment (data not shown).

Vaccines based on the tumor antigen MUC1 could have wide applications against several adenocarcinomas including breast, lung, pancreatic and colon. See Acres et al., 4 EXPERT REV. VACCINES 493-502 (2005); Karsten et al., 26 TUMOUR BIOL. 217-20 (2005); and Byrd et al., 23 CANCER METASTASIS REV. 77-99 (2004). Human MUC1 is one of the few well-characterized tumor neoantigens. See Vlad et al., 82 ADV. IMMUNOL. 249-93 (2004). In several epithelial tumors, polarized expression of MUC1 is lost, and the normally heavily glycosylated protein is overexpressed in hypo- and unglycosylated forms. Brockhausen et al., 233 EUR. J. BIOCHEM. 607-17 (1995). This abnormal glycosylation exposes novel B and T cell epitopes within the TRD making this an immunodominant region and attractive as a candidate cancer vaccine antigen. See Vlad et al., 82 ADV. IMMUNOL. 249-93 (2004). Low-frequency CTL and low-titer IgM responses against MUC1 are present in cancer patients but do not prevent cancer growth. See von Mensdorff-Pouilly et al., 125 METHODS MOL. BIOL. 495-500 (2002); McKolanis et al., 125 METHODS MOL. BIOL. 463-70 (2000); and Kotera et al., 54 CANCER RES. 2856-60 (1994). Therefore, boosting MUC1-specific immunity with VLP vaccines could lead to the development of successful cancer immunotherapy.

In the present study, chimeric papillomavirus VLP that displayed a repetitive array of polyanionic docking sites on its surface were constructed. This type of VLP can serve as a generic vaccine platform for the covalent coupling of polycationic fusion proteins and/or oligopeptides. The major advantage of this approach is that a new VLP will not have to be designed and produced for every new immunogen. In addition, the presence of several docking sites on the VLP would allow for coupling of several epitopes. The feasibility of this approach has been previously demonstrated with polyionic mouse polyomavirus VLPs decorated with by-specific antibodies for the purpose of gene targeting on specific cells. See Stubenrauch et al., 356 BIOCHEM. J. 867-73 (2001).

Several papillomavirus VLPs are potent activators of bone marrow derived DCs and can induce their phenotypic and functional maturation. See Bontkes et al., 96 GYNECOL. ONCOL. 897-901 (2005); Yang et al., 78 J. VIROL. 11152-60 (2004); and Rudolf et al., 166 J. IMMUNOL. 5917-24 (2001). In contrast, most studies have shown that polyomavirus-based VLPs do not induce maturation of DCs in vitro. See Andreasson et al., 124 INT. J. CANCER 150-56 (2009); Tegerstedt et al., 56 CANCER IMMUNOL. IMMUNOTHER. 1335-44 (2007); and Gedvilaite et al., 354 VIROLOGY 252-60 (2006). It is worth mentioning that polyomaviruses and papillomaviruses exhibit differences in receptor specificity and internalization pathways. Yan et al., 324 VIROLOGY 297-310 (2004). Those properties may have arisen from differences in selective pressure during evolution of papillomaviruses and polyomaviruses, and may explain their ability in activating professional antigen presenting cells. Prime examples of successful papillomavirus VLP vaccines are Gardacil, which is composed of HPV-6, -11, -16, 18 VLPs, and Cervarix, which contains HPV-16, -18 VLPs. These vaccines reduce HPV disease by greater than 90%, and are currently used as cervical cancer vaccines worldwide. Schiller et al., 10 VACCINE (SUPPL.) K53-K61 (2008). The excellent immunological properties, as well as their safety profiles, makes papillomavirus VLPs ideal candidates for designing a generic vaccine platform.

Conjugation of the fusion peptide was successful in both chimeric VLPs and capsomeres, albeit with different efficiency. However, only the construct that consisted of fully formed VLP made by substitutions in the HI loop (BPV-HI-E8c-MUC1) caused robust maturation of DC, both in terms of up-regulation of costimulatory molecules, as well as, cytokine production. Importantly, the loop substitution that gave only capsomeres did not cause significant DC maturation.

Vaccination using this MUC1 vaccine (BPV-HI-E8c-MUC1) in MUC1-Tg mice, where human MUC1 is a self molecule (model for tolerance), showed us that this vaccine was capable of activating MUC1-specific CD8+ cytotoxic T cell (CTL), both in terms of proliferation and function. Only a slight increase in MUC1-specific CD4+ T cell proliferation was observed in MUC1-Tg mice following vaccination. This may be due to the extremely low antigen dose contained within the vaccine. Significant T-helper (CD4+ T cells) activation may require much higher amounts of antigen that can be achieved by conjugating a longer peptide with a higher number of tandem repeats, an approach which is currently being explored.

In line with the generation of an anti-MUC1 immunity following vaccination, a significant delay in the MUC1+ tumor appearance and growth and a decreased tumor size was observed in MUC1-Tg mice. The BPV-HI-8Ec-MUC vaccine was administered before tumor challenge, demonstrating its potential efficacy for prevention of recurrent disease. A certain degree of protection was also seen in the vector control treated animals. This non-specific protection is probably due to the significant anti-viral innate immunity that might act as bystander immunity against the tumor cells. Apparently, in this tumor model, MUC1-specific CTL was the only measurable effector mechanism, and was sufficient to see significant efficacy. However, activation of CD4+ T cells may be needed in order to achieve better results than those observed. It is accepted that for a better CD8+ T cell activation CD4+-help is required. Although the known immunogenic properties of papillomavirus VLPs are likely important for the efficacy of the BPV-HI-8Ec-MUC vaccine, future studies are needed to further characterize the mechanism of immune protection afforded by the vaccine.

Example 6

Slower Growth Kinetics and Decreased Tumor Mass in Vaccinated Mice

Figures 6A, 6B:
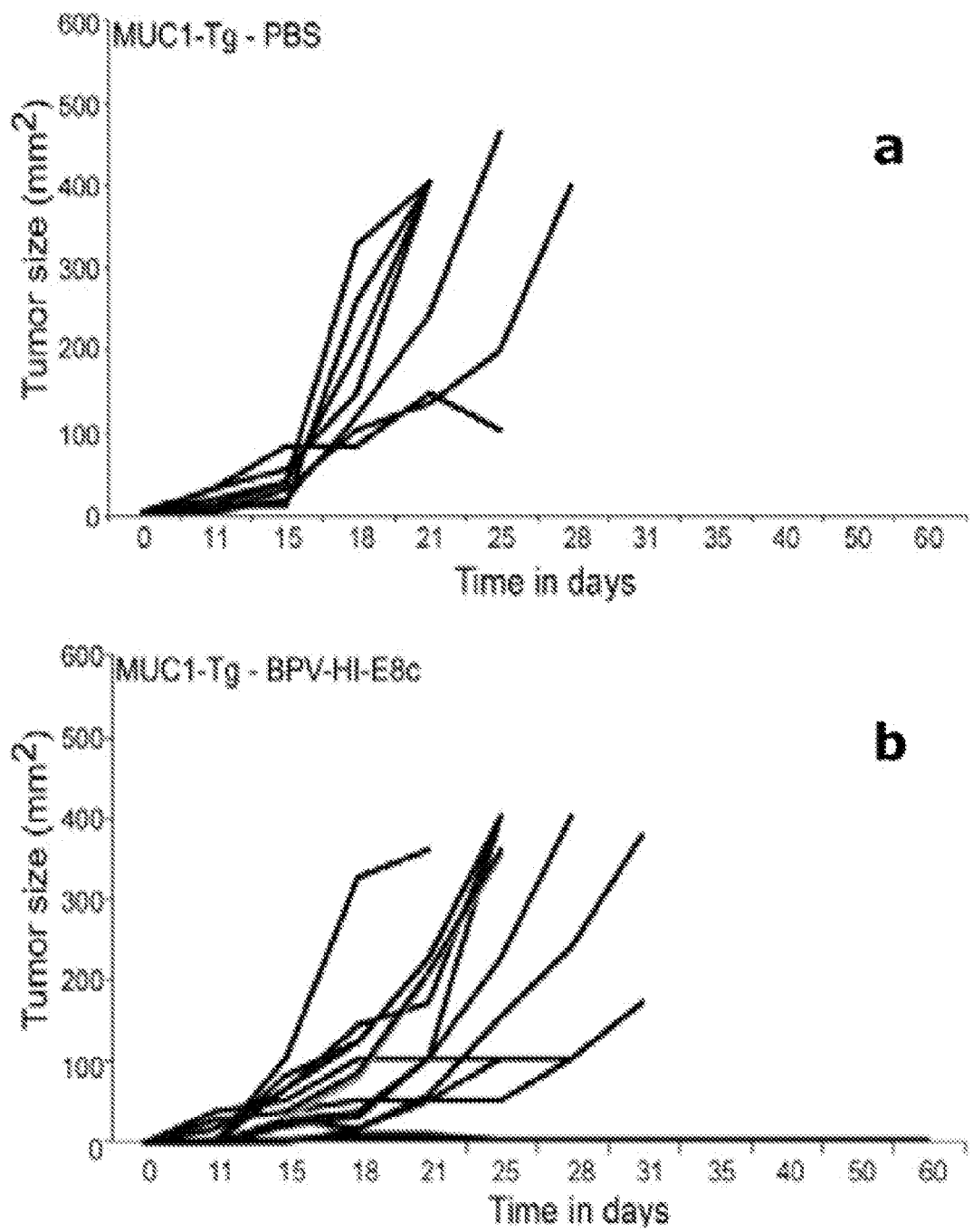
FIG. 6 shows tumor progression following vaccinations. Mice were injected with $5 \times 10^4$ RMA-MUC1 tumor cells 2 weeks following the final vaccine boost (5 g per dose). Tumor progression in individual MUC1-Tg treated with PBS (FIG. 6A), vector alone BPV-HI-E8c (FIG. 6B), and vaccine BPVHI-E8c-MUC1 (FIG. 6C) was followed for 60 days. On day 21 (day before the first mouse in the PBS negative control groups was sacrificed), tumors in all mice in all groups were measured (FIG. 6D). *Values of p<0.05 were considered significant; **p<0.01. n=21 per group for vaccine and vector group and n=9 mice per group for PBS group.
Figure 6C:
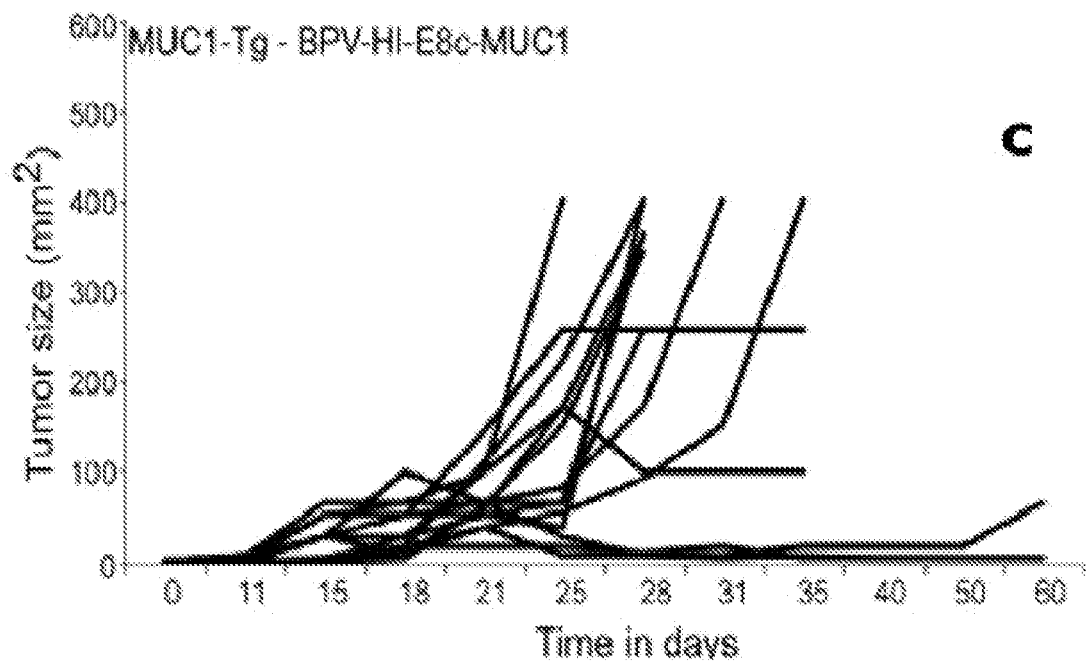
Figure 6D:
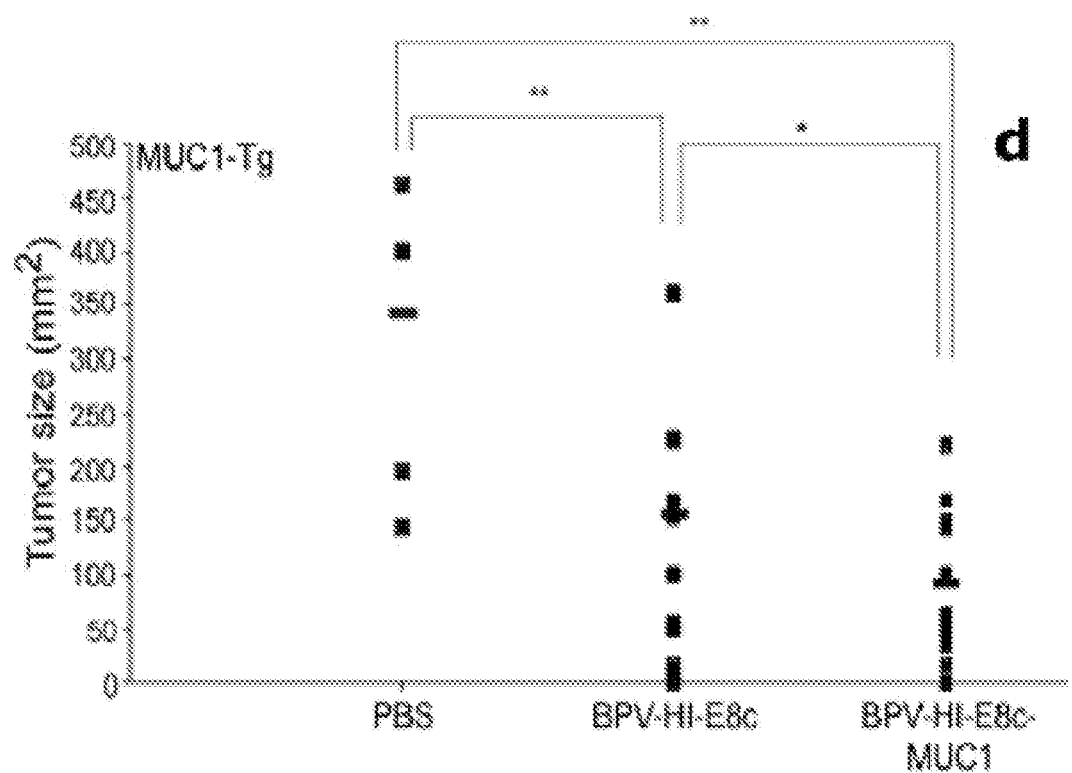

To determine if the vaccine-elicited immune response could affect tumor growth, the tumor size was monitored every 2-3 days up to 60 days. By day 30, 100% of PBS-treated control MUC1-Tg mice were sacrificed because their tumors reached a size of 2 cm (FIG. 6A). In contrast, mice immunized with the BPV-HI-E8c vector control (5 μg per dose) or the BPV-HI-E8c-MUC1 vaccine (5 μg per dose), both showed a lag in tumor appearance, as well as slower growth kinetics, with a strikingly longer time to appearance documented in BPVHI-E8c-MUC1 vaccinated animals (FIGS. 6B and 6C). Measuring the tumors in the two surviving groups on the day that the PBS-treated group had to be sacrificed due to the tumors reaching the size of 2 cm, showed a significantly smaller tumor mass in mice that received the BPVHI-E8c-MUC1 vaccine (FIG. 6D) compared to vector or PBS-treated animals.

Example 7

Immunogenicity and In Vivo Protection Studies with Human Papillomavirus E7 CTL Peptides Conjugated to Polyionic Chimeric VLPs Studies were conducted utilizing the VLPs of the present invention with human papillomavirus (HPV) 16 E7 Kb CTL epitope aa49-57, a well-characterized model immunodominant CTL epitope. The target antigen sequence is CRRRRRRRRCAAY-RAHYNIVTF (SEQ ID NO:8) (normal text is the polycationic sequence; underline text is a leader sequence; italics is the peptide antigen sequence).

Experiments utilized TC-1 tumor cells, a mouse model of HPV-associated cancer. Briefly, mice were vaccinated on days 0, 7 and 14. Splenocytes were collected on day 20 and re-stimulated o/n with the CTL peptide. See FIGS. 18-22.

Example 8

Vaccination Using Dengue Virus CD8 Epitope as the Target Antigen

Figure 29:
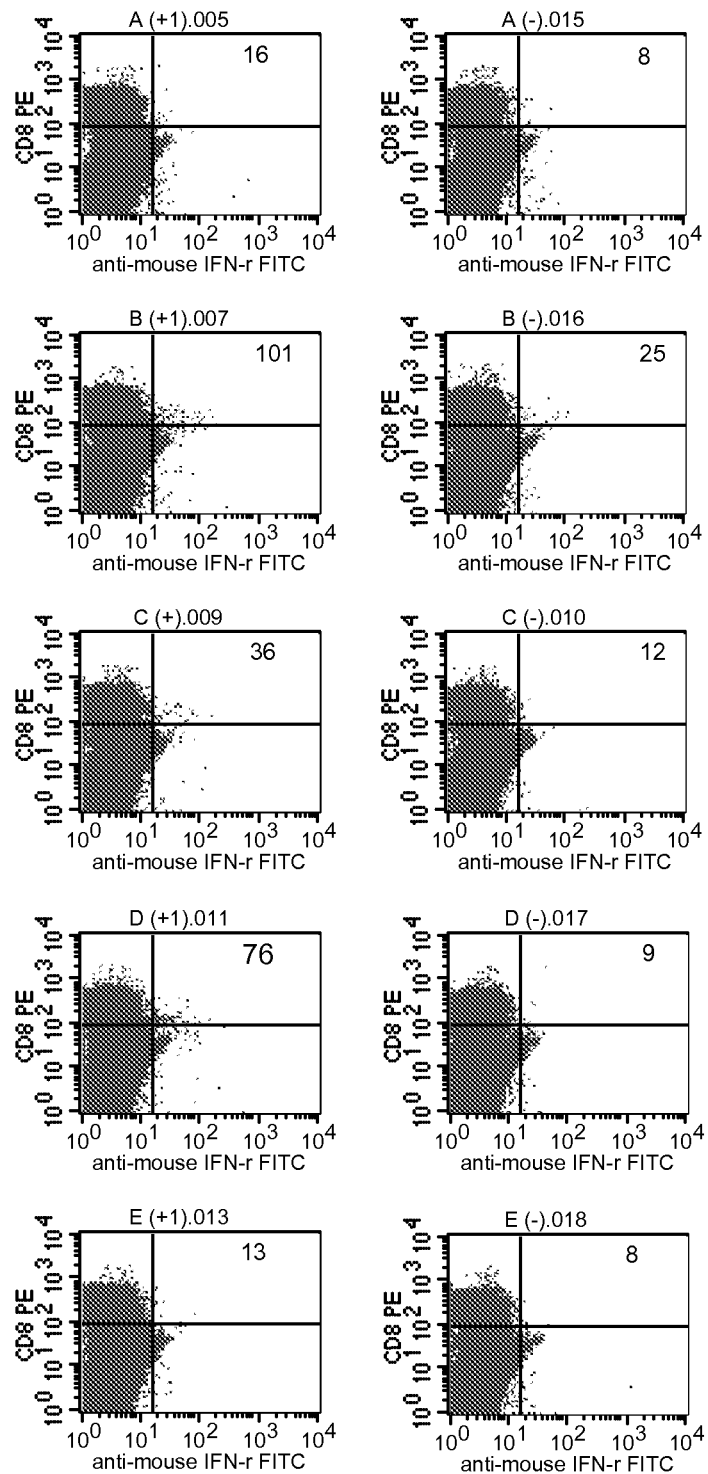
FIG. 29 shows the results from vaccinations using VLPs conjugated to Dengue virus CD8 epitope.
Figure 30:
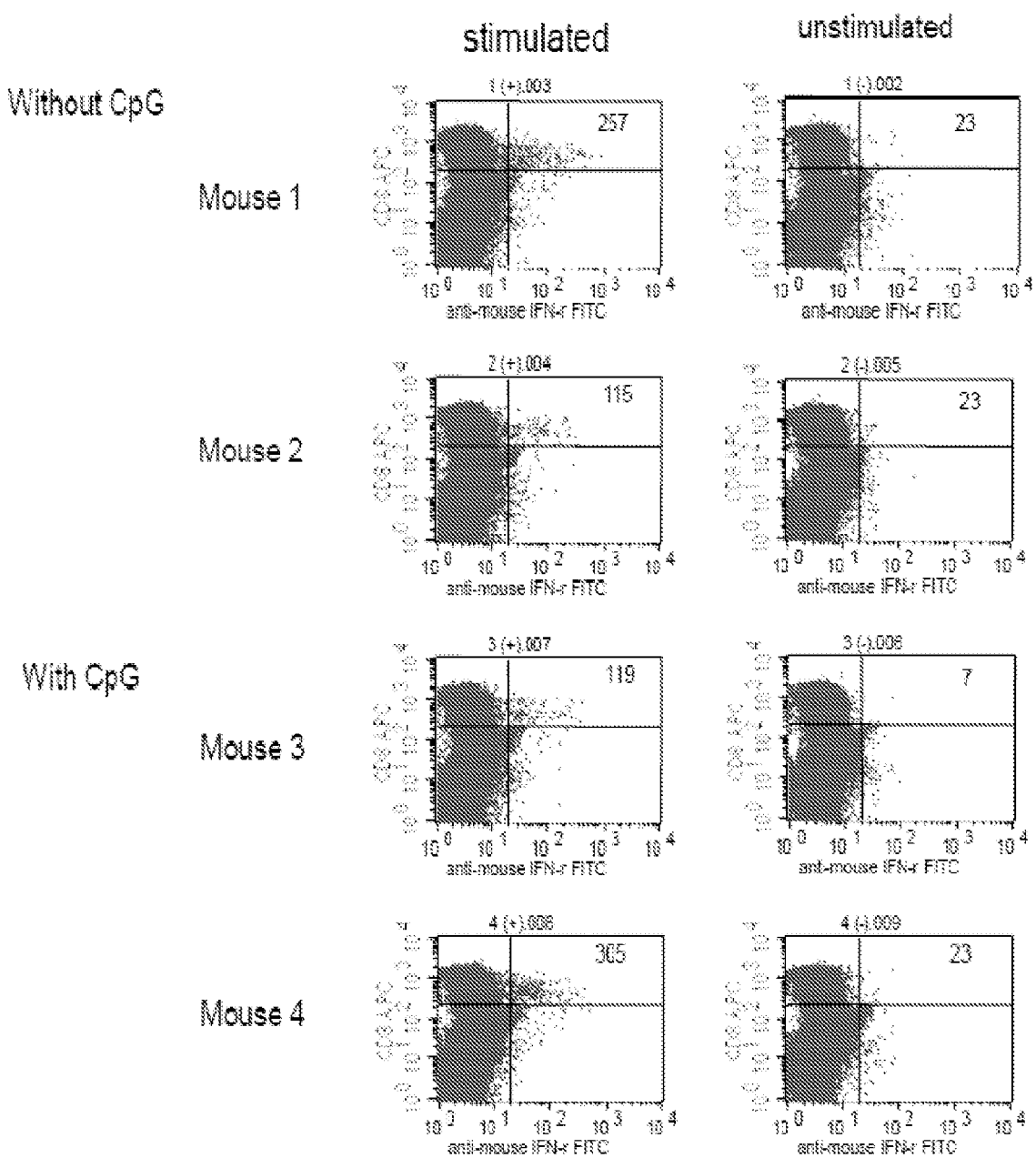
FIG. 30 shows the results from vaccinations using VLPs conjugated to SARS virus CD8 epitope. CD8 response to S525 (CRRRRRRRRCAAYVNFNFNGL (SEQ ID NO:9)) in B6 mice. Immunogen: VLPS525, 12.5 µg, 3 doses, day 0, 7, and 28 via subcutaneous injection. Adjuvant: none or CpG. ICS 8 days after the third dose.

Animal: B6, female 10 W, 2 mice per group. Dose: 7. μg of VLP-peptidin 501 PBS. Two doses, 2 W apart, by subcutaneous injection. FACS analysis: spleen cells taken 8 days after the second dose. Cells were pooled from two mice. Overnight stimulation with cognate peptide (+). (−) without stimulation. Antigens had a CRRRRRRRRCAAY sequence (SEQ ID NO:20) at the N terminus for attachment to VLP. See FIG. 29 and Table 1 below.

TABLE 1

| NAME | VIRAL SEQUENCE | RESPONSE TO VACCINE |
|---|---|---|
| A. NS2A-8 | YFSLGVLGM (SEQ ID NO: 21) | No Response |
| B. NS4B-96 | IGCYSQVNPITLTAA (SEQ ID NO: 22) | Responder |
| C. NS4B-99 | YSQVNPITL (SEQ ID NO: 23) | Weak Response |
| D. NS5-237 | RMLINRFTM (SEQ ID NO: 24) | Responder |
| E. C-51 | VAFLRFLTI (SEQ ID NO: 25) | No Response |

Note:
C epitope contained within peptide B.

REFERENCES

1. Li et al., 7 CURR. CANCER DRUG TARGETS 259-71 (2007).
2. Vlad et al., 82 ADV. IMMUNOL. 249-93 (2004).
3. North et al., 4 EXPERT REV. VACCINES 249-57 (2005).
4. Dorn et al., 21 VIRAL IMMUNOL. 12-27 (2008).
5. Grgacic et al., 40 METHODS 60-5 (2006).

6. Fifis et al., 173 J. IMMUNOL. 3148-54 (2004).
7. Dickgreber et al., 182 J. IMMUNOL. 1260-69 (2009).
8. Boisgérault et al., 1 EXPERT REV. VACCINES 101-09 (2002).
9. Chackerian et al., 108 J. CLIN. INVEST. 415-23 (2001).
10. Peacey et al., 98 BIOTECHNOL. BIOENG. 968-77 (2007).
11. Stubenrauch et al., 356 BIOCHEM. J. 867-73 (2001).
12. Vlad et al., 196 J. EXP. MED. 1435-46 (2002).
13. Alajez et al., 105 BLOOD 4583-89 (2005).
14. Turner et al., 178 J. IMMUNOL. 2787-93 (2007).
15. Soares et al., 166 J. IMMUNOL. 6555-63 (2001).
16. Devêvre et al., 311 J. IMMUNOL. METHODS 31-46 (2006).
17. Goriely et al., 13 CURR. OPIN. ORGAN TRANPLANT. 4-9 (2008).
18. Aktas et al., 254 CELL. IMMUNOL. 149-54 (2009).
19. Acres et al., 4 EXPERT REV. VACCINES 493-502 (2005).
20. Byrd et al., 23 CANCER METASTASIS REV. 77-99 (2004).
21. Karsten et al., 26 TUMOUR BIOL. 217-20 (2005).
22. Brockhausen et al., 233 EUR. J. BIOCHEM. 607-17 (1995).
23. Kotera et al., 54 CANCER RES. 2856-60 (1994).
24. McKolanis et al., 125 METHODS MOL. BIOL. 463-70 (2000).
25. von Mensdorff-Pouilly et al., 125 METHODS MOL. BIOL. 495-500 (2002).
26. Bontkes et al., 96 GYNECOL. ONCOL. 897-901 (2005).
27. Rudolf et al., 166 J. IMMUNOL. 5917-24 (2001).
28. Yang et al., 78 J. VIROL. 11152-60 (2004).
29. Andreasson et al., 124 INT. J. CANCER 150-56 (2009).
30. Tegerstedt et al., 56 CANCER IMMUNOL. IMMUNOTHER. 1335-44 (2007).
31. Gedvilaite et al., 354 VIROLOGY 252-60 (2006).
32. Yan et al., 324 VIROLOGY 297-310 (2004).
33. Schiller et al., 10 VACCINE (SUPPL) K53-K61 (2008).
34. Trus et al., 4 NAT. STRUCT. BIOL. 413-20 (1997).
35. Buck et al., 82 J. VIROL. 5190-97 (2008).
36. Roy et al., 4 HUM. VACCIN. 5-12 (2008).
37. Miyamura et al., 91 PROC. NATL. ACAD. SCI. USA 8507-11 (1994).
38. Müller et al., 234 VIROLOGY 93-111 (1997).
39. Tindle et al., 200 VIROLOGY 547-57 (1994).
40. Wagner et al., 220 VIROLOGY 128-40 (1996).
41. Chen et al., 5 MOL. CELL. 557-67 (2000).

We claim:

1. A vaccine comprising: (a) a chimeric papillomavirus virus-like particle (VLP) comprising a L1 protein, wherein an amino acid sequence EEEEEEEEC (SEQ ID NO: 11) is inserted into the HI loop of the L1 protein; and (b) a target antigen other than the L1 protein, wherein the target antigen comprises a region of positively charged amino acids, and wherein the amino acid sequence EEEEEEEEC (SEQ ID NO: 11) of the HI loop of the L1 protein is covalently bound to the positively charged region of the target antigen.

2. The VLP of claim 1, wherein the papillomavirus is human, bovine, equine, ovine, porcine, deer, canine, feline, or rabbit.

3. The VLP of claim 1, wherein the papillomavirus is bovine.

4. The VLP of claim 3, wherein the EEEEEEEEC (SEQ ID NO:11) amino acid sequence replaces amino acids 347-355 of the HI loop of the L1 protein (SEQ ID NO:5), wherein the bovine papillomavirus is type 1 bovine papillomavirus.

5. The VLP of claim 3, wherein the EEEEEEEEC (SEQ ID NO:11) amino acid sequence replaces amino acids 349-353 of the HI loop of the L1 protein (SEQ ID NO:5), wherein the bovine papillomavirus is type 1 bovine papillomavirus.

6. The VLP of claim 1, wherein the papillomavirus is human.

7. The vaccine of claim 1, wherein the positively charged amino acids are arginine, histidine, lysine, or a combination thereof.

8. The vaccine of claim 1, wherein the positively charged amino acids are arginine.

9. The vaccine claim 1, wherein the region of positively charged amino acids is in consecutive order.

10. The vaccine of claim 9, wherein one or more cysteines are adjacent to the region of positively charged amino acids.

11. The vaccine of claim 1, wherein the target antigen is a peptide or a polypeptide.

12. The vaccine of claim 1, wherein the target antigen is a peptide.

13. The vaccine of claim 1, wherein the target antigen is selected from the group consisting of a tumor antigen, viral antigen, bacterial antigen, fungal antigen, parasitic antigen, and a pathogenic self protein.

14. The vaccine of claim 1, wherein the target antigen is fusion protein.

15. The vaccine of claim 1, wherein the target antigen is MUC1 peptide.

16. The vaccine of claim 1, wherein the target antigen is human papillomavirus 16 E7 CTL epitope amino acids 49-57.

17. The vaccine of claim 1, wherein the target antigen is *P. falciparum* circumsporozoite NANP repeat protein B cell epitope.

18. The vaccine of claim 1, wherein the target antigen is *P. yoellii* circumsporozoite protein CD8 T-cell epitope.

19. The vaccine of claim 1, wherein the target antigen is Dengue virus CD8 epitope.

20. The vaccine of claim 1, wherein the target antigen is Severe Acute Respiratory Syndrome (SARS) virus CD8 epitope.

21. A method of inducing an immune response comprising administering a vaccine of claim 1.

\* \* \* \* \*

SEQUENCE LISTING

```
<160> NUMBER OF SEQ ID NOS: 37

<210> SEQ ID NO 1
<211> LENGTH: 495
<212> TYPE: PRT
<213> ORGANISM: Artificial Sequence
<220> FEATURE:
<223> OTHER INFORMATION: BPV-BC-E8C: E8C amino acids replacing amino
      acids 52-60 in the BC Loop of the L1 protein.

<400> SEQUENCE: 1
```

Met Ala Leu Trp Gln Gln Gly Gln Lys Leu Tyr Leu Pro Pro Thr Pro
1               5                   10                  15

Val Ser Lys Val Leu Cys Ser Glu Thr Tyr Val Gln Arg Lys Ser Ile
            20                  25                  30

Phe Tyr His Ala Glu Thr Glu Arg Leu Leu Thr Ile Gly His Pro Tyr
        35                  40                  45

Tyr Pro Val Cys Glu Glu Glu Glu Glu Glu Val Ser Ala Asn
    50                  55                  60

Gln Tyr Arg Val Phe Lys Ile Gln Leu Pro Asp Pro Asn Gln Phe Ala
65                  70                  75                  80

Leu Pro Asp Arg Thr Val His Asn Pro Ser Lys Glu Arg Leu Val Trp
                85                  90                  95

Ala Val Ile Gly Val Gln Val Ser Arg Gly Gln Pro Leu Gly Gly Thr
            100                 105                 110

Val Thr Gly His Pro Thr Phe Asn Ala Leu Leu Asp Ala Glu Asn Val
        115                 120                 125

Asn Arg Lys Val Thr Thr Gln Thr Thr Asp Asp Arg Lys Gln Thr Gly
    130                 135                 140

Leu Asp Ala Lys Gln Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175

Glu Asn Gly Ala Cys Pro Pro Leu Glu Leu Lys Asn Lys His Ile Glu
            180                 185                 190

Asp Gly Asp Met Met Glu Ile Gly Phe Gly Ala Ala Asn Phe Lys Glu
        195                 200                 205

```
Ile Asn Ala Ser Lys Ser Asp Leu Pro Leu Asp Ile Gln Asn Glu Ile
    210                 215                 220
Cys Leu Tyr Pro Asp Tyr Leu Lys Met Ala Glu Asp Ala Ala Gly Asn
225                 230                 235                 240
Ser Met Phe Phe Phe Ala Arg Lys Glu Gln Val Tyr Val Arg His Ile
            245                 250                 255
Trp Thr Arg Gly Gly Ser Glu Lys Glu Ala Pro Thr Thr Asp Phe Tyr
                260                 265                 270
Leu Lys Asn Asn Lys Gly Asp Ala Thr Leu Lys Ile Pro Ser Val His
            275                 280                 285
Phe Gly Ser Pro Ser Gly Ser Leu Val Ser Thr Asp Asn Gln Ile Phe
290                 295                 300
Asn Arg Pro Tyr Trp Leu Phe Arg Ala Gln Gly Met Asn Asn Gly Ile
305                 310                 315                 320
Ala Trp Asn Asn Leu Leu Phe Leu Thr Val Gly Asp Asn Thr Arg Gly
                325                 330                 335
Thr Asn Leu Thr Ile Ser Val Ala Ser Asp Gly Thr Pro Leu Thr Glu
            340                 345                 350
Tyr Asp Ser Ser Lys Phe Asn Val Tyr His Arg His Met Glu Glu Tyr
            355                 360                 365
Lys Leu Ala Phe Ile Leu Glu Leu Cys Ser Val Glu Ile Thr Ala Gln
370                 375                 380
Thr Val Ser His Leu Gln Gly Leu Met Pro Ser Val Leu Glu Asn Trp
385                 390                 395                 400
Glu Ile Gly Val Gln Pro Pro Thr Ser Ser Ile Leu Glu Asp Thr Tyr
                405                 410                 415
Arg Tyr Ile Glu Ser Pro Ala Thr Lys Cys Ala Ser Asn Val Ile Pro
            420                 425                 430
Ala Lys Glu Asp Pro Tyr Ala Gly Phe Lys Phe Trp Asn Ile Asp Leu
            435                 440                 445
Lys Glu Lys Leu Ser Leu Asp Leu Asp Gln Phe Pro Leu Gly Arg Arg
450                 455                 460
Phe Leu Ala Gln Gln Gly Ala Gly Cys Ser Thr Val Arg Lys Arg Arg
465                 470                 475                 480
Ile Ser Gln Lys Thr Ser Ser Lys Pro Ala Lys Lys Lys Lys
                485                 490                 495

<210> SEQ ID NO 2
<211> LENGTH: 495
<212> TYPE: PRT
<213> ORGANISM: Artificial Sequence
<220> FEATURE:
<223> OTHER INFORMATION: BPV-DE-E8C: E8C amino acids replacing amino
      acids 129-137 in the DE Loop of the L1 protein.

<400> SEQUENCE: 2

Met Ala Leu Trp Gln Gln Gly Gln L

-continued

```
Leu Pro Asp Arg Thr Val His Asn Pro Ser Lys Glu Arg Leu Val Trp
                 85                  90                  95
Ala Val Ile Gly Val Gln Val Ser Arg Gly Gln Pro Leu Gly Gly Thr
            100                 105                 110
Val Thr Gly His Pro Thr Phe Asn Ala Leu Leu Asp Ala Glu Asn Val
            115                 120                 125
Asn Cys Glu Glu Glu Glu Glu Glu Asp Asp Arg Lys Gln Thr Gly
        130                 135                 140
Leu Asp Ala Lys Gln Gln Gln Ile Leu Leu Gly Cys Thr Pro Ala
145                 150                 155                 160
Glu Gly Glu Tyr Trp Thr Thr Ala Arg Pro Cys Val Thr Asp Arg Leu
                165                 170                 175
Glu Asn Gly Ala Cys Pro Pro Leu Glu Leu Lys Asn Lys His Ile Glu
            180                 185                 190
Asp Gly Asp Met Met Glu Ile Gly Phe Gly Ala Ala Asn Phe Lys Glu
            195                 200                 205
Ile Asn Ala Ser Lys Ser Asp Leu Pro Leu Asp Ile Gln Asn Glu Ile
        210                 215                 220
Cys Leu Tyr Pro Asp Tyr Leu Lys Met Ala Glu Asp Ala Ala Gly Asn
225                 230                 235                 240
Ser Met Phe Phe Phe Ala Arg Lys Glu Gln Val Tyr Val Arg His Ile
                245                 250                 255
Trp Thr Arg Gly Gly Ser Glu Lys Glu Ala Pro Thr Thr Asp Phe Tyr
            260                 265                 270
Leu Lys Asn Asn Lys Gly Asp Ala Thr Leu Lys Ile Pro Ser Val His
        275                 280                 285
Phe Gly Ser Pro Ser Gly Ser Leu Val Ser Thr Asp Asn Gln Ile Phe
        290                 295                 300
Asn Arg Pro Tyr Trp Leu Phe Arg Ala Gln Gly Met Asn Asn Gly Ile
305                 310                 315                 320
Ala Trp Asn Asn Leu Leu Phe Leu Thr Val Gly Asp Asn Thr Arg Gly
                325                 330                 335
Thr Asn Leu Thr Ile Ser Val Ala Ser Asp Gly Thr Pro Leu Thr Glu
            340                 345                 350
Tyr Asp Ser Ser Lys Phe Asn Val Tyr His Arg His Met Glu Glu Tyr
        355                 360                 365
Lys Leu Ala Phe Ile Leu Glu Leu Cys Ser Val Glu Ile Thr Ala Gln
        370                 375                 380
Thr Val Ser His Leu Gln Gly Leu Met Pro Ser Val Leu Glu Asn Trp
385                 390                 395                 400
Glu Ile Gly Val Gln Pro Pro Thr Ser Ser Ile Leu Glu Asp Thr Tyr
                405                 410                 415
Arg Tyr Ile Glu Ser Pro Ala Thr Lys Cys Ala Ser Asn Val Ile Pro
            420                 425                 430
Ala Lys Glu Asp Pro Tyr Ala Gly Phe Lys Phe Trp Asn Ile Asp Leu
        435                 440                 445
Lys Glu Lys Leu Ser Leu Asp Leu Asp Gln Phe Pro Leu Gly Arg Arg
        450                 455                 460
Phe Leu Ala Gln Gln Gly Ala Gly Cys Ser Thr Val Arg Lys Arg Arg
465                 470                 475                 480
Ile Ser Gln Lys Thr Ser Ser Lys Pro Ala Lys Lys Lys Lys Lys
                485                 490                 495
```

<210> SEQ ID NO 3
<211> LENGTH: 495
<212> TYPE: PRT
<213> ORGANISM: Artificial Sequence
<220> FEATURE:
<223> OTHER INFORMATION: BPV-HI-E8C: E8C amino acids replacing amino acids 347-355 in the HI Loop of the L1 protein.

<400> SEQUENCE: 3

```
Met Ala Leu Trp Gln Gln Gly Gln Lys Leu Tyr Leu Pro Pro Thr Pro
1               5                   10                  15

Val Ser Lys Val Leu Cys Ser Glu Thr Tyr Val Gln Arg Lys Ser Ile
            20                  25                  30

Phe Tyr His Ala Glu Thr Glu Arg Leu Leu Thr Ile Gly His Pro Tyr
        35                  40                  45

Tyr Pro Val Ser Ile Gly Ala Lys Thr Val Pro Lys Val Ser Ala Asn
    50                  55                  60

Gln Tyr Arg Val Phe Lys Ile Gln Leu Pro Asp Pro Asn Gln Phe Ala
65                  70                  75                  80

Leu Pro Asp Arg Thr Val His Asn Pro Ser Lys Glu Arg Leu Val Trp
                85                  90                  95

Ala Val Ile Gly Val Gln Val Ser Arg Gly Gln Pro Leu Gly Gly Thr
            100                 105                 110

Val Thr Gly His Pro Thr Phe Asn Ala Leu Leu Asp Ala Glu Asn Val
        115                 120                 125

Asn Arg Lys Val Thr Thr Gln Thr Thr Asp Asp Arg Lys Gln Thr Gly
    130                 135                 140

Leu Asp Ala Lys Gln Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175

Glu Asn Gly Ala Cys Pro Pro Leu Glu Leu Lys Asn Lys His Ile Glu
            180                 185                 190

Asp Gly Asp Met Met Glu Ile Gly Phe Gly Ala Ala Asn Phe Lys Glu
        195                 200                 205

Ile Asn Ala Ser Lys Ser Asp Leu Pro Leu Asp Ile Gln Asn Glu Ile
    210                 215                 220

Cys Leu Tyr Pro Asp Tyr Leu Lys Met Ala Glu Asp Ala Ala Gly Asn
225                 230                 235                 240

Ser Met Phe Phe Phe Ala Arg Lys Glu Gln Val Tyr Val Arg His Ile
                245                 250                 255

Trp Thr Arg Gly Gly Ser Glu Lys Glu Ala Pro Thr Thr Asp Phe Tyr
            260                 265                 270

Leu Lys Asn Asn Lys Gly Asp Ala Thr Leu Lys Ile Pro Ser Val His
        275                 280                 285

Phe Gly Ser Pro Ser Gly Ser Leu Val Ser Thr Asp Asn Gln Ile Phe
    290                 295                 300

Asn Arg Pro Tyr Trp Leu Phe Arg Ala Gln Gly Met Asn Asn Gly Ile
305                 310                 315                 320

Ala Trp Asn Asn Leu Leu Phe Leu Thr Val Gly Asp Asn Thr Arg Gly
                325                 330                 335

Thr Asn Leu Thr Ile Ser Val Ala Ser Asp Cys Glu Glu Glu Glu Glu
            340                 345                 350

Glu Glu Glu Ser Lys Phe Asn Val Tyr His Arg His Met Glu Glu Tyr
        355                 360                 365
```

```
Lys Leu Ala Phe Ile Leu Glu Leu Cys Ser Val Glu Ile Thr Ala Gln
            370                 375                 380

Thr Val Ser His Leu Gln Gly Leu Met Pro Ser Val Leu Glu Asn Trp
385                 390                 395                 400

Glu Ile Gly Val Gln Pro Pro Thr Ser Ser Ile Leu Glu Asp Thr Tyr
                405                 410                 415

Arg Tyr Ile Glu Ser Pro Ala Thr Lys Cys Ala Ser Asn Val Ile Pro
                420                 425                 430

Ala Lys Glu Asp Pro Tyr Ala Gly Phe Lys Phe Trp Asn Ile Asp Leu
            435                 440                 445

Lys Glu Lys Leu Ser Leu Asp Leu Asp Gln Phe Pro Leu Gly Arg Arg
450                 455                 460

Phe Leu Ala Gln Gln Gly Ala Gly Cys Ser Thr Val Arg Lys Arg Arg
465                 470                 475                 480

Ile Ser Gln Lys Thr Ser Ser Lys Pro Ala Lys Lys Lys Lys
                485                 490                 495

<210> SEQ ID NO 4
<211> LENGTH: 495
<212> TYPE: PRT
<213> ORGANISM: Artificial Sequence
<220> FEATURE:
<223> OTHER INFORMATION: BPV-H4-E8C: E8C amino acids replacing amino
      acids 413-421 in the H4 Loop of the L1 protein.

<400> SEQUENCE: 4

Met Ala

Ser Met Phe Phe Ala Arg Lys Glu Gln Val Tyr Val Arg His Ile
            245                 250                 255

Trp Thr Arg Gly Gly Ser Glu Lys Glu Ala Pro Thr Thr Asp Phe Tyr
        260                 265                 270

Leu Lys Asn Asn Lys Gly Asp Ala Thr Leu Lys Ile Pro Ser Val His
            275                 280                 285

Phe Gly Ser Pro Ser Gly Ser Leu Val Ser Thr Asp Asn Gln Ile Phe
        290                 295                 300

Asn Arg Pro Tyr Trp Leu Phe Arg Ala Gln Gly Met Asn Asn Gly Ile
305                 310                 315                 320

Ala Trp Asn Asn Leu Leu Phe Leu Thr Val Gly Asp Asn Thr Arg Gly
            325                 330                 335

Thr Asn Leu Thr Ile Ser Val Ala Ser Asp Gly Thr Pro Leu Thr Glu
            340                 345                 350

Tyr Asp Ser Ser Lys Phe Asn Val Tyr His Arg His Met Glu Glu Tyr
            355                 360                 365

Lys Leu Ala Phe Ile Leu Glu Leu Cys Ser Val Glu Ile Thr Ala Gln
        370                 375                 380

Thr Val Ser His Leu Gln Gly Leu Met Pro Ser Val Leu Glu Asn Trp
385                 390                 395                 400

Glu Ile Gly Val Gln Pro Pro Thr Ser Ser Ile Leu Cys Glu Glu Glu
                405                 410                 415

Glu Glu Glu Glu Pro Ala Thr Lys Cys Ala Ser Asn Val Ile Pro
            420                 425                 430

Ala Lys Glu Asp Pro Tyr Ala Gly Phe Lys Phe Trp Asn Ile Asp Leu
        435                 440                 445

Lys Glu Lys Leu Ser Leu Asp Leu Asp Gln Phe Pro Leu Gly Arg Arg
        450                 455                 460

Phe Leu Ala Gln Gln Gly Ala Gly Cys Ser Thr Val Arg Lys Arg Arg
465                 470                 475                 480

Ile Ser Gln Lys Thr Ser Ser Lys Pro Ala Lys Lys Lys Lys
            485                 490                 495

<210> SEQ ID NO 5
<211> LENGTH: 495
<212> TYPE: PRT
<213> ORGANISM: Bovine papillomavirus type 1
<220> FEATURE:
<221> NAME/KEY: MISC_FEATURE
<223> OTHER INFORMATION: BPV-WT: wildtype native L1 protein

<400> SEQUENCE: 5

Met Ala Leu Trp Gln Gln Gly Gln Lys Leu Tyr Leu Pro Pro Thr Pro
1               5                   10                  15

Val Ser Lys Val Leu Cys Ser Glu Thr Tyr Val Gln Arg Lys Ser Ile
            20                  25                  30

Phe Tyr His Ala Glu Thr Glu Arg Leu Leu Thr Ile Gly His Pro Tyr
        35                  40                  45

Tyr Pro Val Ser Ile Gly Ala Lys Thr Val Pro Lys Val Ser Ala Asn
    50                  55                  60

Gln Tyr Arg Val Phe Lys Ile Gln Leu Pro Asp Pro Asn Gln Phe Ala
65                  70                  75                  80

Leu Pro Asp Arg Thr Val His Asn Pro Ser Lys Glu Arg Leu Val Trp
                85                  90                  95

Ala Val Ile Gly Val Gln Val Ser Arg Gly Gln Pro Leu Gly Gly Thr
            100                 105                 110

Val Thr Gly His Pro Thr Phe Asn Ala Leu Leu Asp Ala Glu Asn Val
            115                 120                 125

Asn Arg Lys Val Thr Thr Gln Thr Thr Asp Asp Arg Lys Gln Thr Gly
130                 135                 140

Leu Asp Ala Lys Gln Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175

Glu Asn Gly Ala Cys Pro Pro Leu Glu Leu Lys Asn Lys His Ile Glu
                180                 185                 190

Asp Gly Asp Met Met Glu Ile Gly Phe Gly Ala Ala Asn Phe Lys Glu
                195                 200                 205

Ile Asn Ala Ser Lys Ser Asp Leu Pro Leu Asp Ile Gln Asn Glu Ile
            210                 215                 220

Cys Leu Tyr Pro Asp Tyr Leu Lys Met Ala Glu Asp Ala Ala Gly Asn
225                 230                 235                 240

Ser Met Phe Phe Phe Ala Arg Lys Glu Gln Val Tyr Val Arg His Ile
                245                 250                 255

Trp Thr Arg Gly Gly Ser Glu Lys Glu Ala Pro Thr Thr Asp Phe Tyr
                260                 265                 270

Leu Lys Asn Asn Lys Gly Asp Ala Thr Leu Lys Ile Pro Ser Val His
            275                 280                 285

Phe Gly Ser Pro Ser Gly Ser Leu Val Ser Thr Asp Asn Gln Ile Phe
            290                 295                 300

Asn Arg Pro Tyr Trp Leu Phe Arg Ala Gln Gly Met Asn Asn Gly Ile
305                 310                 315                 320

Ala Trp Asn Asn Leu Leu Phe Leu Thr Val Gly Asp Asn Thr Arg Gly
                325                 330                 335

Thr Asn Leu Thr Ile Ser Val Ala Ser Asp Gly Thr Pro Leu Thr Glu
                340                 345                 350

Tyr Asp Ser Ser Lys Phe Asn Val Tyr His Arg His Met Glu Glu Tyr
            355                 360                 365

Lys Leu Ala Phe Ile Leu Glu Leu Cys Ser Val Glu Ile Thr Ala Gln
            370                 375                 380

Thr Val Ser His Leu Gln Gly Leu Met Pro Ser Val Leu Glu Asn Trp
385                 390                 395                 400

Glu Ile Gly Val Gln Pro Pro Thr Ser Ser Ile Leu Glu Asp Thr Tyr
                405                 410                 415

Arg Tyr Ile Glu Ser Pro Ala Thr Lys Cys Ala Ser Asn Val Ile Pro
                420                 425                 430

Ala Lys Glu Asp Pro Tyr Ala Gly Phe Lys Phe Trp Asn Ile Asp Leu
                435                 440                 445

Lys Glu Lys Leu Ser Leu Asp Leu Asp Gln Phe Pro Leu Gly Arg Arg
            450                 455                 460

Phe Leu Ala Gln Gln Gly Ala Gly Cys Ser Thr Val Arg Lys Arg Arg
465                 470                 475                 480

Ile Ser Gln Lys Thr Ser Ser Lys Pro Ala Lys Lys Lys Lys
                485                 490                 495

<210> SEQ ID NO 6
<211> LENGTH: 32
<212> TYPE: PRT
<213> ORGANISM: Artificial Sequence

```
<220> FEATURE:
<223> OTHER INFORMATION: R8C amino acid sequence with GSG leader
      sequence conjugated to the 20 amino acid MUC1 peptide.

<400> SEQUENCE: 6

Arg Arg Arg Arg Arg Arg Arg Arg Cys Gly Ser Gly Val Thr Ser
1               5                   10                  15

Ala Pro Asp Thr Arg Pro Ala Pro Gly Ser Thr Ala Pro Pro Ala His
            20                  25                  30

<210> SEQ ID NO 7
<211> LENGTH: 20
<212> TYPE: PRT
<213> ORGANISM: Artificial Sequence
<220> FEATURE:
<223> OTHER INFORMATION: MUC1 peptide target antigen

<400> SEQUENCE: 7

Gly Val Thr Ser Ala Pro Asp Thr Arg Pro Ala Pro Gly Ser Thr Ala
1               5                   10                  15

Pro Pro Ala His
            20

<210> SEQ ID NO 8
<211> LENGTH: 23
<212> TYPE: PRT
<213> ORGANISM: Artificial Sequence
<220> FEATURE:
<223> OTHER INFORMATION: R8C polycationic:cysteine region and AAY leader
      sequence conjugated to the human papillomaivurs 16 E7 Kb CTL
      epitope aa49-57.

<400> SEQUENCE: 8

Cys Arg Arg Arg Arg Arg Arg Arg Arg Cys Ala Ala Tyr Arg Ala His
1               5                   10                  15

Tyr Asn Ile Thr Val Thr Phe
            20

<210> SEQ ID NO 9
<211> LENGTH: 21
<212> TYPE: PRT
<213> ORGANISM: Artificial Sequence
<220> FEATURE:
<223> OTHER INFORMATION: CR8C polycationic:cysteine region and AAY
      leader sequence conjugated to the SARS virus CD8 target antigen.

<400> SEQUENCE: 9

Cys Arg Arg Arg Arg Arg Arg Arg Arg Cys Ala Ala Tyr Val Asn Phe
1               5                   10                  15

Asn Phe Asn Gly Leu
            20

<210> SEQ ID NO 10
<211> LENGTH: 469
<212> TYPE: PRT
<213> ORGANISM: Bovine papillomavirus type 1
<220> FEATURE:
<221> NAME/KEY: MISC_FEATURE
<223> OTHER INFORMATION: Native L2 protein

<400> SEQUENCE: 10

Met Ser Ala Arg Lys Arg Val Lys Arg Ala Ser Ala Tyr Asp Leu Tyr
1               5                   10                  15

Arg Thr Cys Lys Gln Ala Gly Thr Cys Pro Pro Asp Val Ile Pro Lys
            20                  25                  30
```

```
Val Glu Gly Asp Thr Ile Ala Asp Lys Ile Leu Lys Phe Gly Gly Leu
         35                  40                  45

Ala Ile Tyr Leu Gly Gly Leu Gly Ile Gly Thr Trp Ser Thr Gly Arg
 50                  55                  60

Val Ala Ala Gly Gly Ser Pro Arg Tyr Thr Pro Leu Arg Thr Ala Gly
 65                  70                  75                  80

Ser Thr Ser Ser Leu Ala Ser Ile Gly Ser Arg Ala Val Thr Ala Gly
                 85                  90                  95

Thr Arg Pro Ser Ile Gly Ala Gly Ile Pro Leu Asp Thr Leu Glu Thr
            100                 105                 110

Leu Gly Ala Leu Arg Pro Gly Val Tyr Glu Asp Thr Val Leu Pro Glu
            115                 120                 125

Ala Pro Ala Ile Val Thr Pro Asp Ala Val Pro Ala Asp Ser Gly Leu
130                 135                 140

Asp Ala Leu Ser Ile Gly Thr Asp Ser Ser Thr Glu Thr Leu Ile Thr
145                 150                 155                 160

Leu Leu Glu Pro Glu Gly Pro Glu Asp Ile Ala Val Leu Glu Leu Gln
                165                 170                 175

Pro Leu Asp Arg Pro Thr Trp Gln Val Ser Asn Ala Val His Gln Ser
            180                 185                 190

Ser Ala Tyr His Ala Pro Leu Gln Leu Gln Ser Ser Ile Ala Glu Thr
            195                 200                 205

Ser Gly Leu Glu Asn Ile Phe Val Gly Gly Ser Gly Leu Gly Asp Thr
            210                 215                 220

Gly Gly Glu Asn Ile Glu Leu Thr Tyr Phe Gly Ser Pro Arg Thr Ser
225                 230                 235                 240

Thr Pro Arg Ser Ile Ala Ser Lys Ser Arg Gly Ile Leu Asn Trp Phe
                245                 250                 255

Ser Lys Arg Tyr Tyr Thr Gln Val Pro Thr Glu Asp Pro Glu Val Phe
            260                 265                 270

Ser Ser Gln Thr Phe Ala Asn Pro Leu Tyr Glu Ala Glu Pro Ala Val
            275                 280                 285

Leu Lys Gly Pro Ser Gly Arg Val Gly Leu Ser Gln Val Tyr Lys Pro
            290                 295                 300

Asp Thr Leu Thr Thr Arg Ser Gly Thr Glu Val Gly Pro Gln Leu His
305                 310                 315                 320

Val Arg Tyr Ser Leu Ser Thr Ile His Glu Asp Val Glu Ala Ile Pro
                325                 330                 335

Tyr Thr Val Asp Glu Asn Thr Gln Gly Leu Ala Phe Val Pro Leu His
            340                 345                 350

Glu Glu Gln Ala Gly Phe Glu Glu Ile Glu Leu Asp Asp Phe Ser Glu
            355                 360                 365

Thr His Arg Leu Leu Pro Gln Asn Thr Ser Ser Thr Pro Val Gly Ser
            370                 375                 380

Gly Val Arg Arg Ser Leu Ile Pro Thr Gln Glu Phe Ser Ala Thr Arg
385                 390                 395                 400

Pro Thr Gly Val Val Thr Tyr Gly Ser Pro Asp Thr Tyr Ser Ala Ser
                405                 410                 415

Pro Val Thr Asp Pro Asp Ser Thr Ser Pro Ser Leu Val Ile Asp Asp
            420                 425                 430

Thr Thr Thr Thr Pro Ile Ile Ile Ile Asp Gly His Thr Val Asp Leu
            435                 440                 445
```

```
Tyr Ser Ser Asn Tyr Thr Leu His Pro Ser Leu Leu Arg Lys Arg Lys
    450                 455                 460

Lys Arg Lys His Ala
465

<210> SEQ ID NO 11
<211> LENGTH: 9
<212> TYPE: PRT
<213> ORGANISM: Artificial Sequence
<220> FEATURE:
<223> OTHER INFORMATION: Polyglutamic acid:cysteine sequence embodiment
      inserted into loop sequence (e.g.a, HI) of L1 protein.

<400> SEQUENCE: 11

Glu Glu Glu Glu Glu Glu Glu Glu Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Polyarginine:cysteine sequence embodiment
      conjugated to target antigen polypeptide sequence.

<400> SEQUENCE: 12

Arg Arg Arg Arg Arg Arg Arg Arg Cys
1               5

<210> SEQ ID NO 13
<211> LENGTH: 10
<212> TYPE: PRT
<213> ORGANISM: Artificial Sequence
<220> FEATURE:
<223> OTHER INFORMATION: Polyarginine:cysteine sequence embodiment
      conjugated to target antigen polypeptide sequence.

<400> SEQUENCE: 13

Cys Arg Arg Arg Arg Arg Arg Arg Arg Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: human papillomaivurs 16 E7 Kb CTL epitope
      aa49-57.

<400> SEQUENCE: 14

Ala Ala Tyr Arg Ala His Tyr Asn Ile Val Thr Phe
1               5                   10

<210> SEQ ID NO 15
<211> LENGTH: 39
<212> TYPE: PRT
<213> ORGANISM: Artificial Sequence
<220> FEATURE:
<223> OTHER INFORMATION: Polyarginine:cysteine region, CG leader
      sequence, and P. falciparum circumsporozoite protein B-cell
      epitope target antigen sequence
```

```
<400> SEQUENCE: 15

Cys Arg Arg Arg Arg Arg Arg Arg Cys Gly Asn Ala Asn Pro Asn
1               5                   10                  15

Val Asp Pro Asn Ala Asn Pro Asn Val Asp Pro Asn Ala Asn Pro Asn
            20                  25                  30

Val Asp Pro Asn Ala Asn Pro
        35

<210> SEQ ID NO 16
<211> LENGTH: 9
<212> TYPE: PRT
<213> ORGANISM: Artificial Sequence
<220> FEATURE:
<223> OTHER INFORMATION: Polyarginine:cysteine sequence embodiment
      conjugated to target antigen polypeptide sequence.

<400> SEQUENCE: 16

Cys Arg Arg Arg Arg Arg Arg Arg Arg
1               5

<210> SEQ ID NO 17
<211> LENGTH: 28
<212> TYPE: PRT
<213> ORGANISM: Artificial Sequence
<220> FEATURE:
<223> OTHER INFORMATION: P. falciparum circumsporozoite protein NANP
      repeat B-cell epitope target antigen.

<400> SEQUENCE: 17

Asn Ala Asn Pro Asn Val Asp Pro Asn Ala Asn Pro Asn Val Asp Pro
1               5                   10                  15

Asn Ala Asn Pro Asn Val Asp Pro Asn Ala Asn Pro
            20                  25

<210> SEQ ID NO 18
<211> LENGTH: 22
<212> TYPE: PRT
<213> ORGANISM: Artificial Sequence
<220> FEATURE:
<223> OTHER INFORMATION: Polyarginine:cysteine region, AAY leader
      sequence, and the P. yoellii circumsporozoite protein CD8 T-cell
      epitope target antigen.

<400> SEQUENCE: 18

Cys Arg Arg Arg Arg Arg Arg Arg Cys Ala Ala Tyr Ser Tyr Val
1               5                   10                  15

Pro Ser Ala Glu Gln Ile
            20

<210> SEQ ID NO 19
<211> LENGTH: 9
<212> TYPE: PRT
<213> ORGANISM: Artificial Sequence
<220> FEATURE:
<223> OTHER INFORMATION: P. yoellii circumsporozoite protein CD8 T-cell
      epitope target antigen.

<400> SEQUENCE: 19

Ser Tyr Val Pro Ser Ala Glu Gln Ile
1               5

<210> SEQ ID NO 20
<211> LENGTH: 13
<212> TYPE: PRT
<213> ORGANISM: Artificial Sequence
```

```
<220> FEATURE:
<223> OTHER INFORMATION: Polyarginine:cysteine region and AAY leader
      sequence.

<400> SEQUENCE: 20

Cys Arg Arg Arg Arg Arg Arg Arg Cys Ala Ala Tyr
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Dengue Viral CD8 epitope target antigen

<400> SEQUENCE: 21

Tyr Phe Ser Leu Gly Val Leu Gly Met
1               5

<210> SEQ ID NO 22
<211> LENGTH: 15
<212> TYPE: PRT
<213> ORGANISM: Artificial Sequence
<220> FEATURE:
<223> OTHER INFORMATION: Dengue Viral CD8 epitope target antigen

<400> SEQUENCE: 22

Ile Gly Cys Tyr Ser Gln Val Asn Pro Ile Thr Leu Thr Ala Ala
1               5                   10                  15

<210> SEQ ID NO 23
<211> LENGTH: 9
<212> TYPE: PRT
<213> ORGANISM: Artificial Sequence
<220> FEATURE:
<223> OTHER INFORMATION: Dengue Viral CD8 epitope target antigen

<400> SEQUENCE: 23

Tyr Ser Gln Val Asn Pro Ile Thr Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Dengue Viral CD8 epitope target antigen

<400> SEQUENCE: 24

Arg Met Leu Ile Asn Arg Phe Thr Met
1               5

<210> SEQ ID NO 25
<211> LENGTH: 9
<212> TYPE: PRT
<213> ORGANISM: Artificial Sequence
<220> FEATURE:
<223> OTHER INFORMATION: Dengue Viral CD8 epitope target antigen

<400> SEQUENCE: 25

Val Ala Phe Leu Arg Phe Leu Thr Ile
1               5

<210> SEQ ID NO 26
<211> LENGTH: 21
<212> TYPE: PRT
<213> ORGANISM: Artificial Sequence
```

```
<220> FEATURE:
<223> OTHER INFORMATION: Polyarginine:cysteine region, AAY leader
      sequence and S

```
<210> SEQ ID NO 32
<211> LENGTH: 13
<212> TYPE: PRT
<213> ORGANISM: Artificial Sequence
<220> FEATURE:
<223> OTHER INFORMATION: Polyglutamic acid:cysteine region E8C inserted
      into the EF Loop of the L1 protein.

<400> SEQUENCE: 32

Arg Pro Cys Glu Glu Glu Glu Glu Glu Glu Glu Pro Pro
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Polyglutamic acid:cysteine region E8C inserted
      into the H4 Loop of the L1 protein.

<400> SEQUENCE: 33

Ser Ile Leu Cys Glu Glu Glu Glu Glu Glu Glu Glu Pro Ala Thr
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Polyglutamic acid:cysteine region E8C inserted
      into the BC Loop of the L1 protein.

<400> SEQUENCE: 34

Tyr Tyr Pro Val Cys Glu Glu Glu Glu Glu Glu Glu Glu Val Ser Ala
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Polyglutamic acid:cysteine region E8C inserted
      into the HI Loop of the L1 protein.

<400> SEQUENCE: 35

Ala Ser Asp Cys Glu Glu Glu Glu Glu Glu Glu Glu Ser Lys Phe
1               5                   10                  15

<210> SEQ ID NO 36
<211> LENGTH: 32
<212> TYPE: PRT
<213> ORGANISM: Artificial Sequence
<220> FEATURE:
<223> OTHER INFORMATION: Polyglutamic acid:cysteine region E8C inserted
      into the HI Loop of the L1 protein.

<400> SEQUENCE: 36

Ala Ser Asp Gly Thr Gly Ser Ser Gly Cys Glu Glu Glu Glu Glu
1               5                   10                  15

Glu Glu Cys Gly Ser Ser Gly Leu Thr Glu Tyr Asp Ser Ser Lys Phe
            20                  25                  30

<210> SEQ ID NO 37
<211> LENGTH: 19
<212> TYPE: PRT
<213> ORGANISM: Artificial Sequence
```

```
<220> FEATURE:
<223> OTHER INFORMATION: Polyglutamic acid:cysteine region E8C inserted
      into the HI Loop of the L1 protein, replacement of amino acids
      349-353 (partial deletion).

<400> SEQUENCE: 37

Ala Ser Asp Gly Thr Cys Glu Glu Glu Glu Glu Glu Glu Asp Ser
1               5                   10                  15

Ser Lys Phe
```